US008637547B2

(12) United States Patent
Davidson et al.

(10) Patent No.: US 8,637,547 B2
(45) Date of Patent: Jan. 28, 2014

(54) COMPOUNDS WHICH INHIBIT MEMBERS OF THE HISTONE DEACETYLASE FAMILY OF ENZYMES AND THEIR USE IN THE TREATMENT OF CELL PROLIFERATIVE DISEASES

(75) Inventors: Alan Hornsby Davidson, Abingdon (GB); David Charles Festus Moffat, Abingdon (GB); Francesca Ann Day, Abingdon (GB); Alistair David Graham Donald, Abingdon (GB)

(73) Assignee: Chroma Therapeutics Ltd., Oxfordshire (GB)

( * ) Notice: Subject to any disclaimer, the term of this patent is extended or adjusted under 35 U.S.C. 154(b) by 5 days.

(21) Appl. No.: 12/443,096

(22) PCT Filed: Sep. 14, 2007

(86) PCT No.: PCT/GB2007/003504
§ 371 (c)(1),
(2), (4) Date: Apr. 17, 2009

(87) PCT Pub. No.: WO2008/040934
PCT Pub. Date: Apr. 10, 2008

(65) Prior Publication Data
US 2010/0010010 A1 Jan. 14, 2010

(30) Foreign Application Priority Data
Oct. 6, 2006 (GB) ................................. 0619753

(51) Int. Cl.
| A61K 31/4965 | (2006.01) |
| C07C 261/00 | (2006.01) |
| C07D 211/56 | (2006.01) |
| C07D 211/92 | (2006.01) |
| C07D 295/00 | (2006.01) |
| A01N 37/18 | (2006.01) |
| A61K 31/445 | (2006.01) |

(52) U.S. Cl.
USPC ............. 514/329; 560/39; 514/542; 546/224; 544/389

(58) Field of Classification Search
None
See application file for complete search history.

(56) References Cited

U.S. PATENT DOCUMENTS

| 4,254,220 | A | 3/1981 | Meiattini |
| 5,369,108 | A | 11/1994 | Breslow et al. |
| 7,932,246 | B2 | 4/2011 | Moffat et al. |
| 7,973,181 | B2 | 7/2011 | Davidson et al. |
| 8,003,695 | B2 | 8/2011 | Moffat et al. |
| 8,044,211 | B2 | 10/2011 | Moffat et al. |
| 8,106,091 | B2 | 1/2012 | Moffat et al. |
| 8,148,531 | B2 | 4/2012 | Davidson et al. |
| 8,211,900 | B2 | 7/2012 | Davidson |
| 8,217,050 | B2 | 7/2012 | Moffat et al. |
| 2009/0203711 | A1 | 8/2009 | Moffat |
| 2009/0215800 | A1 | 8/2009 | Davidson |
| 2009/0291978 | A1* | 11/2009 | Davidson et al. ............. 514/300 |
| 2010/0004250 | A1 | 1/2010 | Philips |
| 2010/0010057 | A1 | 1/2010 | Moffat |
| 2010/0216802 | A1 | 8/2010 | Moffat |
| 2010/0317678 | A1 | 12/2010 | Moffat et al. |

FOREIGN PATENT DOCUMENTS

| WO | 96/34851 | 11/1996 |
| WO | 01/18171 A2 | 3/2001 |
| WO | 01/38322 A1 | 5/2001 |
| WO | 01/60785 A1 | 8/2001 |
| WO | 01/70675 A2 | 9/2001 |
| WO | 02/22577 A2 | 3/2002 |
| WO | WO 02/22577 A | 3/2002 |
| WO | 02/26696 A1 | 4/2002 |
| WO | 02/26703 A1 | 4/2002 |
| WO | 02/30879 A2 | 4/2002 |
| WO | 02/069947 A2 | 9/2002 |
| WO | 03/011851 A2 | 2/2003 |
| WO | 03/066579 A2 | 8/2003 |
| WO | 03/075929 A1 | 9/2003 |
| WO | 03/076395 A1 | 9/2003 |
| WO | 03/076400 A1 | 9/2003 |
| WO | 03/076401 A1 | 9/2003 |
| WO | 03/076421 A1 | 9/2003 |
| WO | 03/076422 A1 | 9/2003 |
| WO | 03/076430 A1 | 9/2003 |
| WO | 03/082288 A1 | 10/2003 |

(Continued)

OTHER PUBLICATIONS

Han (Advances in Characterization of Pharmaceutical Hydrates. Trends in Bio/Pharmaceutical Industry, pp. 25-29. Mar. 2006).*
Vippagunta et al. (Adv. Drug. Deliv. Rev., 48: 3-26, 2001).*
Sternson et al., Organic Letters, "Synthesis of 7200 Small Molecules Based on a Substructural Analysis of the Histone Deacetylase Inhibitors Trichostatin and Trapoxin", vol. 3, No. 26, pp. 4239-4242, dated 2001.
Jung et al., J. Med. Chem., "Amide Analogues of Trichostatin A as Inhibitors of Histone Deacetylase and Inducers of Terminal Cell Differentiation", vol. 42, pp. 4669-4679, dated 1999.
Butler et al., Nature Reviews, "Histone deacetylase inhibitors as therapeutics for polyglutamine disorders", vol. 7, pp. 784-796, dated 2006.
Marks et al., Nature Reviews, Histone Deacetylases and Cancer: Causes and Therapies, vol. 1, pp. 194-202, dated 2001.

(Continued)

Primary Examiner — Anna Pagonakis

(57) ABSTRACT

Compounds of formula (I) inhibit HDAC activity, wherein A, B and D independently represent =C— or =N—; W is a divalent radical —CH=CH— or $CH_2CH_2$—; $R_1$ is a carboxylic acid group (—COOH), or an ester group which is hydrolysable by one or more intracellular carboxyesterase enzymes to a carboxylic acid group; $R_2$ is the side chain of a natural or non-natural alpha amino acid; z is 0 or 1; and Y, $L^1$, and $X^1$ are as defined in the claims.

(I)

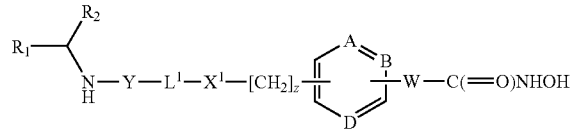

13 Claims, No Drawings

(56) References Cited

FOREIGN PATENT DOCUMENTS

| WO | 03/087057 A1 | 10/2003 |
|---|---|---|
| WO | 03/092686 A1 | 11/2003 |
| WO | 2004/013130 A1 | 2/2004 |
| WO | 2004/076386 A2 | 9/2004 |
| WO | 2004/092115 A2 | 10/2004 |
| WO | 2004/110989 A1 | 12/2004 |
| WO | 2005/004861 A1 | 1/2005 |
| WO | 2005/007091 A2 | 1/2005 |
| WO | 2005/013958 A1 | 2/2005 |
| WO | 2005/014588 A1 | 2/2005 |
| WO | 2005/018578 A2 | 3/2005 |
| WO | 2005/019174 A1 | 3/2005 |
| WO | 2005/026907 A2 | 3/2005 |
| WO | 2005/028447 A1 | 3/2005 |
| WO | 2005/030704 A1 | 4/2005 |
| WO | 2006/016680 | 2/2006 |

OTHER PUBLICATIONS

Berger, "An embarrassment of niches: the many covalent modifications of histones in transcriptional regulation," Oncogene, 2001, 20, 3007-3013.

Darkin-Rattray et al, "Apicidin: A Novel antiprotozoal agent that inhibits parasite histone deacetylase," Proc. Soc. Natl. Acad. Sci., 1996, 93, 13143-13147.

Dignam, "Accurate transcription initiation by RNA polymerase II in a soluble extract from isolated mammalian nuclei," Nucleic Acids Research, 1983, vol. 11, No. 5, 1475-1489.

Glaser, "HDAC inhibitors: Clinical update and mechanism-based potential," Biochemical Pharmacology, 2007, 74, 659-671.

Gray and Teh, "Histone Acetylation/Deacetylation and Cancer: An "Open" and "Shut" Case?," Current Molecular Medicine, 2001, 1, 401-429.

Grunstein, "Histone acetylation in chromatin structure and transcription," Nature, 1997, 389, 349-352.

Hempen and Brion, "Reduction of Acetylated α-Tubulin Immunoreactivity in Neurofibrillary Tangle-bearing Neurons in Alzheimer's Disease," J. Neuropathology and Experimental Neurology, 1996, 55, 964-972.

Hockly et al, "Suberoylanilide hydroxamic acid, a histone deacetylase inhibitor, ameliorates motor deficits in a mouse model of Huntington's disease," Proc. Soc. Natl. Acad. Sci., 2003, 100, 2041-2046.

Hughes, "Polyglutamine Disease: Acetyltransferases Awry," Current Biology, 2002, 12, R141-R143.

Kelly et al, "Histone deacetylase inhibitors: from target to clinical trials," Expert Opinion Investig Drugs, 2002, 11 (12). 1695-1713.

Kramer et al, "Histone deacetylase as a therapeutic target," Trends Endocrinology & Metabolism, 2001, 12, 294-300.

McCampbell et al, "Histone deacetylase inhibitors reduce polyglutamine toxicity," Proc. Soc. Natl. Acad. Sci., 2001, vol. 98, No. 26, 15179-15184.

Mishra et al, "Histone deacetylase inhibitors modulate renal disease in the MRL-lpr/lpr mouse," Journal of Clin. Invest., 2003, vol. 111, No. 4, 539-552.

Mosley and Ozcan, "Glucose Regulates Insulin Gene Transcription by Hyperacetylation of Histone H4," Journal of Biological Chemistry, 2003, vol. 278, No. 22, 19660-19666.

Naldini and Carraro, "Roles of Inflammatory Mediators in Angiogenesis," Current Drug Targets, Inflammation & Allergy, 2005, vol. 4, 3-8.

Skehan et al, "New Colorimetric Cytotoxicity Assay for Anticancer-Drug Screening," J. Natl. Canc. Inst., 1990, vol. 82, No. 13, 1107-1112.

Skov et al, "Histone deacetylase inhibitors: a new class of immunosuppressors targeting a novel signal pathway essential for CD154 expression," Blood, 2003, vol. 101, No. 4, 1430-1438.

van Roon et al., "Selective Elimination of Synovial Inflammatory Macrophages in Rheumatoid Arthritis by an Fcγ Receptor I-Directed Immunotoxin," Arthritis and Rheumatism, 2003, vol. 48, No. 5, 1229-1238.

Vigushin and Coombes, "Histone deacetylase inhibitors in cancer treatment," Anti-Cancer Drugs, 2002, vol. 13, 1-13.

Wade et al, "Histone acetylation: chromatin in action," Trends Biochem. Sci., 1997, 22, 128-132.

Witt et al, "Induction of fetal hemoglobin expression by the histone deacetylase inhibitor apicidin," Blood, 2003, vol. 101, No. 5, 2001-2007.

Wolffe, "Histone Deacetylase: A Regulator of Transcription," Science, 1996, 272, 371-372.

* cited by examiner

COMPOUNDS WHICH INHIBIT MEMBERS OF THE HISTONE DEACETYLASE FAMILY OF ENZYMES AND THEIR USE IN THE TREATMENT OF CELL PROLIFERATIVE DISEASES

CROSS REFERENCE TO RELATED APPLICATIONS:

This application is a National Stage application of copending PCT application PCT/GB2007/003504 filed Sep. 14, 2007, which claims the benefit of Great Britain application number 0619753.7 filed Jun. 10, 2006. These applications are incorporated herein by reference in their entireties.

This invention relates to compounds which inhibit members of the histone deacetylase family of enzymes and to their use in the treatment of cell proliferative diseases, including cancers, polyglutamine diseases, for example Huntington disease, neurogenerative diseases for example Alzheimer disease, autoimmune disease for example rheumatoid arthritis and organ transplant rejection, diabetes, haematological disorders, inflammatory disease, cardiovascular disease, atherosclerosis, and the inflammatory sequelia of infection.

BACKGROUND TO THE INVENTION

In eukaryotic cells DNA is packaged with histones, to form chromatin. Approximately 150 base pairs of DNA are wrapped twice around an octamer of histones (two each of histones 2A, 2B, 3 and 4) to form a nucleosome, the basic unit of chromatin. The ordered structure of chromatin needs to be modified in order to allow transcription of the associated genes. Transcriptional regulation is key to differentiation, proliferation and apoptosis, and is, therefore, tightly controlled. Control of the changes in chromatin structure (and hence of transcription) is mediated by covalent modifications to histones, most notably of the N-terminal tails. Covalent modifications (for example methylation, acetylation, phosphorylation and ubiquitination) of the side chains of amino acids are enzymatically mediated (A review of the covalent modifications of histones and their role in transcriptional regulation can be found in S. L. Berger, *Oncogene*, 2001, 20, 3007-3013. See M. Grunstein, *Nature*, 1997, 389, 349-352; A. P. Wolffe, *Science*, 1996, 272, 371-372; and P. A. Wade et al, *Trends Biochem. Sci.*, 1997, 22, 128-132 for reviews of histone acetylation and transcription).

Acetylation of histones is associated with areas of chromatin that are transcriptionally active, whereas nucleosomes with low acetylation levels are, typically, transcriptionally silent. The acetylation status of histones is controlled by two enzyme classes of opposing activities; histone acetyltransferases (HATs) and histone deacetylases (HDACs). In transformed cells it is believed that inappropriate expression of HDACs results in silencing of tumour suppressor genes (For a review of the potential roles of HDACs in tumorigenesis see S. G. Gray and B. T. The, *Curr. Mol. Med.*, 2001, 1, 401-429). Inhibitors of HDAC enzymes have been described in the literature and shown to induce transcriptional reactivation of certain genes resulting in the inhibition of cancer cell proliferation, induction of apoptosis and inhibition of tumour growth in animals (For review see W. K. Kelly et al, *Expert Opin. Investig. Drugs*, 2002, 11, 1695-1713). Such findings suggest that HDAC inhibitors have therapeutic potential in the treatment of proliferative diseases such as cancer (O. H. Kramer et al, *Trends Endocrinol.*, 2001, 12, 294-300; D. M. Vigushin and R. C. Coombes, *Anticancer Drugs*, 2002, 13, 1-13).

In addition, others have proposed that aberrant HDAC activity or histone acetylation is implicated in the following diseases and disorders; polyglutamine disease, for example Huntingdon disease (R. E. Hughes, *Curr Biol*, 2002, 12, R141-R143; A. McCampbell et al, *Proc. Soc. Natl. Acad. Sci.*, 2001, 98, 15179-15184; E. Hockly et al, *Proc. Soc. Natl. Acad. Sci.*, 2003, 100, 2041-2046), other neurodegenerative diseases, for example Alzheimer disease (B. Hempen and J. P. Brion, *J. Neuropathol. Exp. Neurol.*, 1996, 55, 964-972), autoimmune disease and organ transplant rejection (S. Skov et al, *Blood*, 2003, 101, 1430-1438; N. Mishra et al, *J. Clin. Invest*, 2003, 111, 539-552), diabetes (A. L. Mosley and S. Ozcan, *J. Biol. Chem.*, 2003, 278, 19660-19666) and diabetic complications, infection (including protozoal infection (S. J. Darkin-Rattray et al, *Proc. Soc. Natl. Acad. Sci.*, 1996, 93, 13143-13147)) and haematological disorders including thalassemia (O. Witt et al, *Blood*, 2003, 101, 2001-2007). The observations contained in these manuscripts suggest that HDAC inhibition should have therapeutic benefit in these, and other related, diseases.

Many types of HDAC inhibitor compounds have been suggested, and several such compounds are currently being evaluated clinically, for the treatment of cancers. For example, the following patent publications disclose such compounds:

| U.S. Pat. No. 5,369,108 | WO 01/70675 | WO 02/30879 |
|---|---|---|
| WO 01/18171 | WO 01/38322 | WO 02/26703 |
| U.S. Pat. No. 4,254,220 | WO 02/069947 | WO 02/26696 |
| WO 03/082288 | WO 02/22577 | WO 03/075929 |
| WO 03/076395 | WO 03/076400 | WO 03/076401 |
| WO 03/076421 | WO 03/076430 | WO 03/076422 |
| WO 03/082288 | WO 03/087057 | WO 03/092686 |
| WO 03/066579 | WO 03/011851 | WO 04/013130 |
| WO 04/110989 | WO 04/092115 | WO 04/224991 |
| WO 04/076386 | WO 05/014588 | WO 05/018578 |
| WO 05/019174 | WO 05/004861 | WO 05/007091 |
| WO 05/030704 | WO 05/013958 | WO 05/028447 |
| WO 05/026907 | WO 06/0166 | |

Many of the HDAC inhibitors known in the art have a structural template, which may be represented as in formula (A):

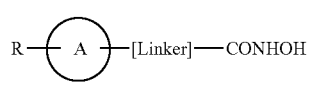

(A)

wherein ring A is a carbocyclic or heterocyclic ring system with optional substituents R, and [Linker] is a linker radical of various types. The hydroxamate group functions as a metal binding group, interacting with the metal ion at the active site of the HDAC enzyme, which lies at the base of a pocket in the folded enzyme structure. The ring or ring system A lies within or at the entrance to the pocket containing the metal ion, with the -[Linker]- radical extending deeper into that pocket linking A to the metal binding hydroxamic acid group. In the art, and occasionally herein, the ring or ring system A is sometimes informally referred to as the "head group" of the inhibitor.

The use of prodrugs to enhance the delivery to target organs and tissues, or to overcome poor pharmacokinetic properties of the parent drug, is a well known medicinal chemistry approach. Administration of ester prodrugs, for example, which are hydrolysed by serum carboxyesterases in vivo to the active parent acids, can result in higher serum levels of the parent acid than administration of the acid itself.

BRIEF DESCRIPTION OF THE INVENTION

This invention makes available a new class of HDAC inhibitors having pharmaceutical utility in the treatment of diseases such as cancers or inflammation which benefit from intracellular inhibition of HDAC, one subset of which has an alpha amino acid ester grouping which facilitates penetration of the agent through the cell wall, and thereby allows intracellular carboxyesterase activity to hydrolyse the ester to release the parent acid. Being charged, the acid is not readily transported out of the cell, where it therefore accumulates to increase the intracellular concentration of active HDAC inhibitor. This leads to increases in potency and duration of action. This subset of compounds of the invention is therefore characterised by having an alpha amino acid ester moiety which is a substrate for intracellular carboxyesterase (also referred to herein as an "esterase motif") covalently linked to the parent molecular template, and to the corresponding de-esterified parent acids.

DETAILED DESCRIPTION OF THE INVENTION

According to the invention there is provided a compound of formula (I), or a salt, N-oxide, hydrate or solvate thereof:

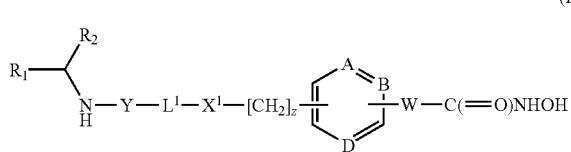

(I)

wherein

A, B and D independently represent =C— or =N—;

W is a divalent radical —CH=CH— or —CH$_2$CH$_2$—;

$R_1$ is a carboxylic acid group (—COOH), or an ester group which is hydrolysable by one or more intracellular carboxyesterase enzymes to a carboxylic acid group;

$R_2$ is the side chain of a natural or non-natural alpha amino acid;

Y is a bond, —C(=O)—, —S(=O)$_2$—, —C(=O)O—, —C(=O)NR$_3$—, —C(=S)—NR$_3$, —C(=NH)NR$_3$ or —S(=O)$_2$NR$_3$— wherein $R_3$ is hydrogen or optionally substituted C$_1$-C$_6$ alkyl;

$L^1$ is a divalent radical of formula -(Alk$^1$)$_m$(Q)$_n$(Alk$^2$)$_p$- wherein m, n and p are independently 0 or 1, Q is (i) an optionally substituted divalent mono- or bicyclic carbocyclic or heterocyclic radical having 5-13 ring members, or (ii), in the case where both m and p are 0, a divalent radical of formula —X$^2$-Q$^1$- or -Q$^1$-X$^2$— wherein X$^2$ is —O—, S— or NR$^A$— wherein R$^A$ is hydrogen or optionally substituted C$_1$-C$_3$ alkyl, and Q$^1$ is an optionally substituted divalent mono- or bicyclic carbocyclic or heterocyclic radical having 5-13 ring members, Alk$^1$ and Alk$^2$ independently represent optionally substituted divalent C$_3$-C$_7$ cycloalkyl radicals, or optionally substituted straight or branched, C$_1$-C$_6$ alkylene, C$_2$-C$_6$ alkenylene, or C$_2$-C$_6$ alkynylene radicals which may optionally contain or terminate in an ether (—O—), thioether (—S—) or amino (—NR$^A$—) link wherein R$^A$ is hydrogen or optionally substituted C$_1$-C$_3$ alkyl;

X$^1$ represents a bond; —C(=O); or —S(=O)$_2$—; —NR$_4$C (=O)—, —C(=O)NR$_4$—, —NR$_4$C(=O)NR$_5$—, —NR$_4$S(=O)$_2$—, or —S(=O)$_2$NR$_4$— wherein R$_4$ and R$_5$ are independently hydrogen or optionally substituted C$_1$-C$_6$ alkyl; and z is 0 or 1;

PROVIDED THAT, when A, B and D are each =C— and W is —CH=CH— and $R_1$ is a carboxylic acid group or a methyl or tert-butyl ester thereof, then $R_2$ is not the side chain of tryptophan, namely indol-3-ylmethyl.

Although the above definition potentially includes molecules of high molecular weight, it is preferable, in line with general principles of medicinal chemistry practice, that the compounds with which this invention is concerned should have molecular weights of no more than 600.

In another broad aspect the invention provides the use of a compound of the invention in the preparation of a composition for inhibiting the activity of histone deacetylase.

The compounds with which the invention is concerned may be used for the inhibition of histone deacetylase activity, ex vivo or in vivo.

In one aspect of the invention, the compounds of the invention may be used in the preparation of a composition for the treatment of cell-proliferation disease, polyglutamine disease, neurodegenerative disease, autoimmune disease, inflammatory disease, organ transplant rejection, diabetes, haematological disorders or infection.

In another aspect, the invention provides a method for the treatment of the foregoing disease types, which comprises administering to a subject suffering such disease an effective amount of a compound of the invention.

Terminology

The term "ester" or "esterified carboxyl group" means a group R$_9$O(C=O)— in which R$_9$ is the group characterising the ester, notionally derived from the alcohol R$_9$OH.

As used herein, the term "(C$_a$-C$_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent (C$_a$-C$_b$)alkylene radical" wherein a and b are integers refers to a saturated hydrocarbon chain having from a to b carbon atoms and two unsatisfied valences.

As used herein the term "(C$_a$-C$_b$)alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent (C$_a$-C$_b$)alkenylene radical" means a hydrocarbon chain having from a to b carbon atoms, at least one double bond, and two unsatisfied valences.

As used herein the term "C$_a$-C$_b$ alkynyl" wherein a and b are integers refers to straight chain or branched chain hydrocarbon groups having from a to b carbon atoms and having in addition one triple bond. For a=2 and b=6, this term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent (C$_a$-C$_b$)alkynylene radical" wherein a and b are integers refers to a divalent hydrocarbon chain having from a to b carbon atoms, and at least one triple bond.

As used herein the term "carbocyclic" refers to a mono-, bi- or tricyclic radical having up to 16 ring atoms, all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, $(C_1-C_6)$ alkyl, $(C_1-C_6)$alkoxy, hydroxy, hydroxy$(C_1-C_6)$alkyl, mercapto, mercapto$(C_1-C_6)$alkyl, $(C_1-C_6)$alkylthio, phenyl, halo (including fluoro, bromo and chloro), trifluoromethyl, trifluoromethoxy, nitro, nitrile (—CN), oxo, —COOH, —COOR$^A$, COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OH, —NR$^B$S$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein R$^A$ and R$^B$ are independently a $(C_1-C_6)$alkyl, $(C_3-C_6)$ cycloalkyl, phenyl or monocyclic heteroaryl having 5 or 6 ring atoms, or RA and RB when attached to the same nitrogen atom form a cyclic amino group (for example morpholino, piperidinyl, piperazinyl, or tetrahydropyrrolyl). An "optional substituent" may be one of the foregoing substituent groups.

As used herein, the term "nitrogen substituent" means a substituent on a nitrogen atom which is selected from the following:

amino $(C_1-C_6)$alkyl eg aminoethyl, $(C_1-C_3)$alkylamino-$(C_1-C_6)$alkyl-, $(C_1-C_3)$dialkylamino-$(C_1-C_6)$alkyl, hydroxy$(C_1-C_6)$alkyl eg hydroxyethyl, $(C_1-C_3)$alkoxy-$(C_1-C_6)$alkyl- eg methoxyethyl, mercapto$(C_1-C_3)$alkyl, $(C_1-C_3)$alkylmercapto-$(C_1-C_6)$alkyl-, carboxamido$(C_1-C_6)$alkyl e.g.

—CH$_2$CONH$_2$, aminosulphonyl$(C_1-C_6)$alkyl- e.g. —CH$_2$SO$_2$NH$_2$, $(C_1-C_3)$alkylaminosulphonyl-$(C_1-C_6)$ alkyl- e.g. —CH$_2$SO$_2$NH Me, $(C_1-C_3)$dialkylaminosulphonyl-$(C_1-C_6)$alkyl e.g.

—CH$_2$SO$_2$NMe$_2$, $(C_1-C_6)$alkanoyl, $(C_1-C_6)$alkylsulphonyl, aminosulphonyl (—SO$_2$NH$_2$), $(C_1-C_6)$alkylaminosulphonyl e.g. —SO$_2$NHMe, $(C_1-C_6)$dialkylaminosulphonyl e.g. —SO$_2$NMe$_2$, optionally substituted phenylaminosulphonyl, carboxamido (—CONH$_2$), $(C_1-C_6)$alkylaminocarbonyl, $(C_1-C_6)$dialkylaminocarbonyl, morpholinyl$(C_1-C_6)$alkyl, imidazolyl$(C_1-C_6)$alkyl, triazolyl$(C_1-C_6)$alkyl, or monocyclic heterocycloalkyl$(C_1-C_6)$alkyl, optionally substituted in the imidazolyl, triazolyl or heterocyclyl ring, eg piperidinyl$(C_1-C_6)$alkyl, piperazinyl$(C_1-C_6)$alkyl or 4-$((C_1-C_6)$alkyl)piperazinyl $(C_1-C_6)$alkyl.

The term "side chain of a natural or non-natural alpha-amino acid" refers to the group R$_2$ in a natural or non-natural amino acid of formula NH$_2$—CH(R$_2$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, a-aminoadipic acid, α-amino-n-butyric acid, 3,4-dihydroxyphenylalanine, homoserine, β-methylserine, ornithine, pipecolic acid, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When R$_2$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a $C_1-C_6$ alkyl ester), amino groups may be converted to amides (for example as a NHCOC$_1$-C$_6$ alkyl amide) or carbamates (for example as an NHC(=O)OC$_1$-C$_6$ alkyl or NHC(=O)OCH$_2$Ph carbamate), hydroxyl groups may be converted to ethers (for example an OC$_1$-C$_6$ alkyl or a O(C$_1$-C$_6$ alkyl)phenyl ether) or esters (for example a OC(=O)C$_1$-C$_6$ alkyl ester) and thiol groups may be converted to thioethers (for example a tert-butyl or benzyl thioether) or thioesters (for example a SC(=O)C$_1$-C$_6$ alkyl thioester).

Examples of side chains of non-natural alpha amino acids include those referred to below in the discussion of suitable R$_2$ groups for use in compounds of the present invention.

As used herein the term "salt" includes base addition, acid addition and quaternary salts. compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like.

It is expected that compounds of the invention may be recovered in hydrate or solvate form. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds of the invention which contain one or more actual or potential chiral centres, because of the presence of asymmetric carbon atoms, can exist as a number of diastereoisomers with R or S stereochemistry at each chiral centre. The invention includes all such diastereoisomers and mixtures thereof.

Further Discussion

As stated above, the esters of the invention are primarily prodrugs of the corresponding carboxylic acids to which they are converted by intracellular esterases. However, for so long as they remain unhydrolised, the esters may have HDAC inhibitory activity in their own right. The compounds of the invention include not only the ester, but also the corresponding carboxylic and hydrolysis products.

The Hydroxamate Group —C(=O)NHOH

In the compounds of the invention, the hydroxamate group functions as a metal binding group, interacting with the metal ion at the active site of the HDAC enzyme, which lies at the base of a pocket in the folded enzyme structure.

The Ring Containing A, B and D

Each of A, B and D may be —C=, or at least one of A, B and D may be —N=, or A may be —C= and B and D may each be —N=;

The radical —Y-L$^1$-X$^1$—[CH$_2$]$_z$—

L$^1$ may be selected from:
(i) a bond;
(ii) —O—, —S—, —C(=O)—, —S(=O)$_2$—, —NR$^1$—, —C(=O)NR$^1$—, —S(=O)$_2$NR$^1$—, —NR$^1$C(=O)—, —NR$^1$S(=O)$_2$—, —NR$^1$(CH2)$_m$—, —NR$^1$C(=O)(CH2)$_m$—, —NR$^1$S(=O)$_2$(CH$_2$)$_m$—, —NR$^2$C(=O)NR$^1$—, —NR$^1$C(=O)(CH$_2$)$_m$Ar—, or —NR$^1$S(=O)$_2$(CH$_2$)$_m$Ar—, wherein R$^1$ and R$^2$ are independently hydrogen, C$_1$-C$_4$ alkyl, or a nitrogen substituent, m is 0, 1, 2 or 3, and Ar is a divalent phenyl radical or a divalent mono-, or bi-cyclic heteroaryl radical having 5 to 13 ring members; and
(iii) an optionally substituted, straight or branched, C$_1$-C$_6$ alkylene, C$_2$-C$_6$ alkenylene or C$_2$-C$_6$ alkynylene radical which may optionally contain or terminate in an ether (—O—), thioether (—S—) or amino (—NR$^A$—) link wherein R$^A$ is hydrogen, C$_1$-C$_3$ alkyl, or a nitrogen substituent;

In the radical L$^1$, Alk$^1$ and Alk$^2$, when present, may be selected from, for example, —CH$_2$—, —CH$_2$CH$_2$—, —CH$_2$CH$_2$CH$_2$—, —CH$_2$O—, —CH$_2$CH$_2$O—, —CH$_2$CH$_2$CH$_2$)—, and divalent cyclopropyl, cyclopentyl and cyclohexyl radicals.

Also in the radical L$^1$, Q$^1$ may be, for example, 1,4-phenylene.

Also in the radical L$^1$, m and p may both be 0, or n and p may be 0 while m is 1, or m, n and p may all be 0, Specific examples of the radical —Y-L$^1$-X$^1$—[CH$_2$]$_z$— are —C(=O)—, —C(=O)NH—, —(CH$_2$)$_v$—, —(CH$_2$)$_v$O—, —C(=O)—(CH$_2$)$_v$—, —C(=O)(CH$_2$)$_v$O—, —C(=O)NH(CH$_2$)$_w$—, —C(=O)NH(CH$_2$)$_w$O—

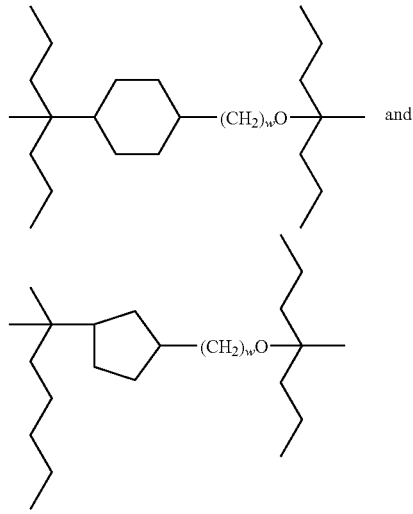

wherein v is 1, 2, 3 or 4 and w is 1, 2 or 3.

Amongst preferred —Y-L$^1$-X$^1$—[CH$_2$]$_z$— radicals are —CH$_2$—, —CH$_2$O—, —C(=O)—CH$_2$—, —C(=O)—CH$_2$O—, —C(=O)—NH—CH$_2$—, or —C(=O)—NH—CH$_2$O—.

X$^1$ may be, for example, —NR$_3$—, —S—, —O—, —C(=O)NR$_3$—, —NR$_3$C(=O)—, or —C(=O)O—, wherein R$_3$ is hydrogen, C$_1$-C$_6$ alkyl, or a nitrogen substituent, or in other cases a bond.

In the radical L$^1$, Alk$^1$ and Alk$^2$, when present, may be selected from —CH$_2$—, —CH$_2$CH$_2$—, —CH$_2$CH$_2$CH$_2$—, and divalent cyclopropyl, cyclopentyl and cyclohexyl radicals.

In the radical L$^1$, Q$^1$ may be, for example, a divalent phenyl radical or a mono-, or bi-cyclic heteroaryl radical having 5 to 13 ring members, such as 1,4-phenylene.

Specific examples of the radical -L$^1$-X$^1$—[CH$_2$]$_z$— are —(CH$_2$)$_3$NH—, —CH$_2$C(=O)NH—, —CH$_2$CH$_2$C(=O)NH—, —CH$_2$C(O)O—, —CH$_2$S—, —CH$_2$CH$_2$C(O)O—, —(CH$_2$)$_4$NH—, —CH$_2$CH$_2$S—, —CH$_2$O, —CH$_2$CH$_2$O—

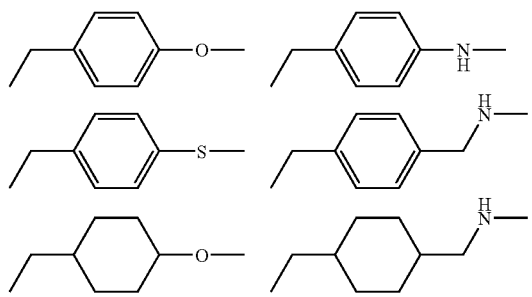

In a simple subset of compounds of the invention, the radical —YL$^1$X$^1$—[CH$_2$]$_z$— is —CH$_2$—.

The Ester Group R$_1$

The ester group R$_1$ must be one which in the compound of the invention is hydrolysable by one or more intracellular carboxyesterase enzymes to a carboxylic acid group. Intracellular carboxyesterase enzymes capable of hydrolysing the ester group of a Compound of the invention to the corresponding acid include the three known human enzyme isotypes hCE-1, hCE-2 and hCE-3. Although these are considered to be the main enzymes, other enzymes such as biphenylhydrolase (BPH) may also have a role in hydrolysing the ester. In general, if the carboxyesterase hydrolyses the free amino acid ester to the parent acid it will, subject to the N-carbonyl dependence of hCE-2 and hCE-3 discussed below, also hydrolyse the ester motif when covalently conjugated to the HDAC inhibitor. Hence, the broken cell assay provides a straightforward, quick and simple first screen for esters which have the required hydrolysis profile. Ester motifs selected in that way may then be re-assayed in the same carboxyesterase assay when conjugated to the inhibitor via the chosen conjugation chemistry, to confirm that it is still a carboxyesterase substrate in that background.

Subject to the requirement that they be hydrolysable by intracellular carboxyesterase enzymes, examples of particular ester groups $R_1$ include those of formula —(C=O)$OR_9$ wherein $R_9$ is $R_{20}R_{21}R_{22}C$— wherein
- (i) $R_{20}$ is hydrogen or optionally substituted $(C_1-C_3)$alkyl-$(Z^1)_a$-[$(C_1-C_3)$alkyl]$_b$- or $(C_2-C_3)$alkenyl-$(Z^1)_a$-[$(C_1-C_3)$alkyl]$_b$- wherein a and b are independently 0 or 1 and $Z^1$ is —O—, —S—, or —$NR_C$— wherein $R_c$ is hydrogen or $(C_1-C_3)$alkyl; and $R_{21}$ and $R_{22}$ are independently hydrogen or $(C_1-C_3)$alkyl-;
- (ii) $R_{20}$ is hydrogen or optionally substituted $R_{12}R_{13}N$—$(C_1-C_3)$alkyl- wherein $R_{12}$ is hydrogen or $(C_1-C_3)$alkyl and $R_{13}$ is hydrogen or $(C_1-C_3)$alkyl; or $R_{12}$ and $R_{13}$ together with the nitrogen to which they are attached form an optionally substituted monocyclic heterocyclic ring of 5- or 6-ring atoms or bicyclic heterocyclic ring system of 8 to 10 ring atoms, and $R_{21}$ and $R_{22}$ are independently hydrogen or $(C_1-C_3)$alkyl-; or
- (iii) $R_{20}$ and $R_{21}$ taken together with the carbon to which they are attached form an optionally substituted monocyclic carbocyclic ring of from 3 to 7 ring atoms or bicyclic carbocyclic ring system of 8 to 10 ring atoms, and $R_{22}$ is hydrogen.

Within these classes, $R_9$ may be, for example, methyl, ethyl, n- or iso-propyl, n- sec- or tert-butyl, cyclohexyl, allyl, phenyl, benzyl, 2-, 3- or 4-pyridylmethyl, N-methylpiperidin-4-yl, tetrahydrofuran-3-yl, methoxyethyl, indonyl, norbonyl, dimethylaminoethyl, morpholinoethyl. Currently preferred is where $R_9$ is cyclopentyl.

Macrophages are known to play a key role in inflammatory disorders through the release of cytokines in particular TNFα and IL-1 (van Roon et al., *Arthritis and Rheumatism*, 2003, 1229-1238). In rheumatoid arthritis they are major contributors to the maintenance of joint inflammation and joint destruction. Macrophages are also involved in tumour growth and development (Naldini and Carraro, *Curr Drug Targets Inflamm Allergy*, 2005, 3-8). Hence agents that selectively target macrophage cell proliferation and function could be of value in the treatment of cancer and autoimmune disease. Targeting specific cell types would be expected to lead to reduced side-effects. The inventors have discovered a method of targeting inhibitors to cells that express hCE-1, in particular macrophages and other cells derived from the myelo-monocytic lineage such as monocytes, osteoclasts and dendritic cells, This is based on the observation that the way in which the esterase motif is linked to the inhibitor determines whether it is hydrolysed by all three human carboxylesterases or just by hCE-1, and hence whether or not it accumulates in different cell types. Specifically it has been found that macrophages and other cells derived from the myelo-monocytic lineage, both normal and cancerous, contain the human carboxylesterase hCE-1 whereas other cell types do not. In the general formula (I) when the nitrogen of the esterase motif $R_1CH(R_2)NH$— is not directly linked to a carbonyl (—C(=O)—), ie when Y is not a —C(=O), —C(=O)O— or —C(=O)$NR_3$— radical, the ester will only be hydrolysed by hCE-1 and hence the inhibitors selectively accumulate in macrophage-related cells.

The Amino Acid Side Chain $R_2$

Subject to the requirement that the ester group $R_1$ be hydrolysable by intracellular carboxylesterase enzymes, the identity of the side chain group $R_2$ is not critical for non-macrophage selective compounds.

Examples of amino acid side chains include:

$C_1-C_6$ alkyl, phenyl, 2,-3-, or 4-hydroxyphenyl, 2,-3-, or 4-methoxyphenyl, 2,-3-, or 4-pyridylmethyl, benzyl, phenylethyl, 2-, 3-, or 4-hydroxybenzyl, 2,-3-, or 4-benzyloxybenzyl, 2,-3-, or 4-$C_1-C_6$ alkoxybenzyl, and benzyloxy $(C_1-C_6$alkyl)-groups;

the characterising group of a natural α amino acid, in which any functional group may be protected;

groups -[Alk]$_n R_6$ where Alk is a $(C_1-C_6)$alkyl or $(C_2-C_6)$alkenyl group optionally interrupted by one or more —O—, or —S— atoms or —$N(R_7)$— groups [where $R_7$ is a hydrogen atom or a $(C_1-C_6)$alkyl group], n is 0 or 1, and $R_6$ is an optionally substituted cycloalkyl or cycloalkenyl group;

a benzyl group substituted in the phenyl ring by a group of formula —$OCH_2COR_8$ where $R_8$ is hydroxyl, amino, $(C_1-C_6)$alkoxy, phenyl$(C_1-C_6)$alkoxy, $(C_1-C_6)$alkylamino, di$((C_1-C_6)$alkyl)amino, phenyl$(C_1-C_6)$alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid;

a heterocyclic$(C_1-C_6)$alkyl group, either being unsubstituted or mono- or di-substituted in the heterocyclic ring with halo, nitro, carboxy, $(C_1-C_6)$alkoxy, cyano, $(C_1-C_6)$alkanoyl, trifluoromethyl $(C_1-C_6)$alkyl, hydroxy, formyl, amino, $(C_1-C_6)$alkylamino, di-$(C_1-C_6)$alkylamino, mercapto, $(C_1-C_6)$alkylthio, hydroxy$(C_1-C_6)$alkyl, mercapto $(C_1-C_6)$alkyl or $(C_1-C_6)$alkylphenylmethyl; and a group —$CR_a R_b R_c$ in which:

each of $R_a$, $R_b$ and $R_c$ is independently hydrogen, $(C_1-C_6)$ alkyl, $(C_2-C_6)$alkenyl, $(C_2-C_6)$alkynyl, phenyl$(C_1-C_6)$ alkyl, $(C_3-C_8)$cycloalkyl; or $R_c$ is hydrogen and $R_a$ and $R_b$ are independently phenyl or heteroaryl such as pyridyl; or $R_c$ is hydrogen, $(C_1-C_6)$alkyl, $(C_2-C_6)$alkenyl, $(C_2-C_6)$ alkynyl, phenyl$(C_1-C_6)$alkyl, or $(C_3-C_8)$cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently $(C_1-C_6)$alkyl, $(C_2-C_6)$ alkenyl, $(C_2-C_6)$alkynyl, phenyl$(C_1-C_6)$alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, ($C_1$-$C_4$)perfluoroalkyl, —CH$_2$OH, —CO$_2$($C_1$-$C_6$)alkyl, —O($C_1$-$C_6$)alkyl, —O($C_2$-$C_6$)alkenyl, —S($C_1$-$C_6$)alkyl, —SO($C_1$-$C_6$)alkyl, —SO$_2$($C_1$-$C_6$) alkyl, —S($C_2$-$C_6$)alkenyl, —SO($C_2$-$C_6$)alkenyl, —SO$_2$($C_2$-$C_6$)alkenyl or a group -Q-W wherein Q represents a bond or —O—, —S—, —SO— or —SO$_2$— and W represents a phenyl, phenylalkyl, ($C_3$-$C_8$)cycloalkyl, ($C_3$-$C_8$)cycloalkylalkyl, ($C_4$-$C_8$)cycloalkenyl, ($C_4$-$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$-$C_6$)alkyl, —CONH$_2$, —CONH($C_1$-$C_6$)alkyl, —CONH($C_1$-$C_6$alkyl)$_2$, —CHO, —CH$_2$OH, ($C_1$-$C_4$)perfluoroalkyl, —O($C_1$-$C_6$)alkyl, —S($C_1$-$C_6$)alkyl, —SO($C_1$-$C_6$)alkyl, —SO$_2$($C_1$-$C_6$)alkyl, —NO$_2$, —NH$_2$, —NH($C_1$-$C_6$) alkyl, —N(($C_1$-$C_6$)alkyl)$_2$, —NHCO($C_1$-$C_6$)alkyl, ($C_1$-$C_6$)alkyl, ($C_2$-$C_6$)alkenyl, ($C_2$-$C_6$)alkynyl, ($C_3$-$C_8$)cycloalkyl, ($C_4$-$C_8$)cycloalkenyl, phenyl or benzyl.

Examples of particular $R_2$ groups include hydrogen (the glycine "side chain"), benzyl, phenyl, cyclohexylmethyl, cyclohexyl, pyridin-3-ylmethyl, tert-butoxymethyl, iso-butyl, sec-butyl, tert-butyl, 1-benzylthio-1-methylethyl, 1-methylthio-1-methylethyl, 1-mercapto-1-methylethyl, and phenylethyl. Presently preferred $R_2$ groups include phenyl, benzyl, and iso-butyl, cyclohexyl and t-butoxymethyl.

For compounds of the invention which are to be administered systemically, esters with a slow rate of carboxylesterase cleavage are preferred, since they are less susceptible to pre-systemic metabolism. Their ability to reach their target tissue intact is therefore increased, and the ester can be converted inside the cells of the target tissue into the acid product. However, for local administration, where the ester is either directly applied to the target tissue or directed there by, for example, inhalation, it will often be desirable that the ester has a rapid rate of esterase cleavage, to minimise systemic exposure and consequent unwanted side effects. In the compounds of this invention, if the carbon adjacent to the alpha carbon of the alpha amino acid ester ester is monosubstituted, ie $R_2$ is CH$_2$R$^z$ (R$^z$ being the mono-substituent) then the esters tend to be cleaved more rapidly than if that carbon is di- or tri-substituted, as in the case where $R_2$ is, for example, phenyl or cyclohexyl.

For macrophage selective compounds, side chains such as those of valine (ie —CH(CH$_3$)$_2$), cyclohexylglycine (ie cyclohexyl), t-butylserine (ie —CH$_2$O(t-Bu)), t-butylcysteine (ie —CH$_2$S(t-Bu)), and phenylglycine (ie phenyl) are currently preferred.

One subset of the compounds of the invention has formula (IA):

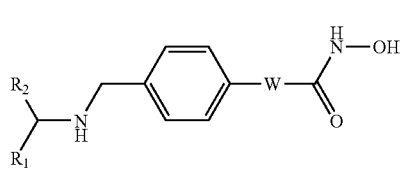

wherein W, $R_1$ and $R_2$ are as defined and further discussed above.

Another subset of the compounds of the invention has formula (IB):

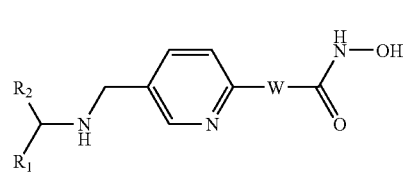

wherein W, $R_1$ and $R_2$ are as defined and further discussed above.

Yet another subset of the compounds of the invention has formula (IC):

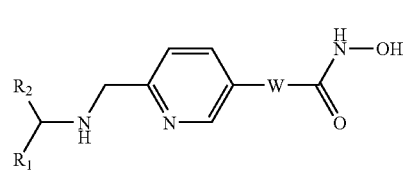

wherein W, $R_1$ and $R_2$ are as defined and further discussed above.

ALTERNATIVE EMBODIMENTS

The compounds of formula (I) of the invention are characterised by the attachment of the alpha amino acid or esterase-hydrolysable alpha amino acid ester motif R$^1$R$^2$CHNH— to the ring containing A, B and D via a linker radical —YL$^1$X$^1$—[CH$_2$]$_z$—. Instead of being N-linked in this way, the alpha amino acid or esterase-hydrolysable alpha amino acid ester motif may be C-linked to the ring containing A, B and D via a linker radical attached to its alpha carbon. Thus, an alternative embodiment of the invention comprises compounds of formula (II) and salts, N-oxides, hydrates and solvates thereof:

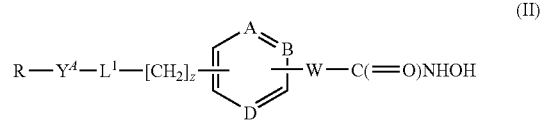

wherein A, B, D, W, L$^1$ and z are as defined and discussed above in relation to compounds of formula (I)

Y$^A$ is a bond, —(C=O)—, —S(O$_2$)—, —(C=O)NR$_3$—, —NR$_3$(C=O)—, —S(O$_2$)NR$_3$—, —NR$_3$S(O$_2$)—, or —NR$_3$(C=O)NR$_5$—, wherein R$_3$ and R$_5$ are as defined and discussed above in relation to compounds of formula (I); and R is a radical of formula (X) or (Y)

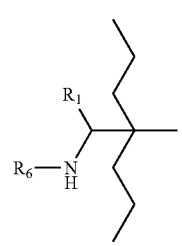

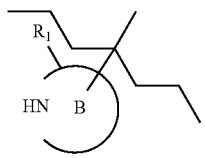
(Y)

wherein $R_1$ as defined and discussed above in relation to compounds of formula (I), and $R_6$ is hydrogen; or optionally substituted $C_1$-$C_6$ alkyl, $C_3$-$C_7$ cycloalkyl, aryl or heteroaryl or —(C=O)$R_3$, —(C=O)O$R_3$, or —(C=O)N$R_3$ wherein $R_3$ is as defined and discussed above in relation to compounds of formula (I).

In compounds (II), when the nitrogen of the ester motif is substituted but not directly bonded to a carbonyl i.e. when in formula X, $R_6$ is not H, or a group linked to the nitrogen through a —C(=O)—, —C(=O)O— or —C(=O)N$R_3$— radical, or in formula Y the ring system does not directly link a —C(=O), —C(=O)O— or —C(=O)NH— radical to the nitrogen of the esterase motif, the ester will only be hydrolysed by hCE-1 and hence the inhibitors will only accumulate in macrophages.

$R_6$ may be, inter alia, optionally substituted $C_1$-$C_6$ alkyl, $C_3$-$C_7$ cycloalkyl, aryl or heteroaryl, for example methyl, ethyl, n- or isopropyl, cyclopropyl, cyclopentyl, cyclohexyl, phenyl, or pyridyl. In cases where macrophage specificity is not required, $R_6$ may be hydrogen, or —(C=O)$R_7$, wherein $R_7$ is optionally substituted $C_1$-$C_6$ alkyl such as methyl, ethyl, n- or isopropyl, or n-, iso- or sec-butyl, $C_3$-$C_7$ cycloalkyl such as cyclopropyl, cyclopentyl, cyclohexyl, phenyl, pyridyl, thienyl, phenyl($C_1$-$C_6$ alkyl)-, thienyl($C_1$-$C_6$ alkyl)- or pyridyl($C_1$-$C_6$ alkyl)- such as benzyl, 4-methoxyphenylmethylcarbonyl, thienylmethyl or pyridylmethyl.

$R_6$ may also be, for example —(C=O)O$R_7$, or —(C=O)NH$R_7$ wherein $R_7$ is hydrogen or optionally substituted ($C_1$-$C_6$)alkyl such as methyl, ethyl, or n- or iso-propyl.

For compounds (II) which are to be administered systemically, esters with a slow rate of esterase cleavage are preferred, since they are less susceptible to pre-systemic metabolism. Their ability to reach their target tissue intact is therefore increased, and the ester can be converted inside the cells of the target tissue into the acid product. However, for local administration, where the ester is either directly applied to the target tissue or directed there by, for example, inhalation, it will often be desirable that the ester has a rapid rate of esterase cleavage, to minimise systemic exposure and consequent unwanted side effects. If a carbon atom to which the group R in formula (II) is attached is unsubstituted, ie R is attached to a methylene (—$CH_2$—) radical, then the esters tend to be cleaved more rapidly than if that carbon is substituted, or is part of a ring system such as a phenyl or cyclohexyl ring.

For compounds of the invention which are to be administered systemically, esters with a slow rate of carboxylesterase cleavage are preferred, since they are less susceptible to pre-systemic metabolism. Their ability to reach their target tissue intact is therefore increased, and the ester can be converted inside the cells of the target tissue into the acid product. However, for local administration, where the ester is either directly applied to the target tissue or directed there by, for example, inhalation, it will often be desirable that the ester has a rapid rate of esterase cleavage, to minimise systemic exposure and consequent unwanted side effects. In the compounds of this invention, if the carbon adjacent to the alpha carbon of the alpha amino acid ester ester is monosubstituted, ie $R_2$ is $CH_2R^z$ ($R^z$ being the mono-substituent) then the esters tend to be cleaved more rapidly than if that carbon is di- or tri-substituted, as in the case where $R_2$ is, for example, phenyl or cyclohexyl.

Utilities

As mentioned above, the compounds with which the invention is concerned are inhibitors of HDAC activity, and are therefore of use in the treatment of diseases such as cancers, psoriasis, inflammatory bowel disease, Crohns disease, ulcerative colitis, chronic obstructive pulmonary disease, asthma, multiple sclerosis, diabetes, atopic dermatitis, graft versus host disease, or systemic lupus erythematosus and rheumatoid arthritis.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial. However, it is expected that a typical dose will be in the range from about 0.001 to 50 mg per kg of body weight.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the drug may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®), Rotadisk®, Turbohaler® or the inhalers for example as described in European Patent Application EP 0 505 321).

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agent can be dissolved in the vehicle.

Synthesis

There are multiple synthetic strategies for the synthesis of the compounds with which the present invention is concerned, but all rely on known chemistry, known to the synthetic organic chemist. Thus, compounds according to the invention can be synthesised according to procedures described in the standard literature and are well-known to the one skilled in the art. Typical literature sources are "*Advanced organic chemistry*", 4$^{th}$ Edition (Wiley), J March; "*Comprehensive Organic Transformation*", 2$^{nd}$ Edition (Wiley), R. C. Larock; "*Handbook of Heterocyclic Chemistry*", 2$^{nd}$ Edition (Pergamon), A. R. Katritzky; review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*". The synthetic routes used in the preparation of the compounds of the Examples below may be adapted for the preparation of analogous compounds.

The following Examples illustrate the preparation of specific compounds of the invention, and the HDAC inhibitory properties thereof:

Abbreviations

MeOH=methanol
EtOH=ethanol
EtOAc=ethyl acetate
Boc=tert-butoxycarbonyl
DCM=dichloromethane
DMF=dimethylformamide
DCE=1,2-dichloroethane
TMSOK=potassium trimethylsilanoside
DMSO=dimethyl sulfoxide
TFA=trifluoroacetic acid
THF=tetrahydrofuran
Na$_2$CO$_3$=sodium carbonate
K$_2$CO$_3$=potassium carbonate
HCl=hydrochloric acid
aq=aqueous solution
sat=saturated
DIPEA=diisopropylethylamine
NaH=sodium hydride
NaOH=sodium hydroxide
STAB=sodium triacetoxyborohydride
NaCNBH$_3$=sodium cyanoborohydride
NaHCO$_3$=sodium hydrogen carbonate
Pd/C=palladium on carbon
TBME=tert-butyl methyl ether
TPAP=tetrapropyl ammonium perruthenate
(COCl)$_2$=oxalyl chloride
N$_2$=nitrogen
PyBop=benzotriazole-1-yl-oxy-tris-pyrrolidino-phosphonium hexafluorophosphate
Na$_2$SO$_4$=sodium sulphate
Et$_3$N=triethylamine
NH$_3$=ammonia
TMSCl=trimethylchlorosilane
NH$_4$Cl=ammonium chloride
LiAlH$_4$=lithium aluminium hydride
PyBrOP=Bromo-tris-pyrrolidino phosphoniumhexafluorophosphate
MgSO$_4$=magnesium sulfate
"BuLi=n-butyllithium
CO$_2$=carbon dioxide
EDCI=N-(3-Dimethylaminopropyl)-N'-ethylcarbodiimide hydrochloride
Et$_2$O=diethyl ether
LiOH=lithium hydroxide
HOBt=1-hydroxybenzotriazole
TLC=thin layer chromatography
LCMS=liquid chromatography/mass spectrometry
mL=millilitre(s)
g=gram(s)
mg=milligram(s)
mol=mole(s)
mmol=millimole(s)
HPLC=high performance liquid chromatography
NMR=nuclear magnetic resonance
RT=room temperature
h=hour(s)

Scaffold Intermediates

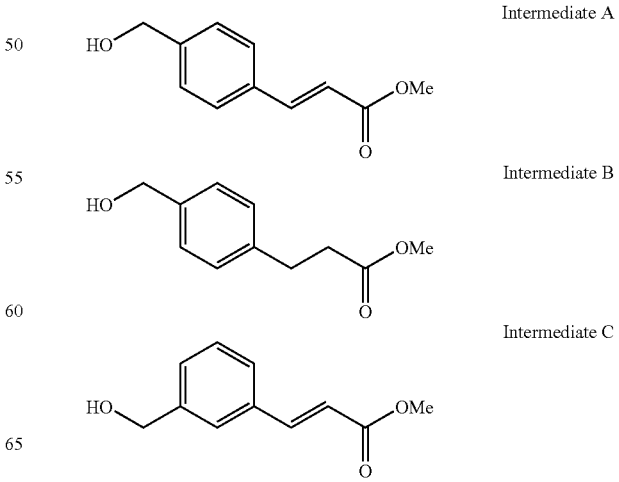

Intermediate A

Intermediate B

Intermediate C

-continued

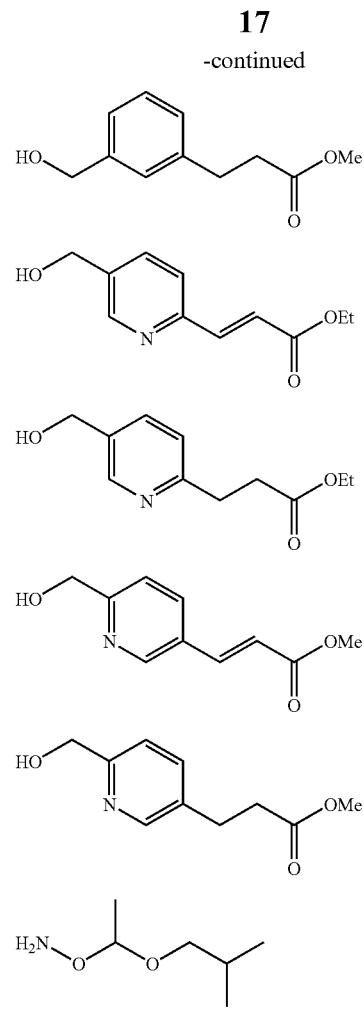

Intermediate D

Intermediate E

Intermediate F

Intermediate G

Intermediate H

Intermediate I

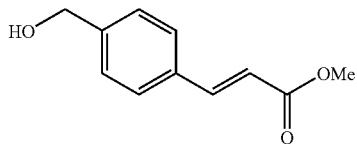

Preparation

Intermediate A

Methyl (2E)-3-[4-(hydroxymethyl)phenyl]acrylate

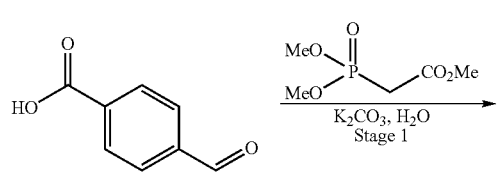

The title compound was prepared by the following methodology:

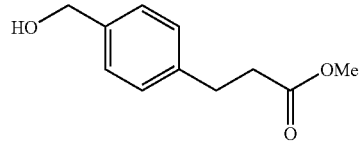

-continued

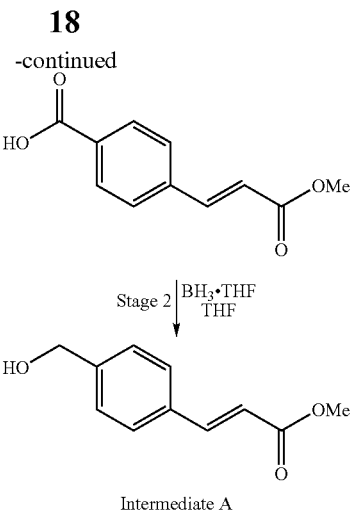

Intermediate A

Stage 1—Preparation of 4-[(1E)-3-methoxy-3-oxo-prop-1-en-1-yl]benzoic acid

4-Formylbenzoic acid (20 g, 0.133 mol) and $K_2CO_3$ (55 g, 0.398 mol) were added to water (350 mL) and cooled to 0-5° C. Trimethyl phosphonoacetate (26 mL, 0.160 mol) was charged dropwise maintaining the reaction temperature below 15° C. The reaction was then warmed and stirred at RT for 1.5 h before acidifying to pH~1. The resulting precipitate was filtered and dried in vacuo to afford the title product as a pale yellow solid (29.5 g, quant). $^1$H NMR (300 MHz, $d_6$-DMSO) δ: 7.89-7.52 (5H, m), 6.59 (1H, d, J=16.2 Hz), 3.7 (3H, s).

Stage 2—Preparation of methyl (2E)-3-[4-(hydroxymethyl)phenyl]acrylate (Intermediate A)

Stage 1 product (10 g, 48 mmol) was added to THF (80 mL) and cooled to 0-5° C. Borane-THF complex, 1M in THF (97 mL, 96 mmol) was added dropwise and the reaction allowed to warm to RT and stirred for 2 h. It was then quenched with 1:1 10% $HCl_{aq}$/THF, then the organics removed in vacuo. The residue was extracted with EtOAc (2×50 mL) and the combined organics washed with sat. $NaHCO_3$ solution (50 mL) then brine (50 mL), dried ($MgSO_4$) and concentrated in vacuo to afford the title product as a yellow oil (2.75 g, 30%). $^1$H NMR (300 MHz, $CD_3OD$) δ: 7.75-7.70 (5H, m), 6.54 (1H, d, J=16.2 Hz), 4.64 (2H, s), 3.80 (3H, s).

Intermediate B

Methyl 3-[4-(Hydroxymethyl)phenyl]propanoic acid

The title compound was prepared by the following methodology:

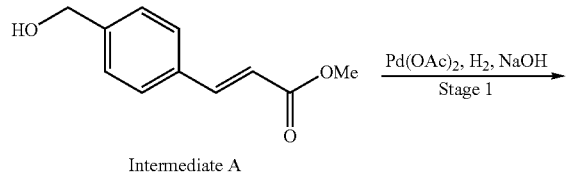

Intermediate A

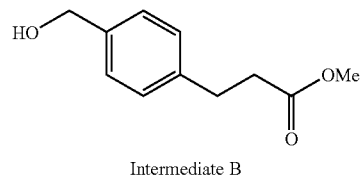

Intermediate B

Stage 1—Preparation of methyl 3-[4-(hydroxymethyl)phenyl]propanoic acid (Intermediate B)

Intermediate A (3 g, 15.6 mmol) and palladium acetate (0.3 g, 1.3 mmol) were added to 0.5N NaOH$_{aq}$ (50 mL), purged with and stirred under hydrogen for 4.5 h. The reaction was filtered through celite, washed with DCM (30 mL), acidified to pH~1 with 10% HCl$_{aq}$ and extracted with EtOAc (2×30 mL). The combined organics were dried (MgSO$_4$) and concentrated in vacuo to afford the title product as a pale yellow solid (2.85 g, 94%). $^1$H NMR (300 MHz, CD$_3$OD) δ: 7.25 (4H, ABq, J=10.9, 22.9 Hz), 4.57 (2H, s), 3.68 (3H, s), 2.92 (2H, t, J=9.8 Hz), 2.60 (2H, t, J=9.8 Hz).

Intermediate C

Methyl (2E)-3-[3-(hydroxymethyl)phenyl]acrylic acid

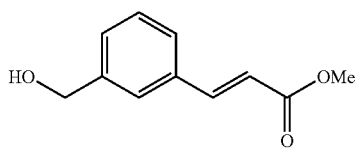 [SMILES: COC(=O)/C=C/c1cccc(CO)c1]

The title compound was prepared from 3-formylbenzoic acid by the same methodology used to make Intermediate A.
$^1$H NMR (300 MHz, CDCl$_3$) δ: 7.63 (1H, d, J=15.9 Hz), 7.42 (2H, d, J=8.4 Hz), 7.30 (2H, d, J=8.1 Hz), 6.37 (1H, d, J=15.9 Hz), 4.61 (2H, s), 3.77 (3H, s).

Intermediate D

Methyl 3-[3-(Hydroxymethyl)phenyl]propanoic acid

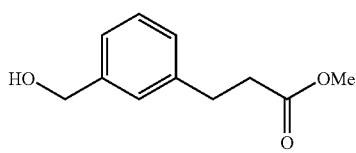 [SMILES: COC(=O)CCc1cccc(CO)c1]

The title compound was prepared from Intermediate C by the same methodology used to make Intermediate B.
$^1$H NMR (300 MHz, d$_6$-DMSO) δ: 6.73-7.25 (4H, m), 5.13 (1H, t, J=5.7 Hz), 4.76 (2H, d, J=5.7 Hz), 3.60 (3H, m), 2.84 (2H, t, J=7.5 Hz), 2.62 (2H, m, J=7.5 Hz).

Intermediate E

Ethyl (2E)-3-[5-(Hydroxymethyl)pyridin-2-yl]acrylic acid

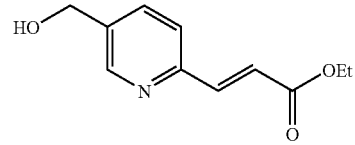 [SMILES: CCOC(=O)/C=C/c1ccc(CO)cn1]

The title compound was prepared by the following methodology:

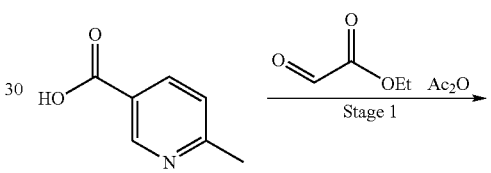

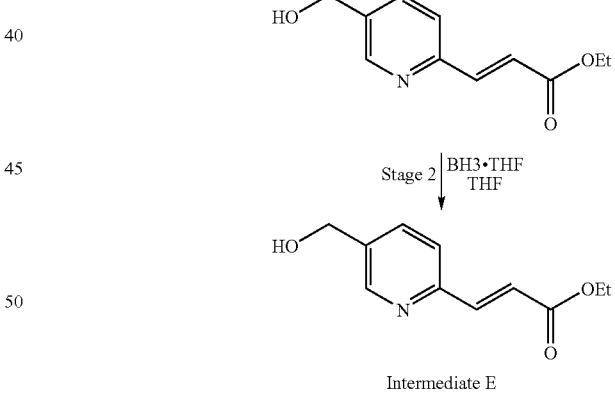

Intermediate E

Stage 1—Preparation of 6-[(1E)-3-ethoxy-3-oxo-prop-1-en-1-yl]nicotinic acid

6-Methylnicotinic acid (5 g, 36 mmol) and ethyl glyoxalate (50% solution in toluene ~8.7 mL, 44 mmol) were added to Ac$_2$O (25 mL) and stirred under a nitrogen atmosphere. The reaction was heated at 130° C. for 3 h then allowed to cool to RT over 17 h. The reaction was then quenched with water (10 mL) and concentrated to dryness in vacuo to afford the product as a brown solid (11.6 g, >100%). m/z=222 [M+H]$^+$.

Stage 2—Preparation of ethyl (2E)-3-[5-(hydroxymethyl)pyridin-2-yl]acrylate (Intermediate E)

Borane-THF complex (1M in THF –84 mL, 0.084 mol) was added dropwise to a slurry of stage 1 product (11.6 g, 52 mmol) in THF (100 mL), under a nitrogen atmosphere. The reaction was stirred at RT for 1.5 h then quenched with 2N HCl$_{aq}$ (20 mL). The THF was removed in vacuo, the residue basified to pH~9 with K$_2$CO$_3$ then extracted with EtOAc (3×30 mL). The organic phases were combined, dried (MgSO$_4$) then concentrated in vacuo to afford the crude product as a brown oil. Purification by column chromatography gave the desired product as a yellow solid (1.86 g, 25%). $^1$H NMR (300 MHz, CD$_3$OD) δ: 8.59 (1H, s), 7.91-7.63 (3H, m), 6.88 (1H, d, J=15.9 Hz), 4.70 (2H, s), 4.28 (2H, q), 1.35 (3H, t).

Intermediate F

Ethyl 3-[5-(Hydroxymethyl)pyridin-2-yl]propanoic acid

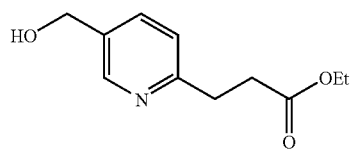 [SMILES: CCOC(=O)CCc1ccc(CO)cn1]

The title compound was prepared from Intermediate E by the same methodology used to make Intermediate B.

$^1$H NMR (300 MHz, CDCl$_3$) δ: 8.49 (1H, s), 7.65 (1H, d, J=5.7 Hz), 7.21 (1H, d, J=7.8 Hz), 4.68 (2H, s), 4.13 (2H, q, J=7.2 Hz), 3.12 (2H, t, J=7.5 Hz), 2.77 (2H, t, J=7.2 Hz), 1.24 (3H, t, J=7.2 Hz).

Intermediate G

Methyl (2E)-3-[6-(Hydroxymethyl)pyridin-3-yl]acrylic acid

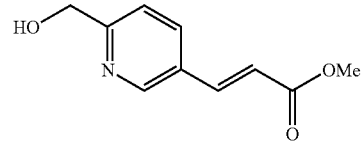 [SMILES: COC(=O)/C=C/c1ccc(CO)nc1]

The title compound was prepared by the following methodology:

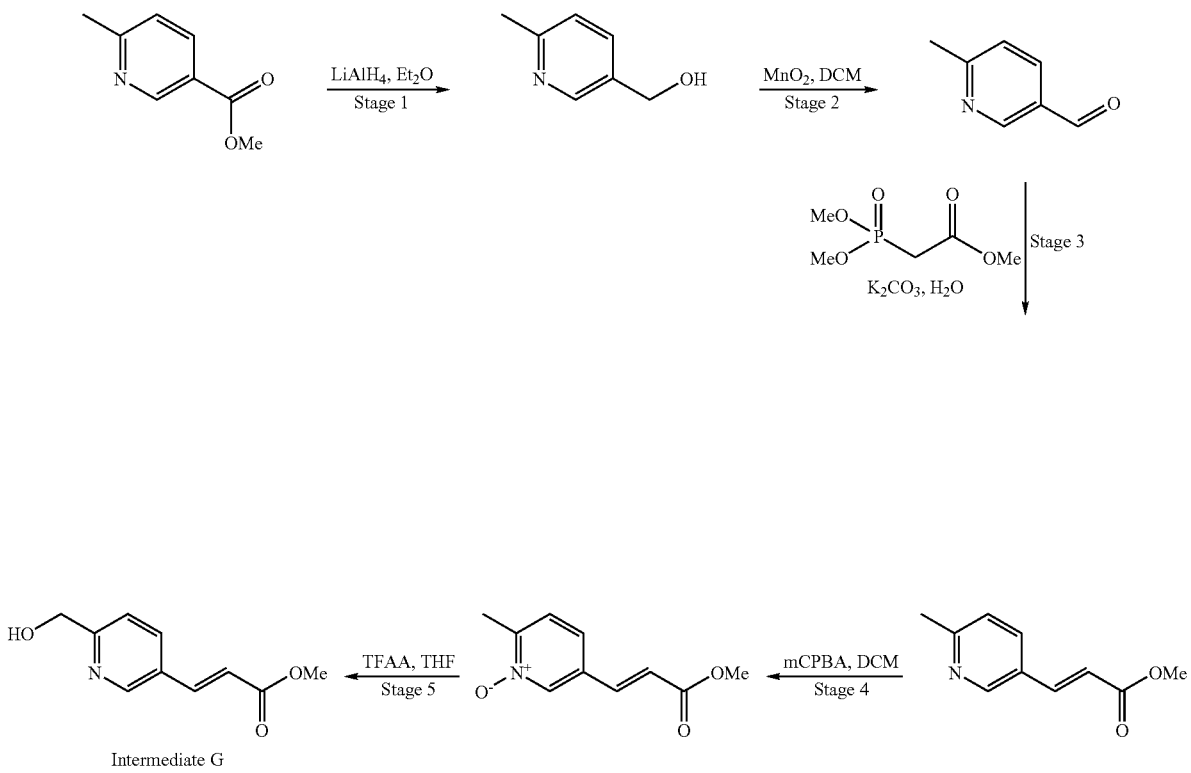

Stage 1—Preparation of (6-methylpyridin-3-yl)methanol

To a suspension of lithium aluminium hydride (7.24 g, 191 mmol) in Et$_2$O (400 ml) at −78° C. was added via cannula over a period of one hour a solution of methyl 6-methylnicotinate (19.62 g, 130 mmol) in Et$_2$O (200 mL). Once addition was completed, the mixture was stirred for a further 3 h. Excess lithium aluminium hydride was quenched by dropwise addition of EtOAc (40 ml). The mixture was then warmed using a water-ice bath, and further quenched with sat NH$_4$Cl (500 mL). The ethereal layer was decanted, and EtOAc was added (500 mL). The mixture was stirred vigorously, and the organic layer was again decanted. The extraction procedure was repeated twice (500 mL EtOAc). The combined organic extracts were dried (MgSO$_4$) and concentrated to yield the desired product (13.6 g, 85%). $^1$H NMR (300 MHz, CDCl$_3$) δ: 8.39 (1H, s), 7.62 (1H, dd, J=2.1, 8.1 Hz), 7.14 (1H, d, J=7.8 Hz), 4.68 (2H, s), 2.54 (3H, s).

Stage 2—Preparation of 6-methylnicotinaldehyde

To a cooled (ice bath) solution of stage 1 product (14.85 g, 120.6 mmol) in DCM (1000 mL) was added manganese oxide (100 g) in 10 g portions over a period of 30 minutes. The mixture was warmed to RT and stirred for 45 minutes and was then filtered through Celite. The residues were washed with DCM (500 mL), and the combined DCM portions were concentrated to yield the desired product. $^1$H NMR (300 MHz, CDCl$_3$) δ: 10.00 (1H, s), 8.88 (1H, d, J=1.8 Hz), 8.00 (1H, dd, J=2.4, 8.1 Hz), 7.26 (1H, d, J=8.1 Hz), 2.60 (3H, s).

Stage 3—Preparation of methyl (2E)-3-(6-methylpyridin-3-yl)acrylate

To a solution of stage 2 product (14.60 g, 120 mmol) in water (600 mL) was added K$_2$CO$_3$ (55 g, 398 mmol). The mixture was cooled (ice bath) and trimethylphosphonoacetate (25 mL, 154 mmol) was added dropwise over a period of 10 minutes. The mixture was stirred for 5 minutes and then warmed to RT and stirred for a further hour. The product was collected by filtration and washed with water (250 mL), then dried under vacuum to yield the desired product (15.708 g, 73% over two steps). $^1$H NMR (300 MHz, d$_6$-DMSO) δ: 8.74 (1H, d, J=2.1 Hz), 8.08 (1H, dd, J=2.4, 8.1 Hz), 7.66 (1H, d, J=16.2 Hz), 7.32 (1H, d, J=8.1 Hz), 6.74 (1H, d, J=16.2 Hz), 3.73 (3H, s), 2.50 (3H, s).

Stage 4—Preparation of methyl (2E)-3-(6-methyl-1-oxidopyridin-3-yl)acrylate

To a solution of stage 3 product (10.04 g, 57 mmol) in DCM (250 mL) was added mCPBA (10.1 g, 10.7 g, 4.7 g, 147 mmol) in three portions over a period of 1 hour. The mixture was dried by addition of anhydrous magnesium sulfate, and filtered, washing with a further portion of DCM (200 mL). The mixture was concentrated, then loaded directly onto a silica gel column and eluted with 10% methanol-DCM to yield the desired product (10.35 g, 94%). $^1$H NMR (300 MHz, d$_6$-DMSO) δ: 8.70 (1H, s), 7.68 (1H, dd, J=1.3, 7.9 Hz), 7.59 (1H, d, J=16.2 Hz), 7.52 (1H, d, J=8.1 Hz), 3.74 (3H, s), 2.34 (3H, s).

Stage 5—Preparation of methyl (2E)-3-[6-(hydroxymethyl)pyridin-3-yl]acrylate (Intermediate G)

To a cooled (ice bath) solution of stage 4 product (24.60 g, 127 mmol) in THF (500 mL) was added trifluoroacetic anhydride (25 mL, 180 mmol). The mixture was stirred for 15 minutes and then warmed to RT. After stirring for 1 hour, the solution was cooled (ice bath) and the mixture was quenched by careful addition of sat NaHCO$_3$ (1000 mL). The product was extracted with DCM (3×500 mL) then purified by flash column chromatography (10% MeOH in DCM) to yield the desired product (13.97 g, 57%). $^1$H NMR (300 MHz, CDCl$_3$) δ: 8.70 (1H, s), 7.87 (1H, dd, J=2.1, 8.1 Hz), 7.71 (1H, d, J=16.2 Hz), 7.32 (1H, d, J=8.1 Hz), 8.52 (1H, d, J=15.9 Hz), 4.81 (2H, s), 3.85 (3H, s).

Intermediate H

Methyl 3-[6-(Hydroxymethyl)pyridin-3-yl]propanoic acid

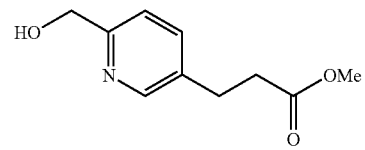 [SMILES: COC(=O)CCc1ccc(CO)nc1]

The title compound was prepared from Intermediate G acid by the same methodology used to make Intermediate B.
$^1$H NMR (300 MHz, CDCl$_3$) δ: 8.44 (1H, s), 7.55 (1H, dd, J=2.1, 8.1 Hz), 7.20 (1H, d, J=8.1 Hz), 4.75 (2H, s), 3.69 (3H, s), 2.98 (2H, t, J=7.5 Hz), 2.67 (2H, t, J=7.5 Hz).

Intermediate I

O-(1-Isobutoxyethyl)hydroxylamine

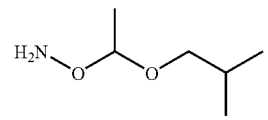

The title compound was prepared by the following methodology:

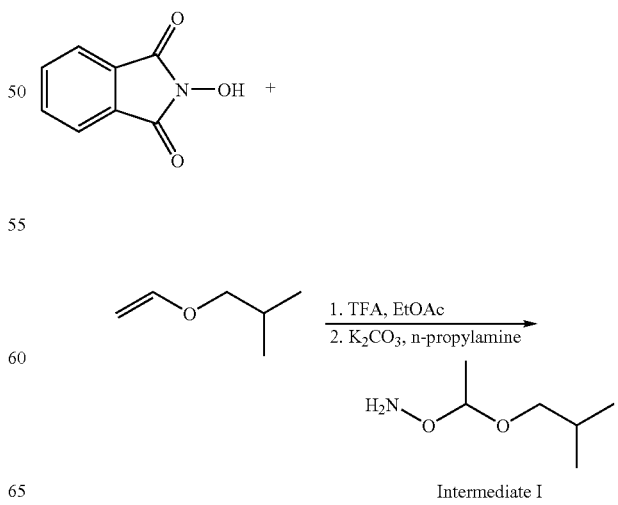

Intermediate I

Intermediate I was prepared following the methodology described in WO 01/60785.

$^1$H NMR (300 MHz, $d_6$-DMSO) δ: 0.85 (6H, d), 1.15 (3H, d), 1.75 (1H, m), 3.18 (1H, dd), 3.42 (1H, dd), 4.53 (1H, q), 5.82 (2H, s).

Aminoacid Intermediates

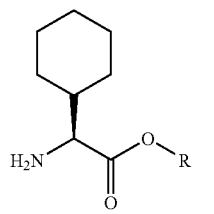
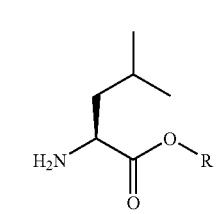

Int. J1 R = cyclopentyl
Int. J2 R = t-butyl
Int. J3 R = ethyl
Int. J4 R = allyl
Int. J5 R = 2-methylcyclopentyl
Int. J6 R = indanyl
Int. J7 R = norbonyl
Int. J8 R = 3-methylcyclopentyl
Int. J9 R = benzyl
Int. J10 R = ethylmorpholino
Int. J11 R = ethyldimethylamino
Int. J12 R = (+)-menthyl
Int. J13 R = (-)-menthyl Int. K1 R = cyclopentyl
Int. K2 R = t-butyl
Int. K3 R = ethylmorpholino
Int. K4 R = norbonyl
Int. K5 R = indanyl
Int. K6 R = ethyldimethylamino
Int. K7 R = (-)-menthyl

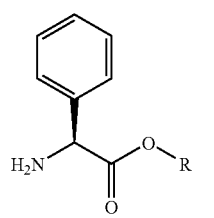
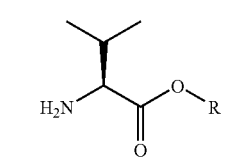

Intermediate L1 R = cyclopentyl
Intermediate L2 R = t-butyl

Intermediate M1 R = cyclopentyl
Intermediate M2 R = t-butyl

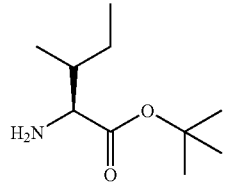
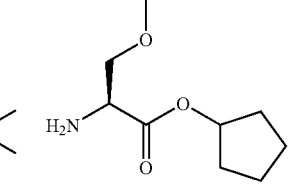

Intermediate N

Intermediate O

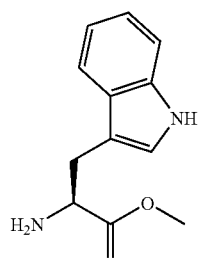
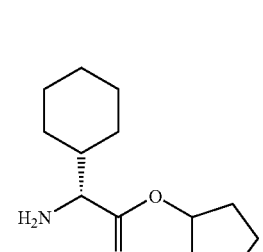

Intermediate P

Intermediate Q

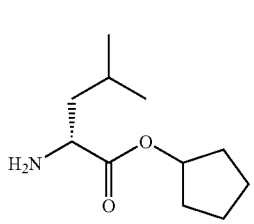
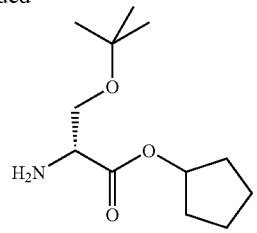

Intermediate R

Intermediate S

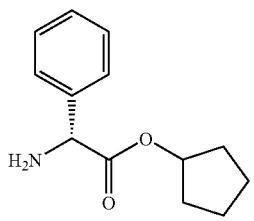
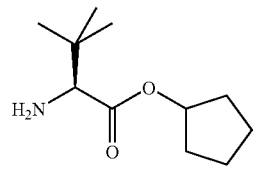

Intermediate T

Intermediate U

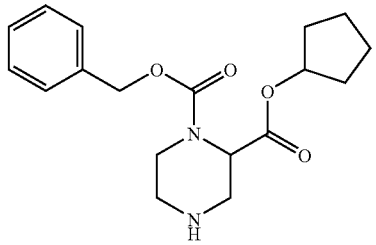

Intermediate V

Preparation

The intermediates above were prepared from the corresponding aminoacids and alcohols according to the methods described below:

Method I.

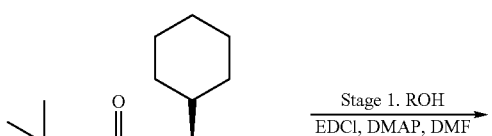

Stage 1. ROH
EDCl, DMAP, DMF

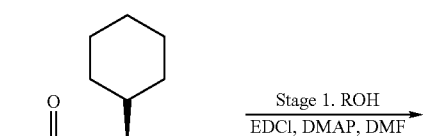

Stage 2.
HCl/dioxane
DCM

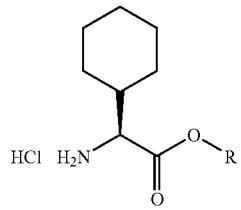

-continued
Method II.

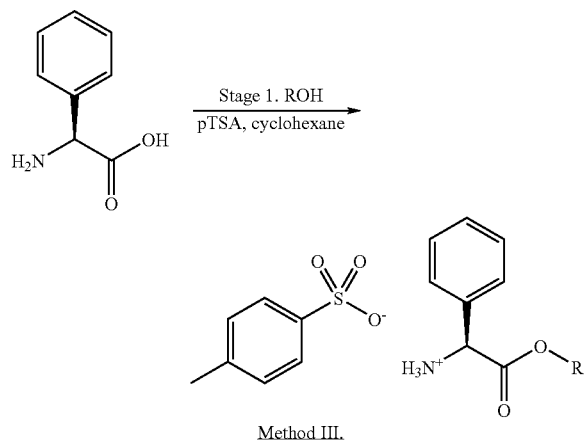

Method III.

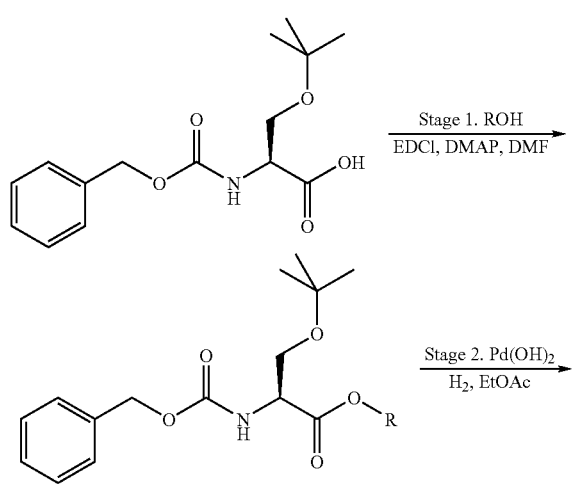

Method I (Exemplified for Intermediate J1)

Stage 1—Preparation of cyclopentyl (2S)-[(tert-butoxycarbonyl)amino](cyclohexyl)acetate To a solution of (S)-2-tert-butoxycarbonylamino-3-cyclohexyl-propionic acid (5 g, 19.4 mmol) in DMF (50 mL) at 0° C. was added cyclopentanol (8.8 ml, 97.15 mmol), EDC (4.09 g, 21.37 mmol) and finally DMAP (237 mg, 1.94 mmol). The reaction mixture was warmed to RT and stirred for 18 h. The DMF was removed in vacuo to give a clear oil. This was separated between water and EtOAc. The organic phase was dried (MgSO$_4$) and concentrated in vacuo. The crude extract was purified by column chromatography (25% EtOAC in heptane) to yield the desired product as a clear oil (14.87 g, 55%). $^1$H NMR (300 MHz, d$_6$-DMSO) δ: 7.09 (1H, d), 5.08 (1H, t), 3.76 (1H, t), 1.50-1.85 (10H, br m), 1.39 (9H, s), 1.00-1.25 (9H, br m).

Stage 2—Preparation of cyclopentyl (2S)-amino(cyclohexyl)acetate hydrochloride Intermediate J1

Stage 1 product (14.87 g, 45.69 mmol) was dissolved in DCM (100 mL) and treated with 4M HCl/dioxane (22.8 mL, 91.38 mmol) and the reaction mixture was stirred at RT for 24 h. The crude mixture was concentrated under reduced pressure to give an orange oil. This was triturated with Et$_2$O to give a white precipitate. This was further washed with Et$_2$O to give the desired product as a white powder (7.78 g, 65%). $^1$H NMR (300 MHz, d$_6$-DMSO) δ: 8.45 (3H, br s), 5.22 (1H, t), 3.28 (1H, d), 1.95-1.50 (10H, br m), 1.30-0.90 (9H, br m).

Method II (Exemplified for Intermediate L1)

Stage 1—Ester Formation to Yield cyclopentyl (2S)-amino(phenyl)acetate Tosylate Salt (Intermediate L1)

To a slurry of (S)-phenylglycine (5 g, 33.1 mmol) in cyclohexane (150 mL) was added cyclopentanol (29.84 mL, 331 mmol) and p-toluene sulfonic acid (6.92 g, 36.4 mmol). The reaction was fitted with a Dean-Stark receiver and heated to 135° C. for complete dissolution. After 12 h, the reaction was cooled to RT leading to the precipitation of a white solid. The solid was filtered and washed with EtOAc before drying under reduced pressure to give the required product as a white powder (11.01 g, 85%). $^1$H NMR (300 MHz, d$_6$-DMSO) δ: 8.82 (2H, br s), 8.73 (1H, br s), 7.47 (7H, m), 7.11 (2H, d), 5.25 (1H, br s), 5.18 (1H, m), 2.29 (3H, s), 1.87-1.36 (8H, m).

Method III (Exemplified for Intermediate O)

Stage 1—Preparation of [(2S)-2-{[(benzyloxy)carbonyl]amino}-3-tert-butoxypropanoyl]oxy To a solution of (S)-2-benzyloxycarbonylamino-3-tert-butoxy-propionic acid (25 g, 84.65 mmol) in DMF (250 mL) at 0° C. was added cyclopentanol (15.36 mL, 169.3 mmol), EDCI (17.85 g, 93.11 mmol) and finally DMAP (1.03 g, 8.46 mmol). The reaction mixture was warmed to RT and stirred for 18 h. The DMF was removed in vacuo to give a yellow oil. This was partitioned between water and EtOAc. The organic phase was dried (MgSO$_4$) and concentrated in vacuo. The crude extract was purified by column chromatography (25% EtOAC in heptane) to yield the desired product as a clear oil. This was used directly in the next stage without characterization.

Stage 2—Preparation of cyclopentyl O-tert-butyl-L-serinate (Intermediate O)

Stage 1 product was dissolved in EtOAc (150 mL), treated with Pd(OH)$_2$ (10 mol %) and stirred under an atmosphere of hydrogen for 32 h. Upon completion, the catalyst was removed by filtration through celite and the filtrate concentrated in vacuo to yield the desired product as a clear oil (15.96 g, 82% over two steps). $^1$H NMR (300 MHz, d$_6$-DMSO)o: 5.17 (1H, t), 3.45 (1H, m), 3.34 (2H, q), 1.90-1.50 (9H, br m), 1.08 (9H, s).

Characterisation:

| Intermediate number | Chemical name | Method for preparation | Analytical data |
|---|---|---|---|
| J1 | Cyclopentyl (2S)-amino(cyclohexyl)acetate | I | $^1$H NMR (300 MHz, d$_6$-DMSO) δ: 8.45 (3H, br s), 5.22 (1H, t), 3.28 (1H, d), 1.95-1.50 (10H, br m), 1.30-0.90 (9H, br m). |
| J2 | tert-Butyl (2S)-amino(cyclohexyl)acetate | I | m/z = 214 [M + H]$^+$. |
| J3 | Ethyl (2S)-amino(cyclohexyl)acetate | I | $^1$H NMR (300 MHz, d$_6$-DMSO) δ: 3.99-4.35 (3H, m), 1.02-1.86 (12H, m), 1.06 (3H, t, J = 7.2 Hz). |
| J4 | Allyl (2S)-amino(cyclohexyl)acetate | I | $^1$H NMR (300 MHz, d$_6$-DMSO) δ: 5.92 (1H, ddd, J = 5.4, 10.5, 17.4 Hz), 5.34 (1H, dd, J = 1.8, 17.4 Hz), 5.22 (1H, dd, J = 3.0, 10.5 Hz), 4.51-4.62 (2H, m), 3.12 (1H, d, J = 5.7 Hz), 0.95-1.70 (11H, m). |
| J5 | 2-Methylcyclopentyl (2S)-amino(cyclohexyl)acetate | I | $^1$H NMR (300 MHz, d$_6$-DMSO) δ: 4.61 (1H, d, J = 6.0 Hz), 3.06 (1H, d, J = 2.4 Hz), 1.00-2.01 (20H, m), 0.90 (3H, d, J = 5.7 Hz). |
| J6 | 2,3-Dihydro-1H-inden-2-yl (2S)-amino(cyclohexyl)acetate | I | m/z = 274.25 [M + H]$^+$ |
| J7 | Bicyclo[2.2.1]hept-2-yl (2S)-amino(cyclohexyl)acetate | I | $^1$H NMR (300 MHz, d$_6$-DMSO) δ: 4.86 (1H, t, J = 3.6 Hz), 3.03 (1H, d, J = 3.9 Hz), 2.22 (2H, m), 0.93-1.70 (21H, m). |
| J8 | 3-Methylcyclopentyl (2S)-amino(cyclohexyl)acetate | I | $^1$H NMR (300 MHz, d$_6$-DMSO) δ: 5.02-5.11 (1H, m), 3.02-3.05 (1H, m), 0.80-2.20 (23H, m). |
| J9 | Benzyl (2S)-amino(cyclohexyl)acetate | I | $^1$H NMR (300 MHz, d$_6$-DMSO) δ: 7.23-7.43 (5H, m), 5.05-5.16 (2H, m), 3.15 (1H, t, J = 3.0 Hz), 1.42-1.80 (7H, m), 0.92-1.27 (5H, m). |
| J10 | 2-Morpholin-4-ylethyl (2S)-amino(cyclohexyl)acetate | I | $^1$H NMR (300 MHz, d$_6$-DMSO) δ: 8.71 (3H, br s), 4.47-4.62 (1H, m), 3.85-4.00 (6H, m), 3.42-3.55 (4H, m), 3.15-3.20 (2H, m), 1.60-1.85 (6H, m), 1.01-1.25 (5H, m). |
| J11 | 2-(Dimethylamino)ethyl (2S)-amino(cyclohexyl)acetate | I | $^1$H NMR (300 MHz, CDCl$_3$) δ: 4.20-4.29 (3H, m), 2.60 (2H, t, J = 6.0 Hz), 2.30 (6H, s), 1.52-1.80 (6H, m), 1.05-1.25 (5H, m). |
| J12 | (1S,2R,5S)-2-Isopropyl-5-methylcyclohexyl (2S)-amino(cyclohexyl)acetate | I | $^1$H NMR (300 MHz, d$_6$-DMSO) δ: 8.24 (3H, br s), 7.47 (2H, d, J = 7.8 Hz), 7.12 (2H, d, J = 7.8 Hz), 4.65-4.73 (1H, m), 3.94 (1H, br s), 2.29 (3H, s), 1.00-2.00 0.89 (6H, d, J = 6.3 Hz), 0.71 (3H, d, J = 6.6 Hz). |
| J13 | (1R,2S,5R)-2-Isopropyl-5-methylcyclohexyl (2S)-amino(cyclohexyl)acetate | I | m/z = 296 {M + H]$^+$. |
| K1 | Cyclopentyl L-leucinate | I | m/z = 200 [M + H]$^+$; $^1$H NMR (300 MHz, CDCl$_3$) δ: 0.90 (6H, t, J = 6.4 Hz), 1.23-1.94 (11H, m), 3.38 (1H, dd, J = 8.4, 5.9 Hz), 5.11-5.22 (1H, m). |
| K2 | tert-Butyl L-leucinate | Commercial source | n/a |
| K3 | 2-Morpholin-4-ylethyl L-leucinate | I | $^1$H NMR (300 MHz, d$_6$-DMSO) δ: 8.96 (2H, br s), 4.52 (1H, m), 3.97 (4H, br s), 3.59-3.41 (6H, m), 3.18 (2H, br s), 1.80-1.68 (3H, m), 0.88 (6H, br s). |
| K4 | Bicyclo[2.2.1]hept-2-yl L-leucinate | I | $^1$H NMR (300 MHz, d$_6$-DMSO) δ: 8.58 (2H, br s), 4.64 (1H, d, J = 7.6 Hz), 2.43 (1H, br s), 2.28 (2H, br s), 1.99 (1H, m), 1.79-1.02 (10H, m), 0.93-0.87 (6H, m). |
| K5 | 2,3-Dihydro-1H-inden-2-yl L-leucinate | I | $^1$H NMR (300 MHz, d$_6$-DMSO) δ: 8.72 (3H, br s), 7.25 (2H, br s), 7.18 (2H, br s), 5.55 (1H, br s), 3.80 (1H, br s), 3.33 (2H, dd, J = 6.5, 16.3 Hz), 2.99 (2H, t, J = 16.3 Hz), 1.72-1.55 (3H, m), 0.82 (6H, s). |
| K6 | 2-(Dimethylamino)ethyl L-leucinate | I | $^1$H NMR (300 MHz, CDCl$_3$) δ: 3.50-3.40 (2H, m), 2.94 (2H, s), 2.52 (2H, t, J = 5.4 Hz), 1.48 (1H, m), 1.35 (1H, m), 0.93-0.82 (12H, m). |
| K7 | (1R,2S,5R)-2-Isopropyl-5-methylcyclohexyl L-leucinate | I | $^1$H NMR (300 MHz, d$_6$-DMSO) δ: 8.58 (2H, br s), 4.70 (1H, dt, J = 5.4, 10.9 Hz), 3.91 (1H, t, J = 8.7 Hz), 1.92-1.82 (2H, m), 1.80-1.55 (5H, m), |

-continued

| Intermediate number | Chemical name | Method for preparation | Analytical data |
|---|---|---|---|
| | | | 1.46-1.35 (2H, m), 1.02 (2H, t, J = 10.9 Hz), 0.93-0.82 (13H, m), 0.70 (3H, d, J = 8.7 Hz). |
| L1 | Cyclopentyl (2S)-amino(phenyl)acetate | II | $^1$H NMR (300 MHz, d$_6$-DMSO) δ: 8.82 (2H, br s), 8.73 (1H, br s), 7.47 (7H, m), 7.11 (2H, d), 5.25 (1H, br s), 5.18 (1H, m), 2.29 (3H, s), 1.87-1.36 (8H, m). |
| L2 | tert-Butyl (2S)-amino(phenyl)acetate | Commercial source | n/a |
| M1 | Cyclopentyl L-valinate | I | m/z = 186 [M + H]$^+$; $^1$H NMR (300 MHz, d$_6$-DMSO) δ: 8.26 (1H, br s), 7.49 (2H, d, J = 8.1 Hz), 7.13 (2H, d, J = 8.1 Hz), 5.21 (1H, t, J = 5.5 Hz), 3.86 (1H, br s), 3.42 (1H, br s), 2.29 (3H, s), 2.13 (1H, td, J = 6.9, 4.7 Hz), 1.90-1.79 (2H, m), 1.70-1.57 (6H, m), 0.98 (3H, d, J = 7.0 Hz), 0.94 (3H, d, J = 7.0 Hz). |
| M2 | tert-Butyl L-valinate | Commercial source | n/a |
| N | tert-Butyl L-isoleucinate | Commercial source | n/a |
| O | Cyclopentyl O-tert-butyl-L-serinate | III | $^1$H NMR (300 MHz, d$_6$-DMSO) δ: 5.17 (1H, t), 3.45 (1H, m), 3.34 (2H, q), 1.90-1.50 (9H, br m), 1.08 (9H, s). |
| P | Methyl L-tryptophanate | Commercial source | n/a |
| Q | Cyclopentyl (2R)-amino(cyclohexyl)acetate | I | $^1$H NMR (300 MHz, CDCl$_3$) δ: 8.63 (3H, s), 5.22 (1H, m), 5.16 (1H, m), 2.08-0.90 (19H, m). |
| R | Cyclopentyl D-leucinate | I | $^1$H NMR (300 MHz, CDCl$_3$) δ: 8.90 (3H, s), 5.28 (1H, m), 3.97 (1H, m), 2.10-1.50 (11H, m), 1.01 (6H, d, J = 4.5 Hz). |
| S | Cyclopentyl O-tert-butyl-D-serinate | III | $^1$H NMR (300 MHz, CDCl$_3$) δ: 5.14 (1H, m), 3.50 (3H, m), 1.90-1.39 (8H, m), 1.09 (9H, s). |
| T | Cyclopentyl (2R)-amino(phenyl)acetate | II | $^1$H NMR (300 MHz, d$_6$-DMSO) δ: 8.80 (2H, br s), 8.74 (1H, br s), 7.44 (7H, m), 7.13 (2H, d), 5.28 (1H, br s), 5.21 (1H, m), 2.26 (3H, s), 1.85-1.30 (8H, m). |
| U | Cyclopentyl 3-methyl-L-valinate | I | m/z = 200 [M + H]$^+$; $^1$H NMR (300 MHz, d$_6$-DMSO) δ: 8.51 (3H, br s), 5.20 (1H, t, J = 5.7 Hz), 5.21-4.89 (1H, m), 3.63 (1H, s), 1.84 (2H, t, J = 5.6 Hz), 1.75-1.55 (6H, m), 1.00 (9H, s). |
| V | 1-Benzyl 2-cyclopentyl piperazine-1,2-dicarboxylate | I | $^1$H NMR (300 MHz, CDCl$_3$) δ: 7.40-7.29 (5H, m), 5.19 (2H, br s), 4.64-4.97 (2H, m), 4.07-3.85 (2H, m), 3.31 (1H, m), 3.08 (1H, m), 2.84 (1H, m), 2.06 (1H, s), 1.92-1.56 (8H, m), 1.27 (1H, t, J = 6.5 Hz). |

All the above intermediates were used in aminoacid coupling reactions as free bases. To an individual skilled in the art, it will be apparent that each free base can be prepared by titration of the salts described above with a suitable inorganic base (eg NaHCO$_3$).

Example 1

(2S)-[({3-[(1E)-3-(Hydroxyamino)-3-oxoprop-1-en-1-yl]phenyl}sulfonyl)amino](phenyl)acetate

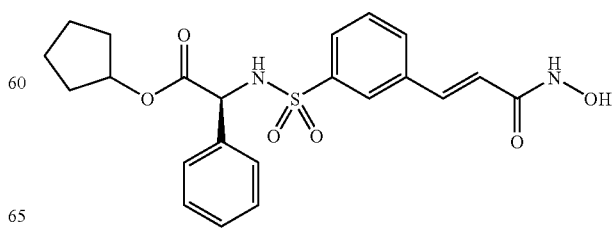

The title compound was prepared by the following methodology:

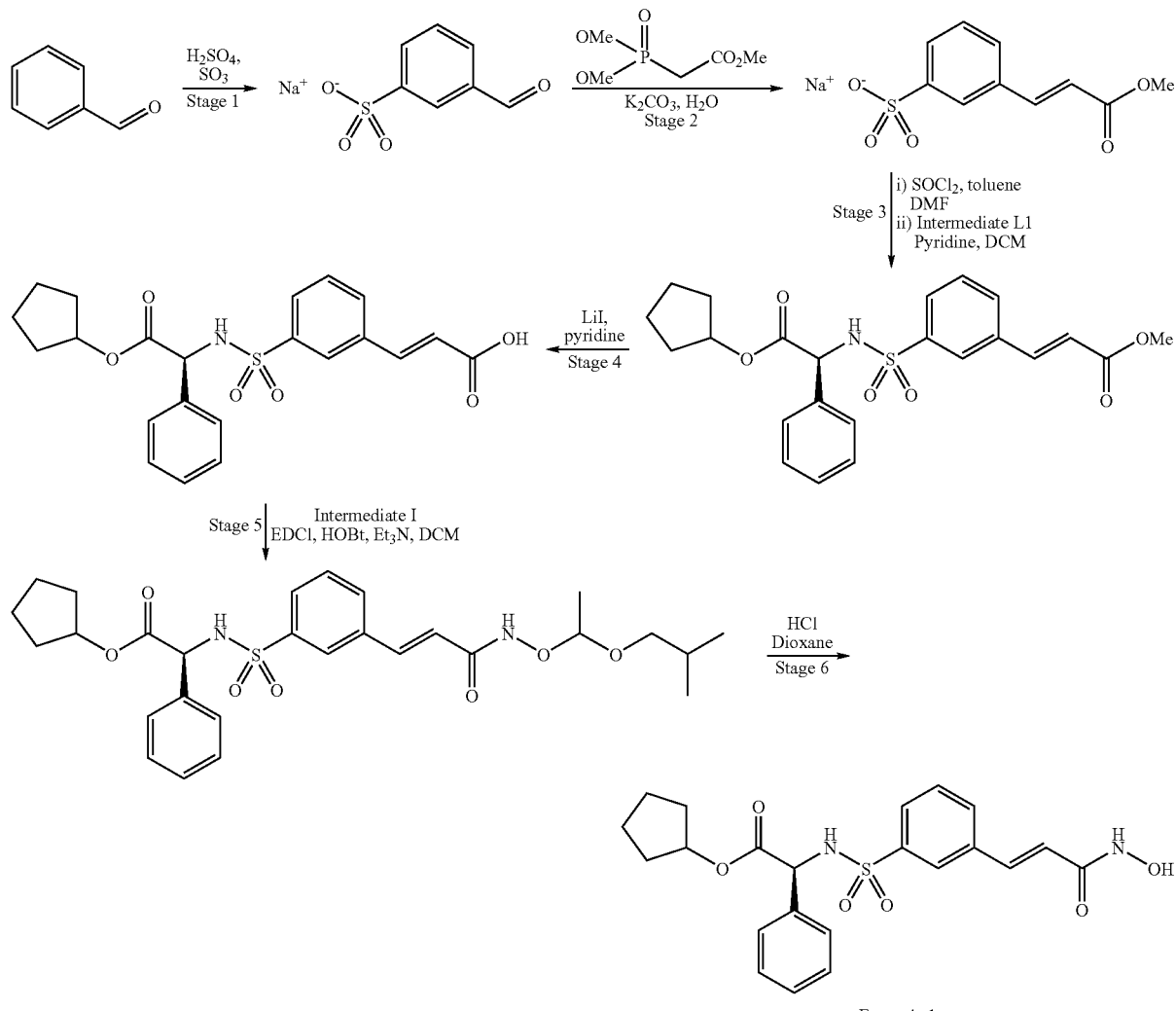

Example 1

Stage 1—Preparation of 3-Formylbenzenesulfonate Sodium Salt

Benzaldehyde (10 g, 94 mmol) was added dropwise to 20% sulfur trioxide in fuming sulfuric acid (25 mL) and stirred under an atmosphere of nitrogen, maintaining the reaction temperature below 40° C. The reaction was stirred at 40° C. for 18 h. The reaction was then quenched onto ice (60 g) and the aqueous extracted with EtOAc (100 mL). The aqueous phase was treated with $CaCO_3$ until the evolution of $CO_2$ ceased (pH~6). The resultant precipitate was filtered, washed with water and the filtrate basified with $Na_2CO_3$ to pH~8. The precipitate was removed by filtration and the filtrate evaporated to dryness in vacuo. The residue was washed with MeOH, filtered and the washings concentrated to give the desired product as a white solid (7.94 g, 81%). $^1$H NMR (300 MHz, $CD_3OD$) δ: 9.88 (1H, s), 8.19 (1H, s), 7.99 (2H, dd), 7.63 (1H, t, J=7.8 Hz).

Stage 2—Preparation of 3-[(1E)-3-methoxy-3-oxo-prop-1-en-1-yl]benzenesulfonate Sodium Salt Stage 1 product (13.8 g, 66 mmol) and $K_2CO_3$ (18.3 g, 132 mmol) were dissolved in water (70 mL). Trimethyl phosphonoacetate (14.51 g, 80 mmol) was added dropwise and the reaction stirred at RT for 15 h. The resulting precipitate was filtered, washed with MeOH and dried in vacuo to afford the desired product as a white solid (5.75 g, 33%). $^1$H NMR (300 MHz, $d_6$-DMSO) δ: 7.84 (1H, s), 7.65-7.70 (3H, m), 7.40 (1H, t, J=7.5 Hz), 6.60 (1H, d, J=16.2 Hz), 3.73 (1H, s).

Stage 3—Preparation of methyl (2E)-3-[3-({[(1S)-2-(cyclopentyloxy)-2-oxo-1-phenylethyl]amino}sulfonyl)phenyl]acrylate Stage 2 product (5.75 g, 22 mmol) was added to toluene (17.5 mL) and DMF (6 drops) under an atmosphere of nitrogen. Thionyl chloride (4.75 mL, 66 mmol) was added dropwise then the reaction heated at reflux for 1 h. This was then concentrated to dryness and the residue was dissolved in toluene (50 mL), filtered and the filtrate concentrated to dryness to afford a yellow solid. This was dissolved in DCM (7 mL) and added to a solution of Intermediate L1 (1.91 g, 4.9 mmol) in pyridine (2.5 mL) and DCM (10 mL). The reaction was stirred for 2 h at RT and then concentrated to dryness in vacuo and the residue separated between EtOAc (50 mL) and 10% $HCl_{aq}$ (50 mL). The organic phase was washed with water (50 mL), saturated $NaHCO_3$ (50 mL) and brine (50 mL) then dried ($MgSO_4$) and concentrated in vacuo to afford the product as a yellow oil (1.77 g, 54%). m/z=442 [M−H]⁻.

Stage 4—Preparation of (2E)-3-[3-({[(1S)-2-(cyclopentyloxy)-2-oxo-1-phenylethyl]amino}sulfonyl)phenyl]acrylic acid Stage 3 product (1.77 g, 4 mmol) and lithium iodide (2.67 g, 20 mmol) were added to pyridine (17.7 mL) and heated at reflux for 24 h. The reaction was cooled, quenched to pH~1 with 10% $HCl_{aq}$ and extracted with DCM (2×20 mL). The combined organics were washed with 10% $HCl_{aq}$ (40 mL) then brine (40 mL), dried ($MgSO_4$) and concentrated in vacuo to afford a brown oil (1.19 g, 73%). m/z=428 [M−H]⁻.

Stage 5—Preparation of cyclopentyl (2S)-{[(3-{(1E)-3-[(1-isobutoxyethoxy)amino]-3-oxoprop-1-en-1-yl}phenyl)sulfonyl]amino}(phenyl)acetate Stage 4 product (1.19 g, 2.8 mmol), EDCI (0.64 g, 3.3 mmol) and HOBt (0.45 g, 3.3 mmol) were added to DCM (10 mL) and stirred at RT for 30 minutes. Intermediate I (2.0 mL, 14 mmol) and triethylamine (2.0 mL, 14 mmol) were added and the reaction stirred at RT for 1.5 h. The reaction was separated with water, the aqueous phase extracted with DCM (20 mL) and the combined organics concentrated in vacuo. The crude material was purified by column chromatography to afford the product as a brown oil (0.17 g, 11%). m/z=543 [M−H]⁻.

Stage 6—Preparation of cyclopentyl (2S)-[({3-[(1E)-3-(hydroxyamino)-3-oxoprop-1-en-1-yl]phenyl}sulfonyl)amino](phenyl)acetate (Example 1)

Stage 5 product (170 mg, 0.31 mmol) was dissolved in anhydrous DCM (5 mL). 4N HCl in dioxane (0.16 mL, 0.63 mmol) was added and the reaction stirred at RT for 1 h. The reaction was concentrated to dryness in vacuo to afford a brown solid. Purification by preparative HPLC afforded a yellow solid (9 mg, 5%). LCMS purity >95%, m/z=558.5 [M+H]⁺, ¹H NMR (300 MHz, $d_6$-DMSO) δ: 7.95 (1H, s), 7.89 (2H, m), 7.65 (1H, d, J=15.9 Hz), 7.52 (1H, t), 7.26 (5H, s), 6.54 (1H, d, J=15.9 Hz), 4.94 (1H, m), 1.22-1.70 (8H, m).

The following examples were prepared using the same methodology:

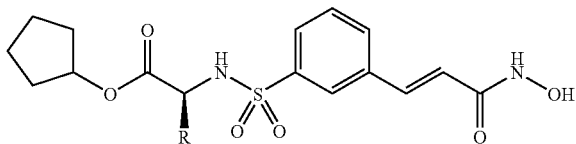

| Example | R | Chemical name | Intermediate used | Analytical data |
|---|---|---|---|---|
| 2 | cyclohexyl | Cyclopentyl (2S)-cyclohexyl[({3-[(1E)-3-(hydroxyamino)-3-oxoprop-1-en-1-yl]phenyl}sulfonyl)amino]acetate | J1 | LCMS purity 98%, m/z = 449 [M − H]⁻, ¹H NMR (300 MHz, $d_6$-DMSO) δ: 0.70-1.90 (19H, m), 3.56 (1H, m), 4.66 (1H, s), 6.55 (1H, d), 7.40-8.05 (4H, m), 8.30 (1H, d), 10.82 (1H, s). |
| 3 | isopropyl-CH2 (isobutyl) | Cyclopentyl N-({3-[(1E)-3-(hydroxyamino)-3-oxoprop-1-en-1-yl]phenyl}sulfonyl)-L-leucinate | K1 | LCMS purity >95%, m/z = 425 [M + H]⁺; ¹H NMR (300 MHz, $d_6$-DMSO) δ: 0.80 (6H, dd), 1.20-1.71 (11H, m), 3.74 (1H, m), 4.69 (1H, m), 6.56 (1H, d, J = 15.9 Hz), 7.48-7.84 (4H, m), 7.90 (1H, s), 8.39 (1H, d, J = 9 Hz), 9.13 (1H, s), 10.82 (1H, s). |
| 4 | tBuO-CH2 | Cyclopentyl O-tert-butyl-N-({3-[(1E)-3-(hydroxyamino)-3-oxoprop-1-en-1-yl]phenyl}sulfonyl)-L-serinate | O | LCMS purity >95%, m/z = 455 {M + H}⁺; ¹H NMR (300 MHz, $d_6$-DMSO) δ: 1.01 (9H, s), 1.33-1.75 (8H, m), 3.32-3.48 (2H, m), 6.56 (1H, d, J = 15.9 Hz), 7.49-7.63 (2H, m), 7.79 (2H, t), 8.36 (1H, d, J = 9.3 Hz), 9.13 (1H, s), 10.83 (1H, s). |

Example 5
Cyclopentyl (2S)-cyclohexyl({3-[(1E)-3-(hydroxyamino)-3-oxopro-1-en-1-yl]benzoyl}amino)acetate
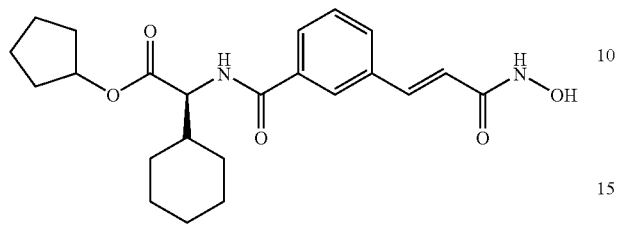
The title compound was prepared by the following methodology:
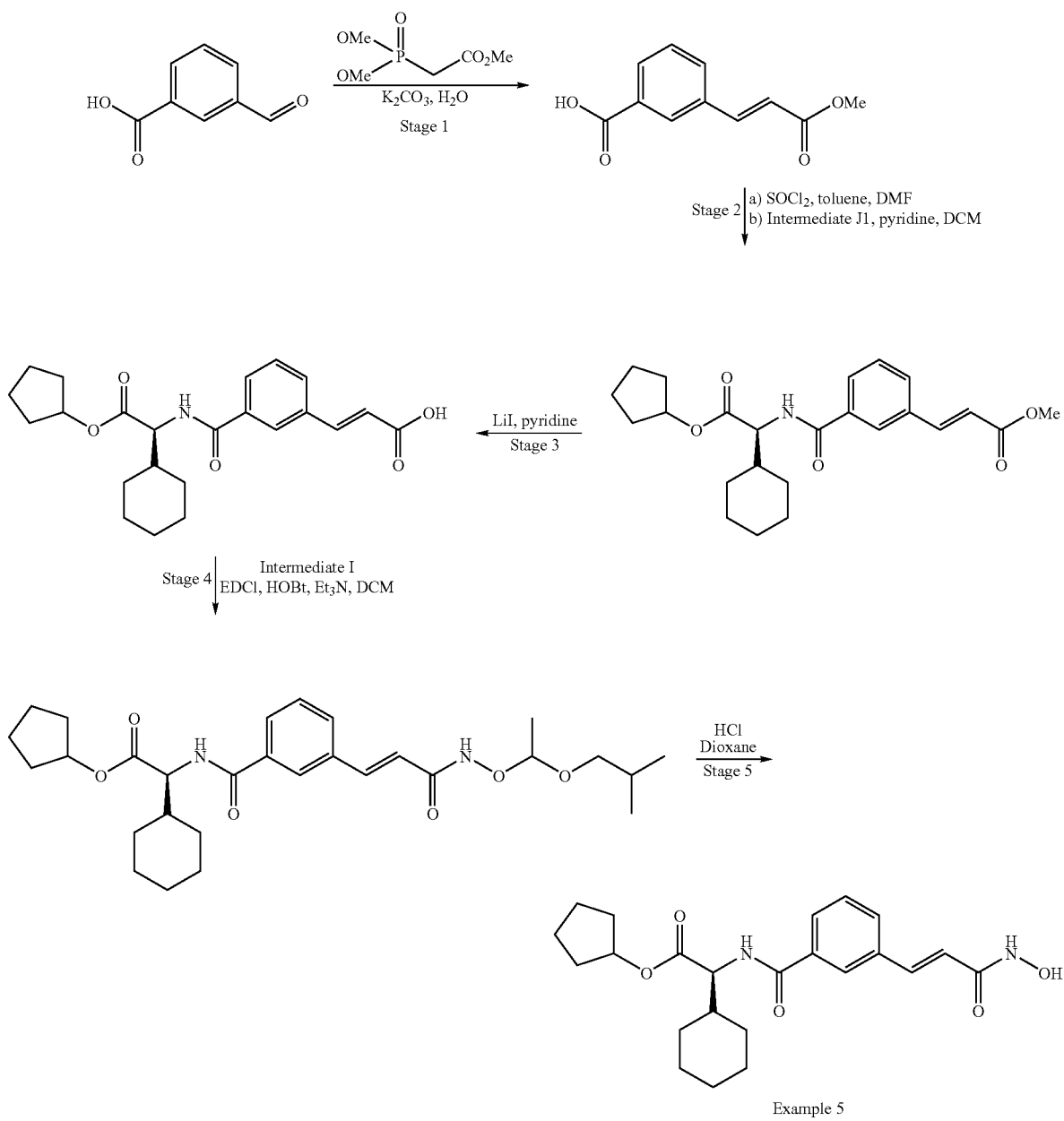

Stage 1—Preparation of 3-[(1E)-3-methoxy-3-oxo-prop-1-en-1-yl]benzoic acid

3-Carboxybenzaldehyde (25 g, 0.167 mol) and $K_2CO_3$ (69 g, 0.499 mol) were added to water (250 mL) and cooled to 0-5° C. Trimethyl phosphonoacetate (32.3 mL, 0.2 mol) was charged dropwise maintaining the reaction temperature below 15° C. The reaction was warmed and stirred at RT for 17 h. The mixture was acidified to pH~1, filtered and dried in vacuo to afford the product as an off-white solid (37.25 g, >100%—slightly wet). $^1$H NMR (300 MHz, $CD_3OD$) δ: 8.23 (1H, s), 8.06 (1H, d, J=7.8 Hz), 7.86 (1H, d, J=7.5 Hz), 7.75 (1H, d, J=15.9 Hz), 6.61 (1H, d, J=16.2 Hz), 7.54 (1H, t), 3.81 (3H, s).

Stage 2—Preparation of methyl (2E)-3-(3-{[(1S)-1-cyclohexyl-2-(cyclopentyloxy)-2-oxoethyl]carbamoyl}phenyl)acrylate Stage 1 product (5 g, 24 mmol) was added to toluene (20 mL) and DMF (6 drops) under an atmosphere of nitrogen. Thionyl chloride (5.3 mL, 72 mmol) was charged dropwise to the reaction which was then heated at reflux for 1 h. The reaction was then cooled and concentrated to dryness in vacuo, the residue was dissolved in toluene (40 mL), filtered and the filtrate concentrated to give the product as a pale yellow solid (6.1 g, >100%—some DMF). Intermediate J1 (0.5 g, 1.9 mmol) was added to pyridine (1 mL) and DCM (10 mL). The pale yellow solid (0.51 g, 2.3 mmol) was dissolved in DCM (5 mL) and charged to the reaction which was stirred for 18 h at RT. It was then concentrated to dryness in vacuo and the residue separated between EtOAc (20 mL) and 10% $HCl_{aq}$ (20 mL). The organic phase was washed with water (20 mL), sat. $NaHCO_3$ solution (20 mL) and brine (20 mL) then concentrated in vacuo to afford the product as a yellow oil (0.83 g, quant.). This was carried through to the next stage without further purification or characterization.

Stage 3—Preparation of (2E)-3-(3-{[(1S)-1-cyclohexyl-2-(cyclopentyloxy)-2-oxoethyl]carbamoyl}phenyl)acrylic acid Stage 2 product (0.83 g, 2.0 mmol) and lithium iodide (1.34 g, 10 mmol) were added to pyridine (8.3 mL) and heated at reflux for 3 days. The reaction was cooled, quenched to pH~1 with 10% $HCl_{aq}$ and extracted with DCM (2×20 mL). The combined organics were washed with 10% $HCl_{aq}$ (20 mL) then brine (20 mL), dried ($MgSO_4$) and concentrated in vacuo to afford a brown oil (0.22 g, 23% over three steps). m/z=400 $[M+H]^+$.

Stage 4—Preparation of cyclopentyl (2S)-cyclohexyl[(3-{(1E)-3-[(1-isobutoxyethoxy)amino]-3-oxoprop-1-en-1-yl}benzoyl)amino]acetate Stage 3 product (0.22 g, 0.55 mmol), EDCI (0.13 g, 0.66 mmol) and HOBt (0.09 g, 0.66 mol) were added to DCM (10 mL) and stirred at RT for 30 minutes. Intermediate I (0.23 mL, 1.65 mmol) and triethylamine (0.23 mL, 1.65 mmol) were charged and the reaction stirred at RT for 3.5 h. The reaction was separated with water, the aqueous phase extracted with DCM (20 mL) and the combined organics concentrated in vacuo. The crude material was purified by column chromatography to afford the product as a brown oil (0.14 g, 50%). m/z=537 $[M+Na]^+$.

Stage 5—Preparation of cyclopentyl (2S)-cyclohexyl({3-[(1E)-3-(hydroxyamino)-3-oxoprop-1-en-1-yl]benzyl}amino)acetate (Example 5)

Stage 4 product (140 mg, 0.27 mmol) was dissolved in anhydrous DCM (5 mL). 4N HCl in dioxane (0.16 mL, 0.54 mol) was charged and the reaction stirred at RT for 1 h. The mixture was concentrated to dryness in vacuo to afford a yellow oil. Purification by preparative HPLC afforded a pink solid (68 mg, 61%). LCMS purity 98%, m/z=415 $[M+H]^+$, $^1$H NMR (300 MHz, $d_6$-DMSO) δ: 10.82 (1H, s), 9.08 (1H, s), 8.61 (1H, d, J=7.5 Hz), 8.06 (1H, s), 7.85 (1H, d, J=8.4 Hz), 7.72 (1H, d, J=8.4 Hz), 7.54-7.49 (2H, m), 6.55 (1H, d, J=15.9 Hz), 5.11 (1H, m), 4.25 (1H, t, J=7.8 Hz), 1.92-1.47 (13H, m), 1.35-1.00 (6H, m).

The following examples were prepared using the same methodology:

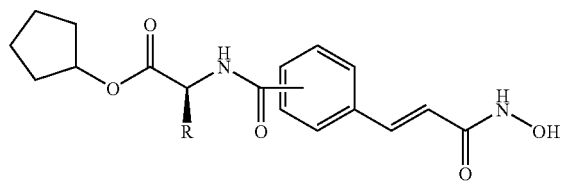

| Example | R | Chemical name | Intermediates used | Analytical data |
|---|---|---|---|---|
| 6 | phenyl | Cyclopentyl (2S)-({3-[(1E)-3-(hydroxyamino)-3-oxoprop-1-en-1-yl]benzoyl}amino)(phenyl)acetate | 3-Carboxy benzaldehyde and L1 | LCMS purity 95%, m/z = 409 $[M + H]^+$, $^1$H NMR (300 MHz, $CD_3OD$) δ: 9.04 (1H, m), 8.06 (1H, s), 7.90-7.25 (9H, m), 6.56 (1H, d, J = 15.6 Hz), 5.64 (1H, m), 5.24 (1H, m), 3.68 (1H, s), 1.97-0.82 (8H, m). |
| 7 | cyclohexyl | Cyclopentyl (2S)-cyclohexyl({4-[(1E)-3-(hydroxyamino)-3-oxoprop-1-en-1-yl]benzoyl}amino)acetate | 4-Carboxy benzaldehyde and J1 | LCMS purity 96%, m/z = 528.5 $[M + H]^+$, $^1$H NMR (300 MHz, $CD_3OD$) δ: 8.51 (1H, d), 7.87 (2H, d), 7.67 (2H, d), 6.58 (1H, d), 5.23 (1H, m), 4.42 (1H, t), 1.55-2.03 (13H, m), 1.08-1.42 (6H, m). |

-continued

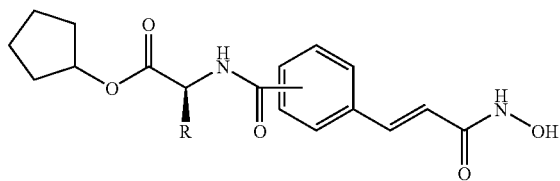

| Example | R | Chemical name | Intermediates used | Analytical data |
|---|---|---|---|---|
| 8 | isopropyl | Cyclopentyl N-{4-[(1E)-3-(hydroxyamino)-3-oxoprop-1-en-1-yl]benzoyl}-L-leucinate | 4-Carboxy benzaldehyde and K1 | LCMS purity 98%, m/z = 389 [M + H]$^+$, $^1$H NMR (300 MHz, d$_6$-DMSO) δ: 0.90 (6H, dd), 1.45-1.90 (11H, m), 4.40 (1H, m), 5.09 (1H, m), 6.55 (1H, d, J = 15.9 Hz), 7.50 (1H, d, J = 16.2 Hz), 7.67 (2H, d, J = 8.1 Hz), 7.89 (2H, d, J = 8.1 Hz), 8.71 (1H, d, J = 7.5 Hz), 10.82 (1H, s). |

Example 9

Cyclopentyl (2S)-cyclohexyl[(3-{4-[(1E)-3-(hydroxyamino)-3-oxoprop-1-en-1-yl]phenoxy}propyl)amino]acetate

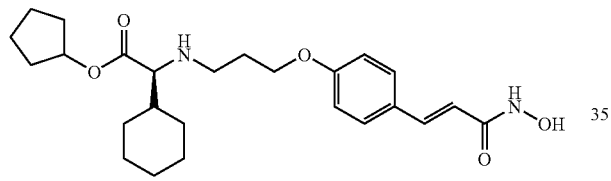

The title compound was prepared by the following methodology:

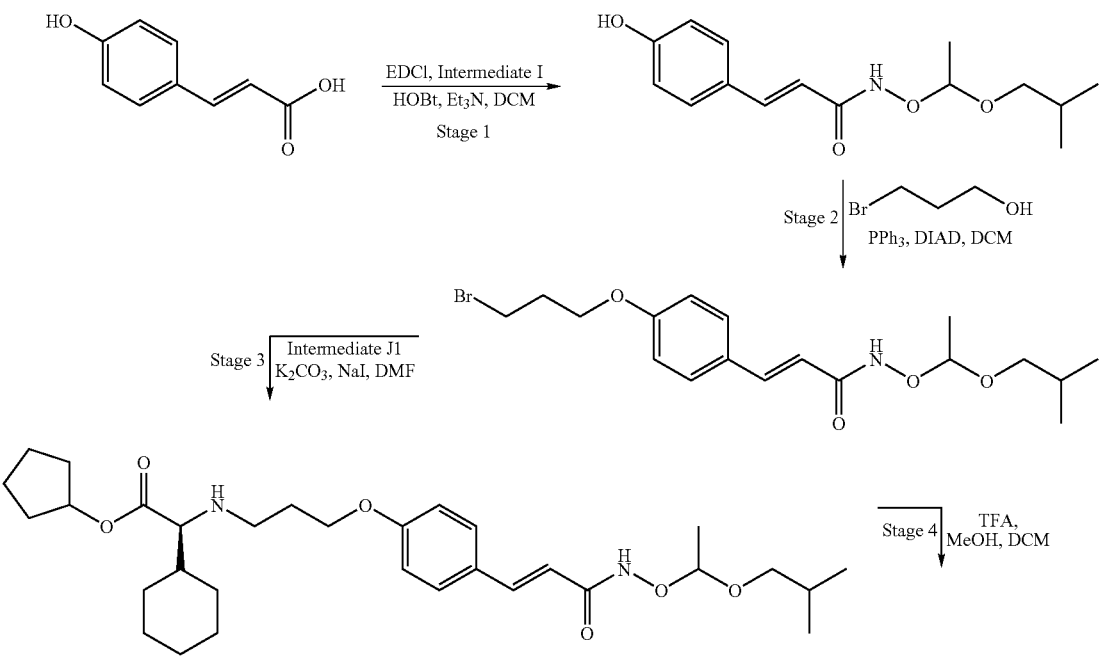

-continued

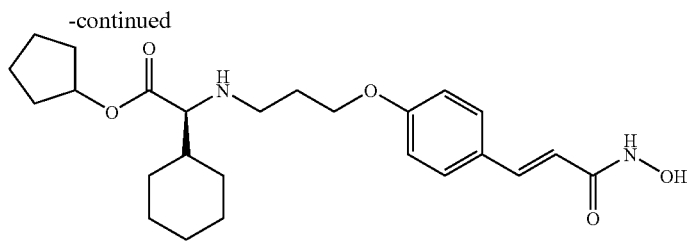

Example 9

Stage 1—Preparation of (2E)-3-(4-hydroxyphenyl)-N-(1-isobutoxyethoxy)acrylamide 4-Hydroxycinnamic acid (1 g, 6.1 mmol), EDCI (1.76 g, 9.1 mmol) and HOBt (1.24 g, 9.1 mmol) were added to DCM (20 mL) and stirred at RT for 45 minutes. Intermediate I (4.2 mL, 30.5 mmol) and triethylamine (4.1 mL, 30.5 mmol) were added and the reaction stirred at RT for 1.5 h. The reaction was separated with water, the aqueous phase extracted with DCM (20 mL) and the combined organics dried (MgSO$_4$) and concentrated in vacuo. The crude material was purified by column chromatography to afford the product as a clear oil (1.39 g, 82%). m/z=278 [M−H]$^-$.

Stage 2—Preparation of (2E)-3-[4-(3-bromopropoxy)phenyl]-N-(1-isobutoxyethoxy)acrylamide Stage 1 product (0.66 g, 2.4 mmol), 3-bromopropan-1-ol (0.24 mL, 2.6 mmol) and triphenylphosphine (0.96 g, 4.8 mmol) were added to DCM (20 mL) and stirred under nitrogen for 10 minutes. DIAD (0.56 mL, 2.9 mmol) was charged dropwise and the reaction stirred at RT for 1 h. The reaction was concentrated to dryness in vacuo to afford a pale yellow oil. Purification by column chromatography gave the product as a white solid (0.68 g, 72%). m/z=398/400 [M−H]$^-$.

Stage 3—Preparation of cyclopentyl (2S)-cyclohexyl{[3-(4-{(1E)-3-[(1-isobutoxyethoxy)amino]-3-oxoprop-1-en-1-yl}phenoxy)propyl]amino}acetate Intermediate J1 (0.14 g, 0.54 mmol), K$_2$CO$_3$ (0.3 g, 2.2 mmol) and sodium iodide (0.16 g, 1.07 mmol) were added to DMF (5 mL) and heated to 70° C. Stage 2 product (0.22 g, 0.55 mmol) was dissolved in DMF (2 mL) and charged to the reaction which was stirred at 70-80° C. under nitrogen for 24 h. Further stage 2 product (0.1 g, 0.25 mmol) was charged and the reaction stirred at 80° C. for 4.5 h. The reaction was then concentrated to dryness in vacuo, the residue was separated with water (10 mL) and EtOAc (10 mL) and the aqueous phase extracted with EtOAc (10 mL). The combined organics were washed with brine (10 mL), dried (MgSO$_4$) and concentrated in vacuo to give the crude product as a yellow oil. Purification by column chromatography afforded the product as a clear oil (0.1 g, 34%). m/z=546 [M+H]$^+$.

Stage 4—Preparation of cyclopentyl (2S)-cyclohexyl [(3-{4-[(1E)-3-(hydroxyamino)-3-oxoprop-1-en-1-yl]phenoxy}propyl)amino]acetate Stage 3 product (100 mg, 0.31 mmol) was dissolved in anhydrous DCM (0.4 mL) and MeOH (0.5 mL). TFA (0.1 mL) was charged and the reaction stirred at RT for 1 h. It was then concentrated to dryness in vacuo to afford a yellow oil. Purification by preparative HPLC afforded the product as a white solid (10 mg, 12%). LCMS purity 100%, m/z=445 [M+H]$^+$, $^1$H NMR (300 MHz, CD$_3$OD) δ: 7.53 (3H, m), 6.97 (2H, d, J=8.4 Hz), 6.35 (1H, d, J=15.9 Hz), 5.33 (2H, m), 4.16 (2H, m), 3.90 (1H, m), 3.83 (1H, d, J=4.5 Hz), 2.23 (2H, m), 2.09-1.57 (12H, m), 1.45-0.98 (6H, m), 0.92 (2H, m).

The following examples were prepared using the same methodology:

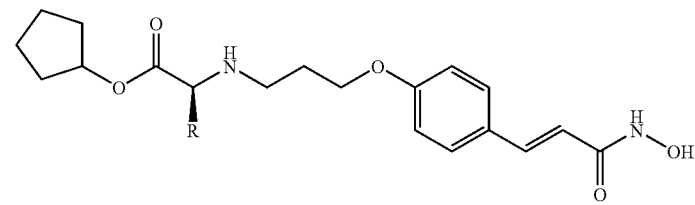

| Example | R | Chemical name | Intermediate used | Analytical data |
|---|---|---|---|---|
| 10 | ![tert-butoxy] | Cyclopentyl O-tert-butyl-N-(3-{4-[(1E)-3-(hydroxyamino)-3-oxoprop-1-en-1-yl]phenoxy}propyl)-L-serinate | O | LCMS purity 95%, m/z = 449 [M + H]$^+$, $^1$H NMR (300 MHz, CD$_3$OD) δ: 7.53 (3H, m), 6.99 (2H, m), 6.36 (1H, m), 5.34 (1H, m), 4.29 (1H, m), 4.19 (2H, m), 3.92 (2H, m), 2.26 (2H, m), 2.03-1.59 (8H, m), 1.31 (1H, m), 1.23 (9H, s), 0.90 (1H, m). |

-continued

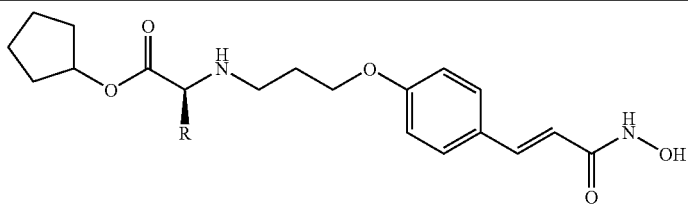

| Example | R | Chemical name | Intermediate used | Analytical data |
|---|---|---|---|---|
| 11 | ⅄ (isopropyl) | Cyclopentyl N-(3-{4-[(1E)-3-(hydroxyamino)-3-oxoprop-1-en-1-yl]phenoxy}propyl)-L-leucinate | K1 | LCMS purity 100%, m/z = 419 [M + H]$^+$, $^1$H NMR (300 MHz, CD$_3$OD) δ: 7.53 (3H, m), 6.98 (2H, d, J = 8.4 Hz), 6.35 (1H, d, J = 15.6 Hz), 5.36 (1H, m), 4.18 (2H, m), 4.05 (1H, m), 2.23 (2H, m), 2.07-1.58 (10H, m), 1.31 (1H, m), 1.11-0.78 (8H, m). |

Example 12

Cyclopentyl (2S)-cyclohexyl({3-[(1E)-3-(hydroxyamino)-3-oxoprop-1-en-1-yl]benzyl}amino)acetate

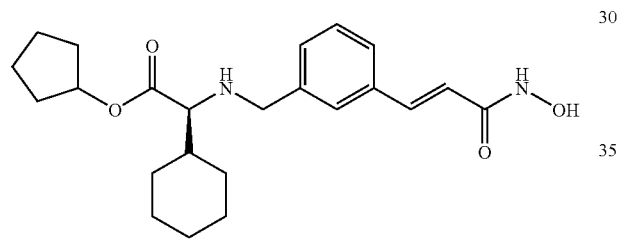

The title compound was prepared by the following methodology:

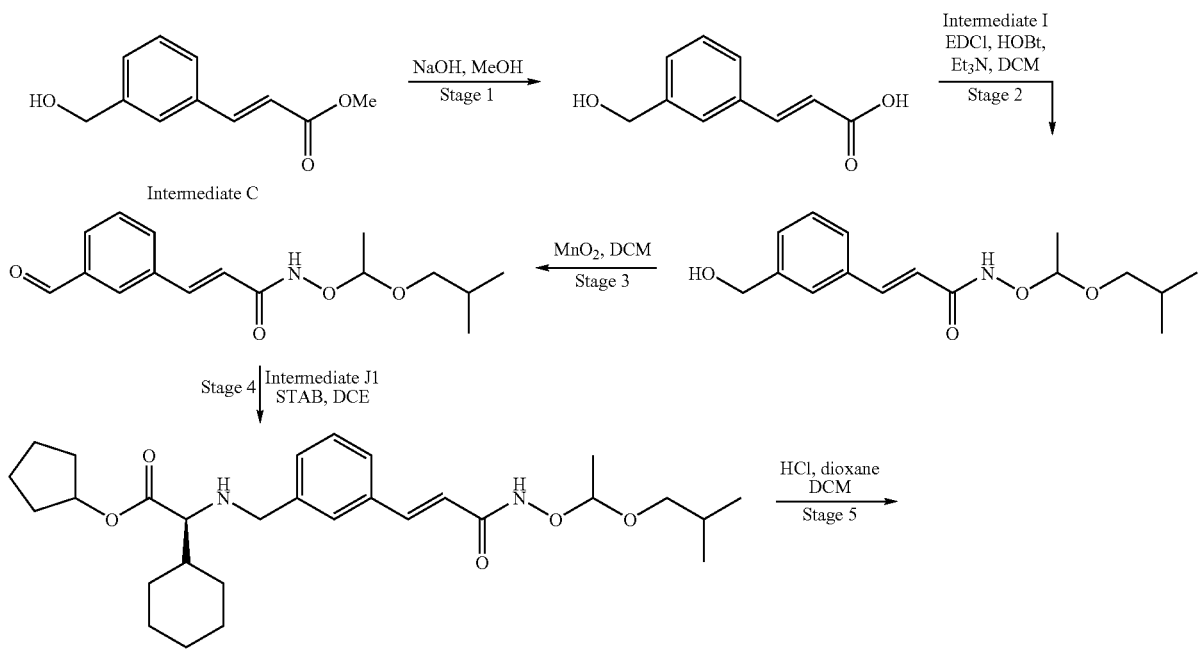

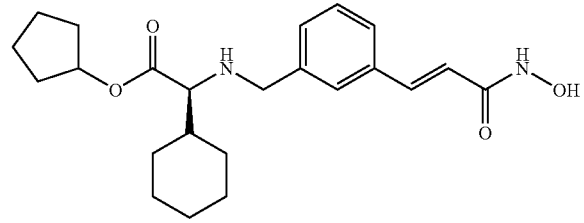 [SMILES: O=C(/C=C/c1cccc(CN[C@H](C(=O)OC2CCCC2)C2CCCCC2)c1)NO]

Example 12

Stage 1—Preparation of (2E)-3-[3-(hydroxymethyl)phenyl]acrylic acid

Intermediate C (16.04 g, 83.5 mmol) was added to 1M NaOH$_{aq}$ (28 mL) and MeOH (41 mL) and stirred at RT for 15.5 h. The MeOH was removed in vacuo and the residue washed with EtOAc. The aqueous phase was acidified to pH~1 and the resulting precipitate was filtered and dried in vacuo to afford the title product as a white solid (7.29 g, 49%). m/z=179 [M+H]$^+$.

Stage 2—Preparation of (2E)-3-[3-(1-hydroxyethyl)phenyl]-N-(1-isobutoxyethoxy)acrylamide Stage 1 product (7.29 g, 41 mmol), EDCI (9.4 g, 49 mmol) and HOBt (6.6 g, 49 mmol) were added to DCM (100 mL) and stirred at RT for 30 minutes. Intermediate I (17.3 mL, 123 mmol) and triethylamine (28.5 mL, 205 mmol) were charged and the reaction stirred at RT for 2.5 h. The reaction was separated with water, the aqueous phase extracted with DCM (50 mL) and the combined organics dried (MgSO$_4$) and concentrated in vacuo. The crude material was purified by column chromatography to afford the product as a pale yellow oil (6.54 g, 54%). $^1$H NMR (300 MHz, CD$_3$OD) δ: 7.71-7.33 (5H, m), 6.57 (2H, d, J=15.6 Hz), 5.01 (1H, m), 4.65 (2H, s), 3.32 (2H, m), 1.40 (3H, d, J=5.4 Hz), 0.93 (6H, m).

Stage 3—Preparation of (2E)-3-(3-formylphenyl)-N-(1-isobutoxyethoxy)acrylamide Stage 2 product (6.5 g, 22 mmol) and manganese dioxide (9.6 g, 110 mmol) were stirred in DCM (100 mL) at RT for 16 h. The reaction was filtered through celite and the filtrate concentrated to dryness to afford the product as a grey solid (4.8 g, 75%). $^1$H NMR (300 MHz, CDCl$_3$) δ: 10.05 (1H, s), 8.06 (1H, s), 7.97-7.52 (4H, m), 6.55 (1H, d), 5.05 (1H, m), 3.35 (2H, m), 1.47-1.44 (3H, m) 0.94 (6H, m).

Stage 4—Preparation of cyclopentyl (2S)-cyclohexyl [(3-{(1E)-3-[(1-isobutoxyethoxy)amino]-3-oxoprop-1-en-1-yl}benzyl)amino]acetate Stage 3 product (0.3 g, 1.03 mmol) and Intermediate J1 (0.32 g, 1.22 mmol) were dissolved in 1,2-dichloroethane (10 mL). STAB (0.33 g, 1.56 mmol) was charged and the reaction stirred under nitrogen for 1 h. It was then quenched with sat. NaHCO$_3$ solution (10 mL). The aqueous phase was extracted with DCM (2×10 mL) and the combined organics dried (MgSO$_4$) and concentrated to dryness in vacuo to afford the product as a brown oil (0.59 g, >100%). m/z=501 [M+H]$^+$.

Stage 5—Preparation of cyclopentyl (2S)-cyclohexyl ({3-[(1E)-3-(hydroxyamino)-3-oxoprop-1-en-1-yl]benzyl}amino)acetate (Example 12)

4N HCl in dioxane (0.59 mL, 2.4 mmol) was added to a solution of stage 4 product (0.59 g, 1.2 mmol) in DCM and the reaction stirred for 3 h. The reaction was concentrated to dryness in vacuo to afford a yellow oil. Purification by preparative HPLC afforded the desired product as a white solid (11.5 mg, 2.4%). LCMS purity >95%, m/z=400.5 [M+H]$^+$, $^1$H NMR (300 MHz, d$_6$-DMSO) δ: 10.75 (1H, s), 9.03 (1H, s), 7.25-7.51 (5H, m), 6.45 (1H, d, J=15.6 Hz), 5.09 (1H, m), 3.64 (2H, dd), 2.83 (1H, m), 1.42-1.93 (13H, m), 0.92-1.25 (6H, m).

The following examples were prepared using the same methodology:

| Example | Chemical name | Intermediates used | Analytical data |
|---|---|---|---|
| 13 | Cyclopentyl (2S)-({3-[(1E)-3-(hydroxyamino)-3-oxoprop-1-en-1-yl]benzyl}amino)(phenyl)acetate | C, L1 | LCMS purity >95%, $^1$H NMR (300 MHz, d$_6$-DMSO) δ: 1.30-1.85 (8H, m), 3.10 (1H, m), 3.66 (2H, d, J = 5.1 Hz), 4.28 (1H, d, J = 8.7 Hz), 5.05 (1H, m), 6.45 (1H, d, J = 15.9 Hz, 7.22-7.57 (10H, m), 9.03 (1H, s), 10.74 (1H, s). |
| 14 | Cyclopentyl (2S)-cyclohexyl({4-[(1E)-3-(hydroxyamino)-3-oxoprop-1-en-1-yl]benzyl}amino)acetate | A, J1 | LCMS purity 98%, m/z = 401 [M + H]$^+$, $^1$H NMR (300 MHz, d$_6$-DMSO) δ: 9.41 (1H, s), 8.99 (1H, s), 8.31 (1H, s), 7.32-7.75 (5H, m), 6.53 (1H, d), 5.23 (1H, m), 5.11 (1H, s), 4.16 (2H, m), 3.60-3.95 (2H, m), 2.97 (1H, m), 1.40-2.05 (12H, m), 0.70-1.32 (6H, m). |
| 15 | Cyclopentyl N-{4-[(1E)-3-(hydroxyamino)-3-oxoprop-1-en-1-yl]benzyl}-L-leucinate | A, K1 | LCMS purity 99%, m/z = 375 [M + H]$^+$, $^1$H NMR (300 MHz, d$_6$-DMSO) δ: 0.91 (6H, d), 1.20 (1H, t), 1.55-1.76 (10H, m), 1.78-1.95 (2H, m), 3.85-4.30 (2H, m), 5.19 (1H, m), 6.50 (1H, d), |

| Example | Chemical name | Intermediates used | Analytical data |
|---|---|---|---|
| | | | 7.35-7.70 (5H, m), 9.08 (1H, s), 9.45 (1H, s). |
| 16 | Cyclopentyl O-tert-butyl-N-{4-[(1E)-3-(hydroxyamino)-3-oxoprop-1-en-1-yl]benzyl}-L-serinate | A, O | LCMS purity 100%, m/z = 405 [M + H]⁺, ¹H NMR (300 MHz, CD₃OD) δ: 7.72-7.50 (5H, m), 6.58 (1H, m), 5.33 (1H, m), 4.32 (2H, m), 4.22 (1H, m), 3.99-3.80 (3H, m), 3.14 (1H, m), 2.03-1.60 (8H, m), 1.24 (9H, s), 0.92 (1H, m). |
| 17 | Cyclopentyl (2S)-({4-[(1E)-3-(hydroxyamino)-3-oxoprop-1-en-1-yl]benzyl}amino)(phenyl)acetate | A, L1 | LCMS purity 100%, m/z = 395 [M + H]⁺, ¹H NMR (300 MHz, d₆-DMSO) δ: 7.69-7.46 (10H, m), 6.49 (1H, d, J = 15.6 Hz), 5.15 (1H, m), 4.07 (2H, m), 1.88-1.13 (8H, m). |
| 18 | Cyclopentyl N-{4-[(1E)-3-(hydroxyamino)-3-oxoprop-1-en-1-yl]benzyl}-D-leucinate | A, R | LCMS purity 100%, m/z = 375 [M + H]⁺, ¹H NMR (300 MHz, CD₃OD) δ: 7.67-7.45 (3H, m), 7.37 (2H, d, J = 7.8 Hz), 6.47 (1H, d, J = 15.6 Hz), 5.19 (1H, m), 3.71 (2H, q), 3.23 (1H, t), 2.02-1.18 (11H, m), 1.01-0.75 (6H, m). |
| 19 | Cyclopentyl (2R)-cyclohexyl({4-[(1E)-3-(hydroxyamino)-3-oxoprop-1-en-1-yl]benzyl}amino)acetate | A, Q | LCMS purity 100%, m/z = 401 [M + H]⁺, ¹H NMR (300 MHz, CD₃OD) δ: 7.70-7.43 (3H, m), 7.36 (2H, d, J = 8.1 Hz), 6.47 (1H, d, J = 15.6 Hz), 5.18 (1H, m), 3.72 (2H, q), 2.96 (1H, d, J = 6 Hz), 2.00-1.45 (13H, m), 1.39-0.82 (6H, m). |
| 20 | Cyclopentyl O-tert-butyl-N-{4-[(1E)-3-(hydroxyamino)-3-oxoprop-1-en-1-yl]benzyl}-D-serinate | A, S | LCMS purity 100%, m/z = 405 [M + H]⁺, ¹H NMR (300 MHz, CD₃OD) δ: 7.63-7.48 (3H, m), 7.39 (2H, d, J = 7.8 Hz), 6.48 (1H, d, J = 15.6 Hz), 5.20 (1H, m), 3.80 (2H, q), 3.61 (2H, m), 3.38 (1H, t), 1.95-1.57 (8H, m), 1.31 (1H, m), 1.17 (9H, s). |
| 21 | Ethyl (2S)-cyclohexyl({4-[(1E)-3-(hydroxyamino)-3-oxoprop-1-en-1-yl]benzyl}amino)acetate | A, J3 | LCMS purity >98%, m/z = 361 [M + H]⁺, ¹H NMR (300 MHz, d₆-DMSO) δ: 7.49 (2H, d, J = 7.9 Hz), 7.44 (1H, d, J = 15.8 Hz), 7.33 (2H, d, J = 8.0 Hz), 6.42 (1H, d, J = 15.8 Hz), 4.10 (2H, q, J = 7.0 Hz), 3.77 (1H, d, J = 15.8 Hz), 3.50 (1H, d, J = 9.3 Hz), 2.87 (1H, m), 1.82 (1H, d J = 11.4 Hz), 1.35-1.65 (5H, m), 1.19 (3H, t, J = 7.1 Hz), 0.9-1.25 (5H, m). |
| 22 | Cyclopentyl (2R)-({4-[(1E)-3-(hydroxyamino)-3-oxoprop-1-en-1-yl]benzyl}amino)(phenyl)acetate | A, L1 | LCMS purity 100%, m/z = 395 [M + H]⁺, ¹H NMR (300 MHz, d₆-DMSO) δ: 7.69-7.46 (10H, m), 6.49 (1H, d, J = 15.6 Hz), 5.15 (1H, m), 4.07 (2H, m), 1.88-1.13 (8H, m). |
| 23 | 2,3-Dihydro-1H-inden-2-yl (2S)-cyclohexyl({4-[(1E)-3-(hydroxyamino)-3-oxoprop-1-en-1-yl]benzyl}amino)acetate | A, J6 | LCMS purity >98%, m/z = 449 [M + H]⁺, ¹H NMR (300 MHz, d₆-DMSO) δ: 10.72 (1H, br s), 9.00 (1H, br s), 7.38-7.46 (3H, m), 7.22-7.27 (4H, m), 7.15-7.19 (2H, m), 6.41 (1H, d, J = 15.8 Hz), 5.44-5.50 (1H, m), 3.74 (1H, d, J = 14 Hz), 3.50 (1H, d, J = 14 Hz), 2.75-2.95 (3H, m), 1.77 (1H, d, J = 12.2 Hz), 0.86-1.65 (11H, m). |
| 24 | Benzyl (2S)-cyclohexyl({4-[(1E)-3-(hydroxyamino)-3-oxoprop-1-en-1-yl]benzyl}amino)acetate | A, J9 | LCMS purity >98%, m/z = 423 [M + H]⁺, ¹H NMR (300 MHz, d₆-DMSO) δ: 10.72 (1H, br s), 9.00 (1H, br s), 7.15-7.55 (10H, m), 6.42 (1H, d, J = 15.6 Hz), 5.13 (2H, s), 3.76 (1H, d, J = 14.6 Hz), 3.50 (1H, d, J = 14.0 Hz), 2.90-3.0 (1H, m), 1.40-1.82 (7H, m), 0.85-1.25 (7H, m). |
| 25 | Allyl (2S)-cyclohexyl({4-[(1E)-3-(hydroxyamino)-3-oxoprop-1-en-1-yl]benzyl}amino)acetate | A, J4 | LCMS purity >98%, m/z = 373 [M + H]⁺, ¹H NMR (300 MHz, d₆-DMSO) δ: 10.72 (1H, br s), 9.00 (1H, br s), 7.49 (2H, J = 8.1 Hz), 7.43 (1H, d, J = 15.9 Hz), 7.33 (2H, d, J = 8.1 Hz), 6.43 (1H, d, J = 15.8 Hz), 5.85-6.0 (1H, m), 5.32 (1H, dd, J = 1.7, 17.2 Hz), 5.22 (1H, dd, J = 1.7, 10.4 Hz), 4.54-4.62 (2H, m), 3.79 (1H, d, J = 14 Hz), 3.52 (1H, d, J = 14 Hz), 2.94 (1H, br s), 0.9-1.9 (10H, m). |
| 26 | Bicyclo[2.2.1]hept-2-yl (2S)-cyclohexyl({4-[(1E)-3-(hydroxyamino)-3-oxoprop-1-en-1-yl]benzyl}amino)acetate | A, J7 | LCMS purity >95%, m/z = 427 [M + H]⁺, ¹H NMR (300 MHz, d₆-DMSO) δ: 7.49 (2H, J = 8.1 Hz), 7.43 (1H, d, J = 15.9 Hz), |

-continued

| Example | Chemical name | Intermediates used | Analytical data |
|---|---|---|---|
| | | | 7.33 (2H, d, J = 8.1 Hz), 6.43 (1H, d, J = 15.8 Hz), 4.50-4.11 (1H, m), 3.79 (1H, d, J = 14 Hz), 3.52 (1H, d, J = 14 Hz), 2.66 (1H, m), 0.65-2.40 (22H, m). |
| 27 | 2-Methylcyclopentyl (2S)-cyclohexyl({4-[(1E)-3-(hydroxyamino)-3-oxoprop-1-en-1-yl]benzyl}amino)acetate | A, J5 | LCMS purity >95%, m/z = 415 [M + H]$^+$, $^1$H NMR (300 MHz, d$_6$-DMSO) δ: 10.72 (1H, br s), 9.00 (1H, br s), 7.49 (2H, d, J = 8 Hz), 7.43 (1H, d, J = 15.8 Hz), 7.32 (2H, d, J = 8 Hz), 6.43 (1H, d, J = 15.8 Hz), 4.63 (1H, m), 3.76 (1H, d, J = 14 Hz), 3.50 (1H, d, J = 14 Hz), 2.85 (1H, m), 0.95-2.04 (18H, m), 0.94 (3H, d, J = 6.2 Hz). |
| 28 | 3-Methylcyclopentyl (2S)-cyclohexyl({4-[(1E)-3-(hydroxyamino)-3-oxoprop-1-en-1-yl]benzyl}amino)acetate | A, J8 | LCMS purity >95%, m/z = 415 [M + H]$^+$, $^1$H NMR (300 MHz, d$_6$-DMSO) δ: 10.71 (1H, br s), 9.00 (1H, br s), 7.48 (2H, d, J = 8 Hz), 7.38 (1H, d, J = 14 Hz), 7.32 (1H, d, J = 7.9 Hz), 6.42 (1H, d, J = 15.7 Hz), 5.05 (1H, m), 3.75 (1H, d, J = 14 Hz), 3.52 (1H, d, J = 16.2 Hz), 2.84 (1H, m), 1.00-2.80 (18H, m), 1.00 (3H, d, J = 6.7 Hz). |
| 29 | Methyl N-{4-[(1E)-3-(hydroxyamino)-3-oxoprop-1-en-1-yl]benzyl}-L-tryptophanate | A, P | LCMS purity 98%, m/z = 393.4 [M + H]$^+$, $^1$H NMR (300 MHz, d$_6$-DMSO) δ: 10.81 (1H, br s), 7.45 (2H, d, J = 8.1 Hz), 7.39 (2H, d, J = 8.9 Hz), 7.30 (3H, m), 7.00-7.14 (2H, m), 6.95-6.98 (1H, m), 6.42 (1H, d, J = 15.8 Hz), 4.32 (1H, m), 3.77 (1H, d, J = 13.6 Hz), 3.62 (1H, d, J = 17.3 Hz), 3.51 (3H, s), 3.04 (2H, d, J = 6.6 Hz). |
| 30 | 2-Morpholin-4-ylethyl (2S)-cyclohexyl({4-[(1E)-3-(hydroxyamino)-3-oxoprop-1-en-1-yl]benzyl}amino)acetate | A, J10 | LCMS purity >98%, m/z = 446.2 [M + H]$^+$, $^1$H NMR (300 MHz, d$_6$-DMSO) δ: 7.48 (2H, d, J = 7.2 Hz), 7.38 (1H, d, J = 14.7 Hz), 7.32 (2H, d, J = 7.5 Hz), 6.43 (1H, d, J = 13.4 Hz), 4.10-4.28 (2H, m), 3.78 (1H, d, J = 13.9 Hz), 3.45-3.62 (5H, m), 3.16 (1H, s), 2.87 (1H, brs), 2.38 (4H, m), 1.83 (1H, d, J = 11.3 Hz), 0.80-1.75 (10H, m). |
| 31 | 2-(Dimethylamino)ethyl (2S)-cyclohexyl({4-[(1E)-3-(hydroxyamino)-3-oxoprop-1-en-1-yl]benzyl}amino)acetate | A, J11 | LCMS purity >98%, m/z = 404.2 [M + H]$^+$, $^1$H NMR (300 MHz, d$_6$-DMSO) δ: 10.75 (1H, br s), 9.06 (1H, br s), 7.49 (2H, d, J = 8.0 Hz), 7.42 (1H, d, J = 15.6 Hz), 7.32 (2H, d, J = 8.0 Hz), 6.42 (1H, d, J = 15.8 Hz), 4.09-4.16 (3H, m), 3.77 (1H, d, J = 13.8 Hz), 3.49 (1H, d, J = 13.7 Hz), 2.86 (1H, m), 2.45 (2H, t, J = 5.5 Hz), 2.15 (6H, s), 0.94-1.88 (11H, m). |
| 32 | tert-Butyl (2S)-cyclohexyl({4-[(1E)-3-(hydroxyamino)-3-oxoprop-1-en-1-yl]benzyl}amino)acetate | A, J2 | LCMS purity 98%, m/z = 389 [M + H]$^+$, $^1$H NMR (300 MHz, d$_6$-DMSO) δ: 0.88 (1H, m), 1.18 (4H, m), 1.42 (9H, s), 1.67 (5H, m), 1.73 (1H, m), 3.75 (1H, m), 4.13 (2H, m), 6.50 (1H, d, J = 15.9 Hz), 7.49 (3H, m), 7.63 (2H, d, J = 7.8 Hz), 9.08 (1H, m), 9.28 (1H, m), 10.81 (1H, m). |
| 33 | Cyclopentyl (2S)-cyclohexyl({4-[3-(hydroxyamino)-3-oxopropyl]benzyl}amino)acetate | B, J1 | LCMS purity 100%, m/z = 403 [M + H]$^+$, $^1$H NMR (300 MHz, d$_6$-DMSO) δ: 10.35 (1H, s), 8.68 (1H, s), 7.15 (4H, q), 5.11 (1H, m), 3.70 (1H, d), 3.44 (1H, d), 2.78 (2H, m), 2.39 (2H, m), 1.90-0.91 (19H, m). |
| 34 | Cyclopentyl N-{4-[3-(hydroxyamino)-3-oxopropyl]benzyl}-L-leucinate | B, K1 | LCMS purity 100%, m/z = 377 [M + H]$^+$, $^1$H NMR (300 MHz, d$_6$-DMSO) δ: 10.34 (1H, s), 8.68 (1H, s), 7.15 (4H, q), 5.10 (1H, m), 3.68 (1H, d), 3.49 (1H, d), 3.06 (1H, m), 2.78 (2H, t), 2.24 (2H, t), 1.91-1.28 (11H, m), 0.83 (6H, dd). |
| 35 | 2-Morpholin-4-ylethyl N-{4-[3-(hydroxyamino)-3-oxopropyl]benzyl}-L-leucinate | B, K3 | LCMS purity 90%, m/z = 422 [M + H]$^+$, $^1$H NMR (300 MHz, CD$_3$OD) δ: 7.46 (2H, d, J = 8.1 Hz), 7.32 (2H, d, J = 7.9 Hz), 4.57 (2H, d), 4.27 (2H, dd, J = 12.9, 22.8 Hz), 4.14 (1H, m), 3.97 (4H, br s), 3.59 (2H, t, J = 5.1 Hz), 3.42 (3H, br s), 2.97 (2H, t, J = 7.4 Hz), |

-continued

| Example | Chemical name | Intermediates used | Analytical data |
|---|---|---|---|
| | | | 2.45 (2H, t, J = 7.4 Hz), 1.96-1.68 (4H, m), 0.99 (6H, t, J = 6.8 Hz). |
| 36 | Bicyclo[2.2.1]hept-2-yl N-{4-[3-(hydroxyamino)-3-oxopropyl]benzyl}-L-leucinate | B, K4 | LCMS purity 98%, m/z = 403 [M + H]+, 1H NMR (300 MHz, CD3OD) δ: 7.43 (2H, d, J = 7.9 Hz), 7.33 (2H, d, J = 7.9 Hz), 4.76 (1H, t, J = 7.4 Hz), 4.21 (2H, qd, J = 3.0, 12.9 Hz), 3.98 (1H, m), 2.96 (2H, t, J = 7.5 Hz), 2.41 (2H, t, J = 7.6 Hz), 2.35 (2H, m), 1.77 (4H, m), 1.52 (3H, m), 1.22 (3H, m), 0.99 (7H, m). |
| 37 | 2,3-Dihydro-1H-inden-2-yl N-{4-[3-(hydroxyamino)-3-oxopropyl]benzyl}-L-leucinate | B, K5 | LCMS purity 87%, m/z = 425 [M + H]+, 1H NMR (300 MHz, CD3OD) δ: 7.35-7.16 (8H, m), 5.65 (1H, m), 5.48 (1H, s), 4.17 (1H, q, J = 12.8 Hz), 3.94 (1H, m), 3.39 (1H, d, J = 5.7 Hz), 3.39 (1H, t, J = 5.7 Hz), 3.07 (2H, m), 2.94 (1H, t, J = 7.6 Hz), 2.39 (1H, t, J = 8.6 Hz), 1.86-1.58 (4H, m), 0.88 (7H, m). |
| 38 | 2-(Dimethylamino)ethyl N-{4-[3-(hydroxyamino)-3-oxopropyl]benzyl}-L-leucinate | B, K6 | LCMS purity 90%, m/z = 380 [M + H]+, 1H NMR (300 MHz, CD3OD) δ: 7.46 (2H, d, J = 8.1 Hz), 7.34 (2H, d, J = 8.1 Hz), 4.70-4.44 (2H, m), 4.29 (2H, m), 4.15 (1H, m), 3.56 (2H, t, J = 4.99 Hz), 2.96 (6H, s), 2.93 (1H, m), 2.43 (2H, t, J = 7.44 Hz), 1.85 (4H, m), 0.99 (6H, t, J = 6.78 Hz). |
| 39 | Cyclopentyl (2S)-({4-[3-(hydroxyamino)-3-oxopropyl]benzyl}amino)(phenyl)acetate | B, L1 | LCMS purity 95%, m/z = 397 [M + H]+, 1H NMR (300 MHz, d6-DMSO) δ: 1.36-1.90 (8H, m), 2.27 (2H, t, J = 7.6 Hz), 2.83 (2H, t, J = 7.6 Hz), 3.91 (1H, m), 4.08 (1H, m), 5.16 (2H, m), 7.24 (2H, d, J = 7.9 Hz), 7.37 (2H, d, J = 7.9 Hz), 7.50 (5H, m), 8.71 (1H, br s), 10.01 (1H, m), 10.42 (1H, s). |
| 40 | tert-Butyl (2S)-cyclohexyl({4-[3-(hydroxyamino)-3-oxopropyl]benzyl}amino)acetate | B, J2 | LCMS purity 99%, m/z = 391 [M + H]+, 1H NMR (300 MHz, d6-DMSO) δ: 0.87 (1H, m), 1.15 (4H, m), 1.43 (9H, s), 1.71 (4H, m), 1.91 (1H, m), 2.26 (2H, t, J = 8.1 Hz), 2.82 (2H, t, J = 8.1 Hz), 3.73 (1H, m), 4.07 (2H, m), 7.26 (2H, d, J = 7.8 Hz), 7.36 (2H, d, J = 7.8 Hz), 8.74 (1H, m), 9.18 (1H, m), 10.40 (1H, m). |
| 41 | tert-Butyl N-{4-[3-(hydroxyamino)-3-oxopropyl]benzyl}-L-leucinate | B, K2 | LCMS purity 95%, m/z = 365 [M + H]+, 1H NMR (300 MHz, CD3OD) δ: 7.45-7.40 (2H, m), 7.37-7.33 (2H, m), 4.26-4.13 (2H, m), 3.91 (1H, t, J = 4.6 Hz), 2.97 (2H, t, J = 7.5 Hz), 2.41 (2H, t, J = 7.5 Hz), 1.89-1.63 (3H, m), 1.56 (9H, s), 1.01 (6H, dd, J = 7.7, 6.2 Hz). |
| 42 | Cyclopentyl N-{4-[3-(hydroxyamino)-3-oxopropyl]benzyl}-L-valinate | B, M1 | LCMS purity 100%, m/z = 363 [M + H]+, 1H NMR (300 MHz, d6-DMSO) δ: 10.38 (1H, s), 9.23 (1H, br s), 8.71 (1H, br s), 7.38 (2H, d, J = 7.7 Hz), 7.27 (2H, d, J = 7.7 Hz), 5.13 (1H, t, J = 5.4 Hz), 4.17-4.08 (2H, m), 3.86 (1H, br s), 2.83 (2H, t, J = 7.5 Hz), 2.54-2.53 (1H, m), 2.46-2.36 (1H, m), 2.27 (2H, t, J = 7.6 Hz), 1.91-1.76 (2H, m), 1.67-1.52 (6H, m), 1.01 (3H, d, J = 7.0 Hz), 0.91 (3H, d, J = 6.8 Hz). |
| 43 | Cyclopentyl N-{4-[3-(hydroxyamino)-3-oxopropyl]benzyl}-3-methyl-L-valinate | B, U | LCMS purity 96%, m/z = 377 [M + H]+, 1H NMR (300 MHz, CD3OD) δ: 7.44-7.32 (4H, m), 5.14-5.05 (1H, m), 4.32-4.17 (2H, m), 3.53 (1H, s), 2.98 (2H, t, J = 7.6 Hz), 2.41 (2H, t, J = 7.5 Hz), 1.94-1.61 (8H, m), 1.08 (9H, s). |
| 44 | tert-Butyl N-{4-[3-(hydroxyamino)-3-oxopropyl]benzyl}isoleucinate | B, N | LCMS purity 92%, m/z = 365 [M + H]+, 1H NMR (300 MHz, CD3OD) δ: 7.46-7.32 (4H, m), 4.22 (2H, s), 3.86 (1H, d, J = 3.2 Hz), 2.97 (2H, t, J = 7.5 Hz), 2.41 (2H, t, J = 7.5 Hz), 2.04-1.97 (1H, m), 1.52 (9H, s), 1.65-1.38 (2H, m), 1.03-0.98 (6H, m). |

-continued

| Example | Chemical name | Intermediates used | Analytical data |
|---|---|---|---|
| 45 | (1R,2S,5R)-2-Isopropyl-5-methylcyclohexyl N-{4-[3-(hydroxyamino)-3-oxopropyl]benzyl}-L-leucinate | B, K7 | LCMS purity 97%, m/z = 447 [M + H]$^+$, $^1$H NMR (300 MHz, CD$_3$OD) δ: 0.94 (3H, d, J = 5.1 Hz), 0.98 (14H, m), 1.51 (2H, m), 1.72-1.92 (6H, m), 2.04 (1H, m), 2.41 (2H, t, J = 7.5 Hz), 2.97 (2H, t, J = 7.5 Hz), 4.02 (1H, m), 4.18 (2H, dd, J = 36.6, 12.9 Hz), 7.37 (4H, m). |
| 46 | (1R,2S,5R)-2-Isopropyl-5-methylcyclohexyl (2S)-cyclohexyl({4-[3-(hydroxyamino)-3-oxopropyl]benzyl}amino)acetate | B, J13 | LCMS purity 98%, m/z = 473 [M + H]$^+$, $^1$H NMR (300 MHz, CD$_3$OD) δ: 0.72 (3H, d, J = 7.2 Hz), 0.8-1.9 (26H, m), 2.29 (2H, t, J = 7.8 Hz), 2.85 (2H, t, J = 7.8 Hz), 3.54 (1H, m), 4.01 (2H, m), 4.89 (1H, m), 7.25 (1H, m). |
| 47 | tert-Butyl N-{4-[3-(hydroxyamino)-3-oxopropyl]benzyl}-L-valinate | B, M2 | LCMS purity 100%, m/z = 351 [M + H]$^+$, $^1$H NMR (300 MHz, d$_6$-DMSO) δ: 10.41 (1H, s), 9.27 (2H, br s), 7.39 (2H, d, J = 8.1 Hz), 7.27 (2H, d, J = 7.9 Hz), 4.18-4.03 (2H, m), 3.74 (1H, br s), 2.83 (2H, t, J = 7.6 Hz), 2.36-2.32 (1H, m), 2.27 (2H, t), 1.43 (9H, s), 1.04 (3H, d, J = 7.0 Hz), 0.93 (3H, d, J = 6.8 Hz). |
| 48 | (1S,2R,5S)-2-Isopropyl-5-methylcyclohexyl (2S)-cyclohexyl({4-[3-(hydroxyamino)-3-oxopropyl]benzyl}amino)acetate | B, J12 | LCMS purity 98%, m/z = 473 [M + H]$^+$, $^1$H NMR (300 MHz, d$_6$-DMSO) δ: 10.37 (1H, br s), 8.70 (1H, br s), 7.15-7.43 (4H, m), 4.61-4.74 (1H, m), 4.00-4.23 (1H, m), 3.22-3.45 (2H, m), 2.82 (2H, t, J = 6.6 Hz), 2.26 (2H, t, J = 7.7 Hz), 1.33-2.01 (15H, m), 0.94-1.30 (14H, m), 0.90 (3H, d, J = 6.6 Hz), 0.88 (3H, d, J = 4.2 Hz), 0.71 (3H, d, J = 6.9 Hz). |
| 49 | tert-Butyl (2S)-({3-[3-(hydroxyamino)-3-oxopropyl]benzyl}amino)(phenyl)acetate | D, L2 | LCMS purity 98%, m/z = 485 [M + H]$^+$, $^1$H NMR (300 MHz, d$_6$-DMSO) δ: 10.39 (1H, br s), 7.48-7.55 (5H, m), 7.23-7.39 (4H, m), 5.13 (1H, br s), 3.99 (2H, ABq, J = 13.2 Hz), 2.82 (2H, t, J = 8.1 Hz), 2.26 (2H, t, J = 8.0 Hz), 1.35 (9H, s). |
| 50 | Cyclopentyl (2S)-cyclohexyl({3-[3-(hydroxyamino)-3-oxopropyl]benzyl}amino)acetate | D, J1 | LCMS purity 98%, m/z = 403 [M + H]$^+$, $^1$H NMR (300 MHz, d$_6$-DMSO) δ: 10.40 (1H, br s), 7.23-7.40 (4H, m), 5.16 (1H, m), 4.11 (2H, m), 3.82 (1H, br s), 2.83 (2H, t, J = 8.3 Hz), 2.27 (2H, t, J = 7.5 Hz), 0.73-2.00 (19H, m). |
| 51 | Cyclopentyl (2S)-({3-[3-(hydroxyamino)-3-oxopropyl]benzyl}amino)(phenyl)acetate | D, L1 | LCMS purity 98%, m/z = 397 [M + H]$^+$, $^1$H NMR (300 MHz, d$_6$-DMSO) δ: 10.39 (1H, br s), 7.51 (4H, m), 7.23-7.38 (5H, m), 5.15-5.23 (2H, m), 4.00 (2H, ABq, J = 12.3 Hz), 2.82 (2H, t, J = 8.1 Hz), 2.27 (2H, t, J = 7.4 Hz), 1.27-1.90 (8H, m). |
| 52 | Cyclopentyl N-{3-[3-(hydroxyamino)-3-oxopropyl]benzyl}-L-leucinate | D, K1 | LCMS purity 95%, m/z = 377 [M + H]$^+$, $^1$H NMR (300 MHz, d$_6$-DMSO) δ: 10.41 (1H, br s), 9.46 (1H, br s), 7.24-7.41 (4H, m), 5.21 (1H, t, J = 5.5 Hz), 4.13 (1H, ABq, J = 12.2 Hz), 3.93 (1H, m), 2.83 (2H, t, J = 7.2 Hz), 2.27 (2H, t, J = 8.0 Hz), 1.53-1.95 (11H, m), 0.90 (6H, d, J = 5.8 Hz). |
| 53 | Cyclopentyl (2S)-cyclohexyl[({6-[(1E)-3-(hydroxyamino)-3-oxoprop-1-en-1-yl]pyridin-3-yl}methyl)amino]acetate | E, J1 | LCMS purity >95%, m/z = 402 [M + H]$^+$, $^1$H NMR (300 MHz, CD$_3$OD) δ: 8.53 (1H, s), 7.89-7.48 (3H, m), 6.87 (1H, d, J = 15.6 Hz), 5.17 (1H, m), 3.77 (2H, q), 2.97 (1H, d, J = 6 Hz), 2.01-0.97 (19H, m). |
| 54 | Cyclopentyl N-({6-[(1E)-3-(hydroxyamino)-3-oxoprop-1-en-1-yl]pyridin-3-yl}methyl)-L-leucinate | E, K1 | LCMS purity 100%, m/z = 376 [M + H]$^+$, $^1$H NMR (300 MHz, CD$_3$OD) δ: 8.54 (1H, s), 7.87-7.49 (3H, m), 6.87 (1H, d, J = 15.6 Hz), 5.20 (1H, m), 3.78 (2H, q), 3.24 (1H, t), 2.00-1.20 (11H, m), 0.90 (6H, dd). |
| 55 | 2,3-Dihydro-1H-inden-2-yl (2S)-cyclohexyl[({6-[(1E)-3-(hydroxyamino)-3-oxoprop-1-en-1-yl]pyridin-3-yl}methyl)amino]acetate | E, J6 | LCMS purity 99%, m/z = 450 [M + H]$^+$, $^1$H NMR (300 MHz, CD$_3$OD) δ: 8.62 (1H, s), 7.87 (1H, d, J = 8.4 Hz), 7.64 (1H, d, J = 8.5 Hz), 7.60 (1H, s), 7.31-7.18 (5H, m), 6.97 (1H, d, J = 15.5 Hz), 5.59 (1H, m), 4.15 (2H, s), 1.88-1.58 (7H, m), 1.39-0.88 (9H, m). |

| Example | Chemical name | Intermediates used | Analytical data |
|---|---|---|---|
| 56 | 2-Morpholin-4-ylethyl (2S)-cyclohexyl[({6-[(1E)-3-(hydroxyamino)-3-oxoprop-1-en-1-yl]pyridin-3-yl}methyl)amino]acetate | E, J10 | LCMS purity 96%, m/z = 447 [M + H]$^+$, $^1$H NMR (300 MHz, CD$_3$OD) δ: 8.72 (1H, s), 8.02 (1H, dd, J = 7.9, 1.8 Hz), 7.66 (1H, d, J = 5.6 Hz), 7.65 (1H, d, J = 29.1 Hz), 6.99 (1H, d, J = 15.4 Hz), 4.64 (2H, m), 4.36 (2H, s), 4.10 (1H, d, J = 3.8 Hz), 3.97 (4H, br s), 3.60 (2H, m) 3.40 (3H, br s), 3.36 (3H, s), 2.07 (1H, m), 1.84 (4H, br s), 1.73 (1H, d, J = 11.1 Hz), 1.42-1.02 (5H, m). |
| 57 | 2-(Dimethylamino)ethyl (2S)-cyclohexyl[({6-[(1E)-3-(hydroxyamino)-3-oxoprop-1-en-1-yl]pyridin-3-yl}methyl)amino]acetate | E, J11 | LCMS purity 94%, m/z = 405 [M + H]$^+$, $^1$H NMR (300 MHz, CD$_3$OD) δ: 8.74 (1H, s), 8.07 (1H, d, J7.63), 7.70 (1H, d, J = 7.82 Hz), 7.58 (1H, d, J = 15.35 Hz), 4.65 (2H, m), 4.41 (2H, s), 3.01 (6H, s), 2.12 (1H, m), 1.84 (4H, d, J = 7.91 Hz), 1.71 (1H, d, J = 11.87 Hz), 1.41-1.04 (5H, m). |
| 58 | Bicyclo[2.2.1]hept-2-yl (2S)-cyclohexyl[({6-[(1E)-3-(hydroxyamino)-3-oxoprop-1-en-1-yl]pyridin-3-yl}methyl)amino]acetate | E, J7 | LCMS purity 97%, m/z = 428 [M + H]$^+$, $^1$H NMR (300 MHz, CD$_3$OD) δ: 8.73 (1H, s), 8.05 (1H, d, J = 7.25 Hz), 7.68 (1H, d, J = 7.82 Hz), 7.56 (1H, d, J = 15.54 Hz), 6.97 (1H, d, J = 15.45 Hz), 4.67 (1H, dd, J = 24.63, 6.55 Hz), 4.36 (2H, m), 4.02 (1H, m), 2.40-0.94 (22H, m). |
| 59 | tert-Butyl (2S)-cyclohexyl[({6-[(1E)-3-(hydroxyamino)-3-oxoprop-1-en-1-yl]pyridin-3-yl}methyl)amino]acetate | E, J2 | LCMS purity 98%, m/z = 390 [M + H]$^+$, $^1$H NMR (300 MHz, d$_6$-DMSO) δ: 1.14 (6H, m), 1.41 (9H, s), 1.61 (4H, m), 1.79 (1H, m), 2.73 (1H, m), 3.32 (1H, m), 3.54 (1H, d, J = 13.8 Hz), 3.80 (1H, d, J = 13.8 Hz), 6.90 (1H, d, J = 15.3 Hz), 7.45 (1H, d, J = 15.3 Hz), 7.52 (1H, d, J = 7.8 Hz), 7.73 (1H, dm, J = 7.8 Hz), 8.51 (1H, s), 9.12 (1H, s), 10.90 (1H, s). |
| 60 | Cyclopentyl (2S)-[({6-[(1E)-3-(hydroxyamino)-3-oxoprop-1-en-1-yl]pyridin-3-yl}methyl)amino](phenyl)acetate | E, L1 | LCMS purity 98%, m/z = 396 [M + H]$^+$, $^1$H NMR (300 MHz, d$_6$-DMSO) δ: 10.97 (1H, br s), 8.59 (1H, s), 7.88 (1H, dd, J = 2.0, 7.9 Hz), 7.64 (1H, d, J = 8.0 Hz), 7.43-7.57 (6H, m), 6.96 (1H, d, J = 15.4 Hz), 5.31 (1H, br s), 5.11-5.20 (1H, m), 4.14 (2H, ABq, J = 13.6 Hz), 1.26-1.90 (8H, m). |
| 61 | tert-Butyl (2S)-[({6-[(1E)-3-(hydroxyamino)-3-oxoprop-1-en-1-yl]pyridin-3-yl}methyl)amino](phenyl)acetate | E, L2 | LCMS purity 98%, m/z = 384 [M + H]$^+$, $^1$H NMR (300 MHz, d$_6$-DMSO) δ: 8.76 (1H, br s), 7.88 (1H, dd, J = 2.1, 8.2 Hz), 7.64 (1H, d, J = 8.1 Hz), 7.41-7.70 (6H, m), 6.95 (1H, d, J = 15.4 Hz), 5.12-5.31 (2H, m), 4.02-4.21 (2H, m), 1.34 (9H, s). |
| 62 | Cyclopentyl (2S)-cyclohexyl[({6-[3-(hydroxyamino)-3-oxopropyl]pyridin-3-yl}methyl)amino]acetate | F, J1 | LCMS purity 93%, m/z = 404 [M + H]$^+$, $^1$H NMR (300 MHz, d$_6$-DMSO) δ: 10.41 (1H, s), 8.70 (1H, s), 8.34 (1H, s), 7.59 (1H, d, J = 6 Hz), 7.19 (1H, d, J = 7.8 Hz), 5.08 (1H, m), 3.80-3.41 (2H, q), 2.92 (2H, t, J = 7.2 Hz), 2.81 (1H, m), 2.37 (2H, t, J = 8.1 Hz), 1.91-0.87 (19H, m). |
| 63 | tert-Butyl (2S)-cyclohexyl[({6-[3-(hydroxyamino)-3-oxopropyl]pyridin-3-yl}methyl)amino]acetate | F, J2 | LCMS purity 92%, m/z = 392 [M + H]$^+$, $^1$H NMR (300 MHz, CD$_3$OD) δ: 8.65 (1H, d, J = 1.7 Hz), 8.03 (1H, dd, J = 8.1, 2.3 Hz), 7.56 (1H, d, J = 8.1 Hz), 4.37-4.23 (2H, m), 3.87 (1H, d, J = 3.6 Hz), 3.18 (2H, t, J = 7.4 Hz), 2.59 (2H, t, J = 7.4 Hz), 2.05-1.97 (1H, m), 1.89-1.75 (5H, m), 1.54 (9H, s), 1.45-1.24 (3H, m), 1.23-1.04 (2H, m). |
| 64 | tert-Butyl (2S)-[({6-[3-(hydroxyamino)-3-oxopropyl]pyridin-3-yl}methyl)amino](phenyl)acetate | F, L2 | LCMS purity 98%, m/z = 386 [M + H]$^+$, $^1$H NMR (300 MHz, d$_6$-DMSO) δ: 10.43 (1H, br s), 10.13 (1H, br s), 8.49 (1H, s), 7.80 (1H, d, J = 7.2 Hz), 7.51 (5H, m), 7.38 (1H, t, J = 6.3 Hz), 5.21 (1H, br s), 4.06 (2H, ABq, J = 13.2 Hz), 2.99 (2H, t, J = 6.9 Hz), 2.68 (2H, t, J = 7.3 Hz), 2.40 (2H, t, J = 7.8 Hz), 1.35 (9H, s). |

-continued

| Example | Chemical name | Intermediates used | Analytical data |
|---|---|---|---|
| 65 | Cyclopentyl (2S)-[({6-[3-(hydroxyamino)-3-oxopropyl]pyridin-3-yl}methyl)amino](phenyl)acetate | F, L1 | LCMS purity 95%, m/z = 398 [M + H]$^+$, $^1$H NMR (300 MHz, d$_6$-DMSO) δ: 10.42 (1H, br s), 10.10 (1H, br s), 8.49 (1H, s), 7.88 (1H, d, J = 8.3 Hz), 7.45-7.60 (5H, m), 7.37 (1H, t, J = 6.4 Hz), 5.20 (1H, br s), 5.16 (1H, t, J = 5.7 Hz), 4.08 (2H, ABq, J = 15.4 Hz), 3.00 (2H, t, J = 7.6 Hz), 2.42 (2H, t, J = 7.6 Hz), 1.27-1.87 (8H, m). |
| 66 | tert-Butyl N-({6-[3-(hydroxyamino)-3-oxopropyl]pyridin-3-yl}methyl)-L-leucinate | F, K2 | LCMS purity 97%, m/z = 366 [M + H]$^+$, $^1$H NMR (300 MHz, CD$_3$OD) δ: 8.29 (1H, dd, J = 1.8, 0.7 Hz), 7.63 (1H, dt, J = 8.1, 1.1 Hz), 7.21 (1H, d, J = 8.1 Hz), 3.69 (1H, d, J = 13.4 Hz), 3.52 (1H, d, J = 13.4 Hz), 3.02 (1H, t), 2.96 (2H, dd, J = 8.1, 7.5 Hz), 2.34 (2H, t, J = 7.8 Hz), 1.69-1.56 (1H, m), 1.38 (9H, s), 0.82 (3H, d, J = 6.6 Hz), 0.76 (3H, d, J = 6.6 Hz). |
| 67 | (1R,2S,5R)-2-Isopropyl-5-methylcyclohexyl N-({6-[3-(hydroxyamino)-3-oxopropyl]pyridin-3-yl}methyl)-L-leucinate | F, K7 | LCMS purity 97%, m/z = 448 [M + H]$^+$, $^1$H NMR (300 MHz, d$_6$-DMSO) δ: 10.44 (1H, s), 9.60 (1H, br s), 8.54 (1H, d, J = 1.9 Hz), 7.81 (1H, dd, J = 8.1, 2.1 Hz), 7.43-7.35 (1H, m), 4.82-4.71 (1H, m), 4.03 (3H, q, J = 7.2 Hz), 2.99 (1H, t, J = 7.6 Hz), 2.71 (1H, d, J = 13.6 Hz), 2.41 (1H, t, J = 7.6 Hz), 1.93-1.76 (2H, m), 1.74-1.62 (6H, m), 1.43 (2H, t, J = 12.4 Hz), 1.18 (6H, t, J = 7.2 Hz), 1.06 (2H, t, J = 11.5 Hz), 0.91 (8H, dd, J = 6.9, 2.7 Hz), 0.74 (3H, d, J = 7.0 Hz). |
| 68 | Cyclopentyl (2S)-cyclohexyl[({5-[(1E)-3-(hydroxyamino)-3-oxoprop-1-en-1-yl]pyridin-2-yl}methyl)amino]acetate | G, J1 | LCMS purity 95%, m/z = 402 [M + H]$^+$, $^1$H NMR (300 MHz, CD$_3$OD) δ: 8.81 (1H, s), 8.09 (1H, d, J = 7.7 Hz), 7.63 (1H, d, J = 15.9 Hz), 7.50 (1H, d, J = 8.2 Hz), 5.31-5.39 (1H, m), 4.46 (2H, ABq, J = 13 Hz), 3.98 (1H, d, J = 4.0 Hz), 1.07-2.14 (18H, m). |
| 69 | tert-Butyl N-({5-[(1E)-3-(hydroxyamino)-3-oxoprop-1-en-1-yl]pyridin-2-yl}methyl)-L-leucinate | G, K2 | LCMS purity 98%, m/z = 364 [M + H]$^+$, $^1$H NMR (300 MHz, d$_6$-DMSO) δ: 10.87 (1H, br s), 9.55 (2H, br s), 9.14 (1H, br s), 8.84 (1H, s), 8.10 (1H, d, J = 8.4 Hz), 7.50-7.60 (2H, m), 6.62 (1H, d, J = 15.7 Hz), 4.35 (2H, ABq, J = 16.4 Hz), 3.84-3.99 (2H, m), 1.64-1.78 (3H, m), 1.46 (9H, s), 0.93 (6H, d, J = 5.8 Hz). |
| 70 | Cyclopentyl (2S)-cyclohexyl[({5-[3-(hydroxyamino)-3-oxopropyl]pyridin-2-yl}methyl)amino]acetate | H, J1 | LCMS purity 95%, m/z = 404 [M + H]$^+$, $^1$H NMR (300 MHz, d$_6$-DMSO) δ: 10.41 (1H, br s), 8.48 (1H, d, J = 1.6 Hz), 7.73 (1H, dd, J = 2.1, 8.0 Hz), 7.44 (1H, d, J = 8.0 Hz), 5.19 (1H, t, J = 5.5 Hz), 4.30 (2H, br s), 3.88 (2H, t, J = 3.6 Hz), 2.87 (2H, t, J = 7.3 Hz), 2.31 (2H, t, J = 7.4 Hz), 1.53-2.07 (14H, m), 0.79-1.31 (5H, m). |
| 71 | tert-Butyl N-({5-[3-(hydroxyamino)-3-oxopropyl]pyridin-2-yl}methyl)-L-leucinate | H, K2 | LCMS purity 99%, m/z = 366 [M + H]$^+$, $^1$H NMR (300 MHz, d$_6$-DMSO) δ: 10.37 (1H, br s), 8.73 (1H, br s), 8.31 (1H, d, J = 1.8 Hz), 7.56 (1H, dd, J = 8.1, 2.2 Hz), 7.31 (1H, d, J = 8.1 Hz), 3.76 (1H, d, J = 13.6 Hz), 3.62 (1H, dd, J = 2.9, 14.0 Hz), 3.03-3.11 (1H, m), 2.80 (2H, t, J = 7.5 Hz), 2.30-2.45 (1H, m), 2.26 (2H, t, J = 7.3 Hz), 1.66-1.79 (1H, m), 1.40 (9H, s), 0.88 (3H, d, J = 7.0 Hz), 0.82 (3H, d, J = 6.5 Hz). |

Example 72

Cyclopentyl N-{4-[(1E)-3-(hydroxyamino)-3-oxo-prop-1-en-1-yl]benzyl}-D-serinate

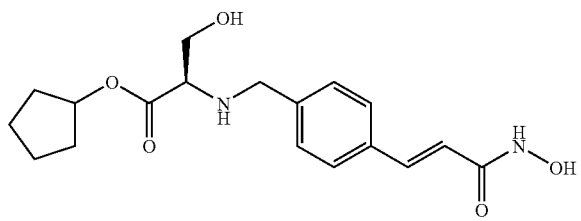 [SMILES: O=C(/C=C/c1ccc(CN[C@H](CO)C(=O)OC2CCCC2)cc1)NO]

The title compound was prepared by the following methodology:

Stage 1—Preparation of cyclopentyl N-{4-[(1E)-3-(hydroxyamino)-3-oxoprop-1-en-1-yl]benzyl}-D-serinate (Example 72)

The intermediate in the preparation of Example 20 (100 mg, 0.20 mmol) was dissolved in DCM (10 mL) and 4N HCl in dioxane (0.15 mL, 0.60 mmol) charged. The reaction was concentrated to dryness, the residue dissolved in THF (10 mL), 1N aqueous HCl (10 mL) was charged and the reaction stirred at 50° C. for 18 h. The solvent was then removed in vacuo and the residue purified by prep HPLC to afford the desired product (12 mg, 17%). LCMS purity 100%, m/z=349 [M+H]+, 1H NMR (300 MHz, CD3OD) δ: 7.80-7.44 (5H, m), 6.55 (1H, d, J=15.3 Hz), 5.33 (1H, s), 4.32 (2H, s), 4.06 (3H, s), 2.03-1.20 (8H, m).

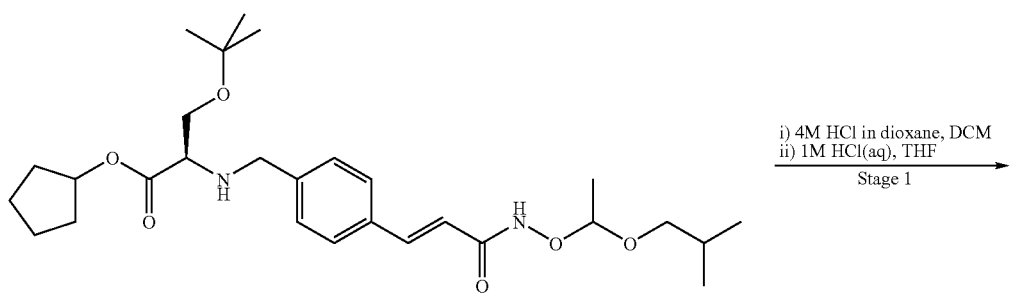

Intermediate in the preparation of Example 20

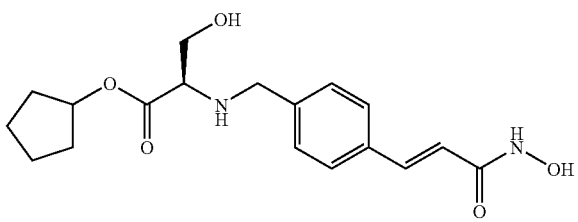

Example 72

Example 73
Cyclopentyl (2S)-cyclohexyl({4-[({3-[(1E)-3-(hydroxyamino)-3-oxoprop-1-en-1-yl]benzyl}amino)methyl]benzyl}amino)acetate
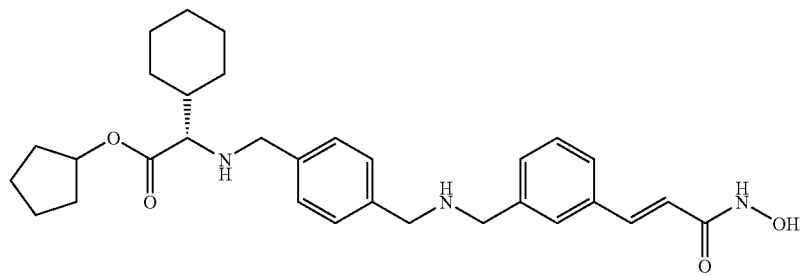 [SMILES: O=C(/C=C/c1cccc(CNCc2ccc(CN[C@H](C(=O)OC3CCCC3)C3CCCCC3)cc2)c1)NO]
The title compound was prepared by the following methodology:
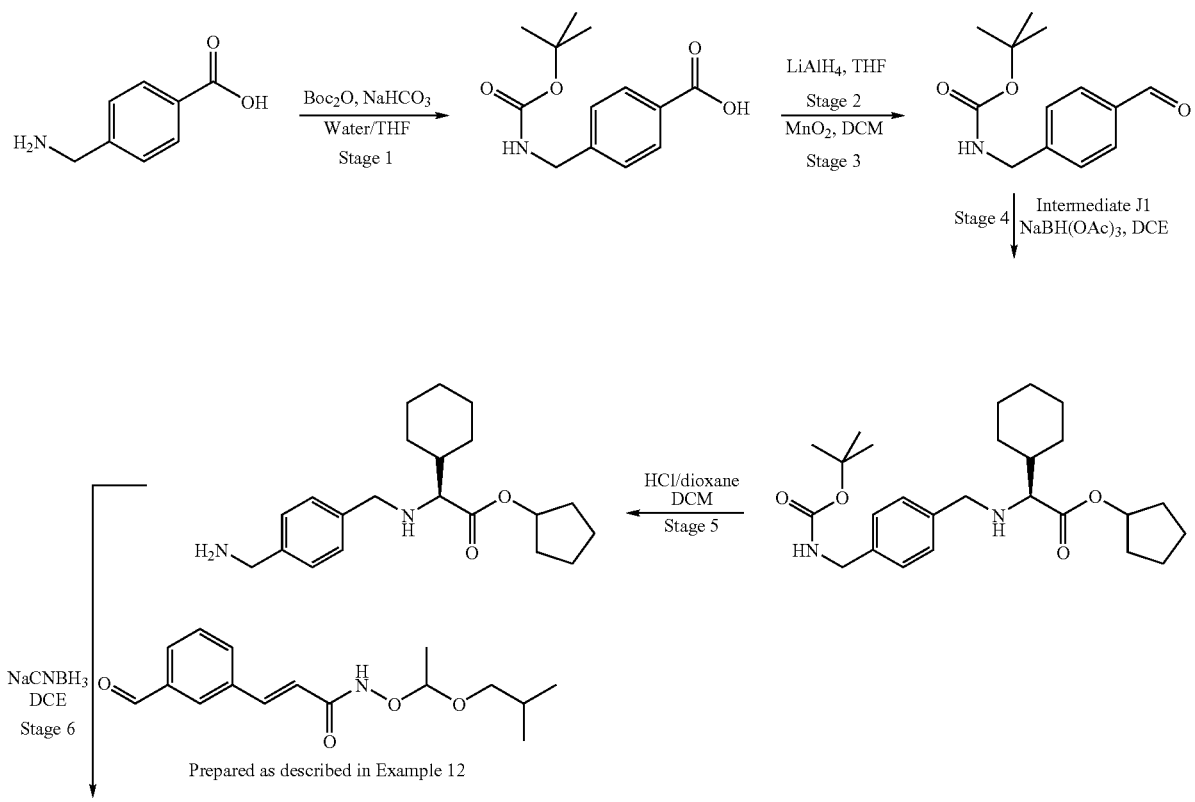
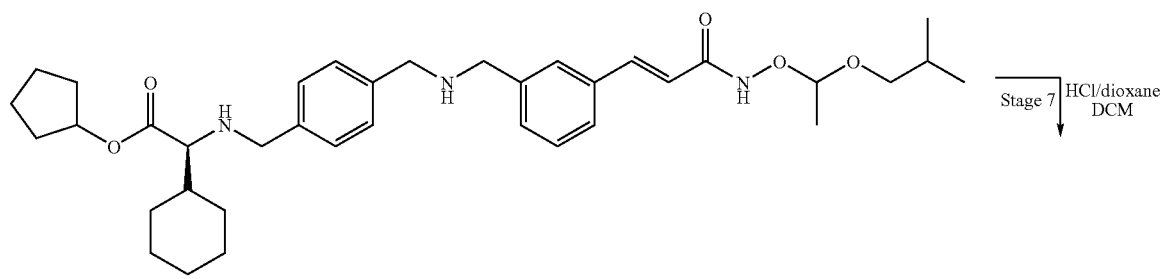

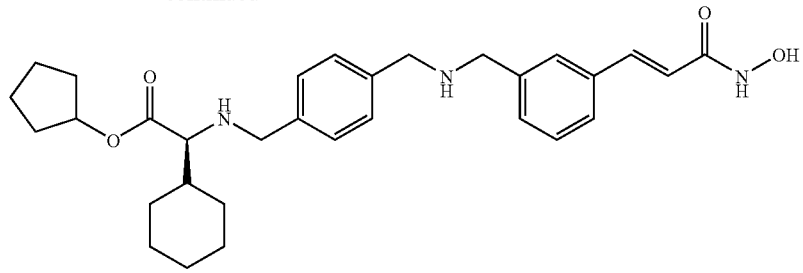

Example 73

Stage 1—Preparation of 4-{[(tert-butoxycarbonyl)amino]methyl}benzoic acid 4-(Aminomethyl)benzoic acid (10.00 g, 65.36 mmol) was stirred with Boc$_2$O (28.00 g, 130.72 mmol) in H$_2$O (100 mL) and THF (100 mL) at RT. Sat. NaHCO$_3$ solution was added until pH~6 was reached and the reaction was allowed to stir for 16 h. The reaction was then carefully acidified to pH~3 with 1M HCl$_{aq}$ which caused a solid to precipitate out. This was filtered and dried to give the product as a white solid (16.1 g, 97%). m/z=274 [M+Na]$^+$.

Stage 2—Preparation of tert-butyl [4-(hydroxymethyl)benzyl]carbamate

Stage 1 product (16.1 g, 64.14 mmol) was stirred in THF (300 mL) and dioxane (200 mL) at 0° C. under a nitrogen atmosphere. LiAlH$_4$ was then added and the reaction allowed to warm to RT and stir for 16 h. It was then cooled to 0° C. and quenched with sat. NH$_4$Cl$_{aq}$. Na$_2$SO$_4$ was added and the mixture stirred for 30 minutes. It was then filtered through celite and the filtrate concentrated in vacuo to give the product as a light yellow solid (13.1 g, 94%). m/z=260 [M+Na]$^+$.

Stage 3—Preparation of tert-butyl (4-formylbenzyl)carbamate

Stage 2 product (5.87 g, 24.73 mmol) was stirred in DCM (200 mL) with MnO$_2$ (16.71 g, 192.2 mmol) for 16 h at RT. The reaction was then filtered through celite and the solvent removed in vacuo to give the product as a yellow oil (4.63 g, 80%). m/z=258 [M+Na]$^+$.

Stage 4—Preparation of cyclopentyl (2S)-[(4-{[(tert-butoxycarbonyl)amino]methyl}benzyl)amino](cyclohexyl)acetate Stage 3 product (650 mg, 2.70 mmol) was stirred in DCE (20 mL), Intermediate J1 (707 mg, 2.70 mmol) and STAB (918 mg, 4.33 mmol) at RT under a nitrogen atmosphere for 3 h. After this time the reaction was diluted with H$_2$O (50 mL) and extracted with Et$_2$O (2×100 mL). The combined organic extracts were dried (MgSO$_4$) and solvent removed in vacuo to give the product as a brown oil (1.13 g, 95%). m/z=445 [M+H]$^+$.

Stage 5—Preparation of cyclopentyl (2S)-{[4-(aminomethyl)benzyl]amino}(cyclohexyl)acetate Stage 4 product (1.13 g, 2.56 mmol) was stirred in DCM (5 mL) with 4M HCl in dioxane (2 mL) at RT under a nitrogen atmosphere for 3 h. The solvent was removed in vacuo and the residue dried to give the product as a brown solid as the HCl salt (971 mg, 99%). m/z=345 [M+H]$^+$.

Stage 6—Preparation of cyclopentyl (2S)-cyclohexyl [(4-{[(3-{(1E)-3-[(1-isobutoxyethoxy)amino]-3-oxoprop-1-en-1-yl}benzyl)amino]methyl}benzyl)amino]acetate (2E)-3-(3-Formylphenyl)-N-(1-isobutoxyethoxy)acrylamide (prepared as described in Example 12-0.2 g, 0.69 mmol) and stage 5 product (0.26 g, 0.68 mmol) were dissolved in DCE (10 mL) and stirred under nitrogen for 17 h. NaBH$_3$CN (0.087 g, 1.4 mmol) was charged and the reaction stirred for 2 h. After this time the reaction was quenched with water (10 mL) then separated. The aqueous phase was extracted with DCM (2×10 mL) and the combined organics dried (MgSO$_4$) and concentrated to dryness in vacuo to afford the product as a yellow oil. Purification by column chromatography (1:1 EtOAc in heptane) gave a pale yellow oil (0.07 g, 16%). m/z=642 [M+Na]$^+$.

Stage 7—Preparation of cyclopentyl (2S)-cyclohexyl ({4-[({3-[(1E)-3-(hydroxyamino)-3-oxoprop-1-en-1-yl]benzyl}amino)methyl]benzyl}amino)acetate (Example 73)

4N HCl in dioxane (0.03 mL, 0.12 mmol) was charged to a solution of stage 6 product (0.07 g, 0.11 mmol) in DCM (10 mL) and the reaction stirred for 3 h. The reaction was concentrated to dryness in vacuo to afford a yellow oil. Purification by preparative HPLC afforded the desired product as a white solid (15 mg, 26%). LCMS purity >95%, m/z=520 [M+H]$^+$, $^1$H NMR (300 MHz, CD$_3$OD) δ: 7.78-7.47 (9H, m), 6.54 (1H, d, J=15.6 Hz), 5.31 (1H, m), 4.38-4.20 (6H, m), 3.79 (1H, m), 2.04-1.18 (19H, m).

Example 74

Cyclopentyl O-tert-butyl-N-{4-[({3-[(1E)-3-(hydroxyamino)-3-oxoprop-1-en-1-yl]benzyl}amino)methyl]benzyl}-L-serinate

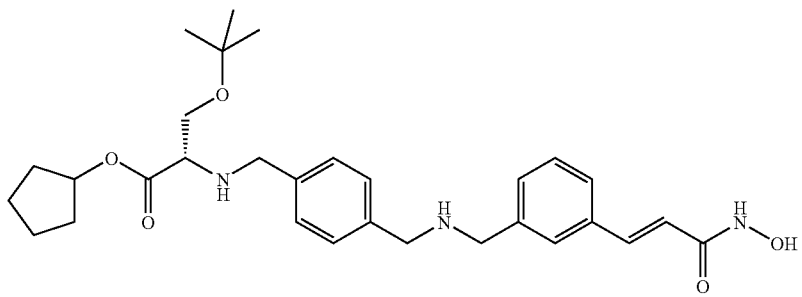 [SMILES: CC(C)(C)OC[C@H](NCc1ccc(CNCc2cccc(/C=C/C(=O)NO)c2)cc1)C(=O)OC1CCCC1]

The title compound was prepared from Intermediate O by the same methodology used to make Example 73.

LCMS purity 100%, m/z=520 [M+H]$^+$, $^1$H NMR (300 MHz, CD$_3$OD) δ: 7.78-7.47 (9H, m), 6.54 (1H, d, J=15.6 Hz), 5.31 (1H, m), 4.38-4.20 (6H, m), 3.79 (1H, m), 2.04-1.18 (19H, m).

Example 75

Cyclopentyl O-tert-butyl-N-{4-[({4-[(1E)-3-(hydroxyamino)-3-oxoprop-1-en-1-yl]benzyl}amino)methyl]benzyl}-L-serinate

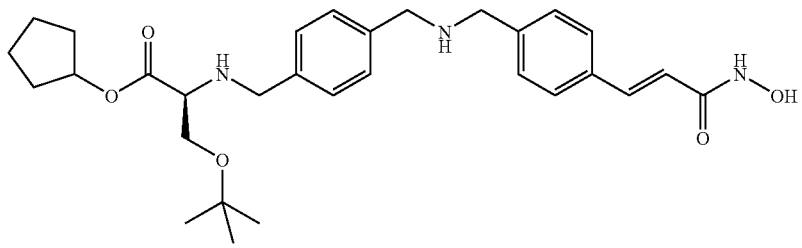 [SMILES: CC(C)(C)OC[C@H](NCc1ccc(CNCc2ccc(/C=C/C(=O)NO)cc2)cc1)C(=O)OC1CCCC1]

The title compound was prepared by the following methodology:

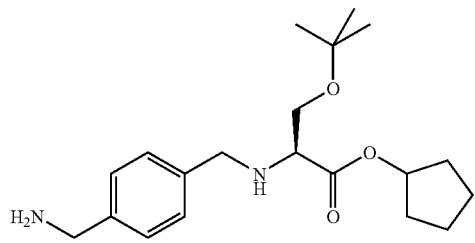

Prepared with Intermediate O using the same methodology as described in Example 73

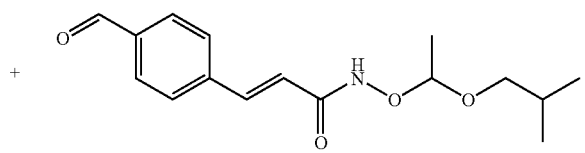

Prepared from Intermediate A using the same methodology as described in Example 12

Stage 1 | STAB DCE

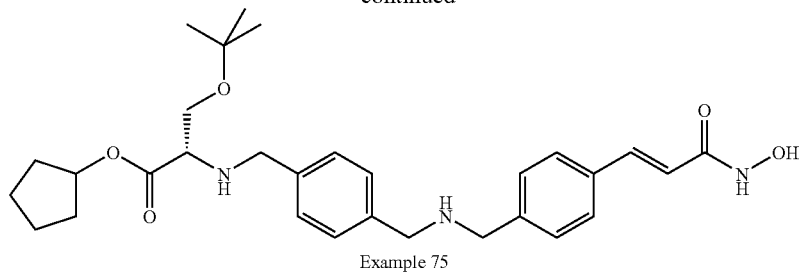

Example 75

Stage 1—Preparation of cyclopentyl O-tert-butyl-N-{4-[({4-[(1E)-3-(hydroxyamino)-3-oxoprop-1-en-1-yl]benzyl}amino)methyl]benzyl}-L-serinate (Example 75)

To a suspension of cyclopentyl N-[4-(aminomethyl)benzyl]-O-tert-butyl-L-serinate (prepared as described in Example 73-0.282 g, 0.67 mmol) and (2E)-3-(4-formylphenyl)-N-(1-isobutoxyethoxy)acrylamide (prepared as described in Example 12-0.230 g, 0.79 mmol) in DCE (25 mL) was added STAB (0.700 g, 3.3 mmol). The mixture was stirred at RT for 3 h, and then quenched with sat. NaHCO$_3$ solution (75 mL). The product was then extracted with DCM (3×100 mL) and the combined organic extracts were dried (MgSO$_4$), concentrated and purified by preparative HPLC to yield the desired product (5 mg, 2%). LCMS purity 98%, m/z=524.25 [M+H]$^+$, $^1$H NMR (300 MHz, CD$_3$OD) δ: 7.41 (2H, d, J=7.9 Hz), 7.24 (2H, d, J=7.7 Hz), 7.20 (3H, br s), 6.37 (1H, d, J=15.6 Hz), 5.09 (1H, t, J=5.7 Hz), 3.44-3.75 (8H, m), 3.25 (1H, t, J=3 Hz), 1.45-1.90 (8H, m), 1.04 (9H, s).

The following examples were prepared using the same methodology:

| Example | Chemical name | Intermediates used | Analytical data |
|---|---|---|---|
| 76 | tert-Butyl N-{4-[({4-[(1E)-3-(hydroxyamino)-3-oxoprop-1-en-1-yl]benzyl}amino)methyl]benzyl}-L-leucinate | A, K2 | LCMS purity 97%, m/z = 482 [M + H]$^+$, $^1$H NMR (300 MHz, d$_6$-DMSO) δ: 0.91 (6H, m), 1.47 (9H, s), 1.71 (3H, m), 3.81 (1H, m), 4.15 (6H, m), 6.52 (1H, d, J = 15.9 Hz), 7.50 (7H, m), 7.63 (2H, d, J = 8.4 Hz), 9.51 (3H, m), 10.85 (1H, s). |
| 77 | Cyclopentyl (2S)-cyclohexyl({4-[({4-[3-(hydroxyamino)-3-oxopropyl]benzyl}amino)methyl]benzyl}amino)acetate | B, J1 | LCMS purity 98%, m/z = 522 [M + H]$^+$, $^1$H NMR (300 MHz, CD$_3$OD) δ: 0.96-1.45 (6H, m), 1.75-2.00 (13H, m), 2.41 (2H, t, J = 7.2 Hz), 2.96 (2H, t, J = 7.2 Hz), 3.82 (1H, d, J = 3.9 Hz), 4.23 (2H, s), 4.29 (4H, s), 5.31 (1H, t, J = 5.7 Hz), 7.33 (2H, d, J = 8.1 Hz), 7.41 (2H, d, J = 8.1 Hz), 7.59 (4H, m). |
| 78 | tert-Butyl N-{4-[({4-[3-(hydroxyamino)-3-oxopropyl]benzyl}amino)methyl]benzyl}-L-leucinate | B, K2 | LCMS purity 97%, m/z = 484 [M + H]$^+$, $^1$H NMR (300 MHz, CD$_3$OD) δ: 1.01 (6H, t, J = 6.0 Hz), 1.57 (9H, s), 1.80 (3H, m), 2.41 (2H, t, J = 7.2 Hz), 2.96 (2H, t, J = 7.2 Hz), 3.95 (1H, m), 4.25 (6H, m), 7.32 (2H, d, J = 8.1 Hz), 7.42 (2H, d, J = 8.1 Hz), 7.61 (4H, s). |

Example 79
Cyclopentyl (2S)-cyclohexyl[({4-[({3-[(1E)-3-(hydroxyamino)-3-oxoprop-1-en-1-yl]benzyl}amino)methyl]cyclohexyl}methyl)amino]acetate
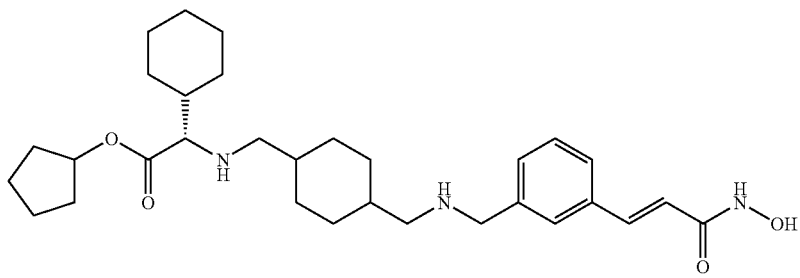 [SMILES: O=C(/C=C/c1cccc(CNCC2CCC(CN[C@H](C(=O)OC3CCCC3)C3CCCCC3)CC2)c1)NO]
The title compound was prepared by the following methodology:
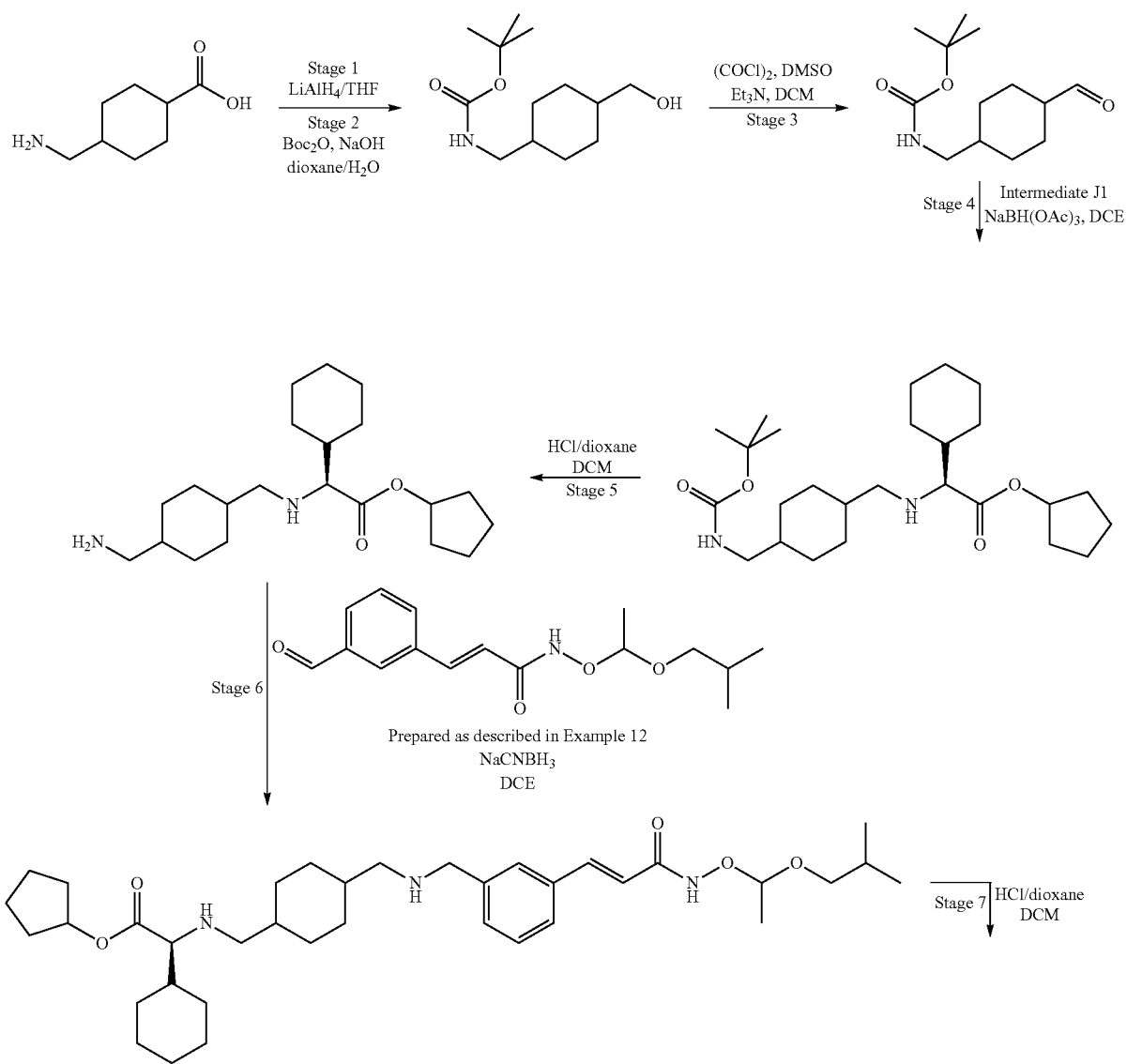

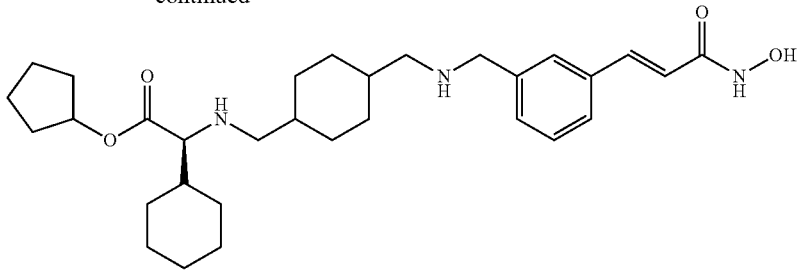

Example 79

Stage 1—Preparation of [4-(aminomethyl)cyclohexyl]methanol 4-(Aminomethyl)cyclohexanecarboxylic acid (4.00 g, 25.44 mmol) was stirred in THF (100 mL) at 0° C. under a nitrogen atmosphere. LiAlH$_4$ (2.90 g, 76.33 mmol) was then added and the reaction allowed to warm to RT and stir for 3 h. It was then cooled to 0° C. and quenched with H$_2$O, Na$_2$SO$_4$ was then added and the mixture stirred for 10 minutes. It was then filtered through celite and the filtrate concentrated in vacuo to give the product as a colourless oil which solidified on standing to give the product as a white solid (3.72 g, 100%). $^1$H NMR (300 MHz, d$_6$ DMSO) δ: 0.95 (4H, m), 1.22-1.47 (5H, m), 1.86 (4H, m), 2.55 (2H, d, J=6.6 Hz), 4.46 (2H, d, J=6.3 Hz).

Stage 2—Preparation of tert-butyl {[4-(hydroxymethyl)cyclohexyl]methyl}carbamate Stage 1 product (3.72 g, 26.01 mmol) was stirred with NaOH (1.00 g, 26.01 mmol) and di-tert-butyl-dicarbonate (6.24 g, 28.61 mmol) in H$_2$O (50 mL) and dioxane (50 mL) at RT for 16 h. The reaction was then concentrated in vacuo. When approximately 50% had been evaporated, a solid precipitated out of solution and was collected and dried to give the product as a white solid (5.5 g, 87%). m/z=266 [M+Na]$^+$, $^1$H NMR (300 MHz, CDCl$_3$) δ: 0.82 (4H, m), 1.28 (2H, m), 1.37 (9H, s), 1.70 (4H, m), 2.76 (2H, t, J=6.3 Hz), 3.19 (2H, d, J=6.3 Hz), 4.32 (1H, brs), 6.75 (1H, m).

Stage 3—Preparation of tert-butyl [(4-formylcyclohexyl)methyl]carbamate

A solution of DCM (100 mL) and (COCl)$_2$ (1.58 mL, 18.14 mmol) was stirred under a nitrogen atmosphere and cooled to −78° C. DMSO (2.27 mL, 32.02 mmol) was then added whilst maintaining the temperature below −65° C. A solution of stage 2 product (4.5 g, 17.79 mmol) in DCM (50 mL) was then prepared and added slowly to the reaction mixture, again maintaining the temperature below −65° C. When addition was complete Et$_3$N (9.99 mL, 71.69 mmol) was slowly added, again maintaining the temperature below −65° C. When addition was complete the reaction was allowed to warm to RT and then the solvent removed in vacuo. The residue was purified by column chromatography (0 to 10% MeOH in DCM) to give the product as a light yellow oil (5 g, >100%—contains some Et$_3$N). m/z=266 [M+Na]$^+$, $^1$H NMR (300 MHz, CDCl$_3$) δ: 1.02 (2H, m), 1.30 (2H, m), 1.45 (9H, s), 1.90 (2H, m), 2.03 (2H, m), 3.01 (2H, t, J=6.3 Hz), 4.57 (1H, brs), 9.63 (1H, s).

Stage 4—Preparation of cyclopentyl (2S)-{[(4-{[(tert-butoxycarbonyl)amino]methyl}cyclohexyl)methyl]amino}(cyclohexyl)acetate Stage 3 product (1.00 g, 4.14 mmol) was stirred with Intermediate J1 (1.08 g, 4.14 mmol) and STAB (1.33 g, 6.21 mmol) in DCE (20 mL) at RT for 16 h. The reaction was then diluted with H$_2$O (100 mL) and extracted with DCM (2×100 mL). The combined organic extracts were dried (MgSO$_4$) and the solvent removed in vacuo to give the product as a grey solid which was used in the next step without further purification (1.74 g, 94%). m/z=451 [M+H]$^+$.

Stage 5—Preparation of cyclopentyl (2S)-({[4-(aminomethyl)cyclohexyl]methyl}amino) (cyclohexyl)acetate Stage 4 product (1.74 g, 3.87 mmol) was stirred in DCM (10 mL) with 4M HCl in dioxane (3 mL) at RT for 16 h. The solvent was then removed in vacuo and the residue dried under vacuum to give the product as a white solid (1.36 g, 98%). m/z=351 [M+H]$^+$, $^1$H NMR (300 MHz, d$_6$-DMSO) δ: 0.90-1.20 (9H, m), 1.50-2.00 (21H, m), 2.65 (4H, m), 3.85 (1H, m), 5.25 (1H, m), 7.83 (2H, m).

Stage 6—Preparation of cyclopentyl (2S)-cyclohexyl{[(4-{[(3-{(1E)-3-[(1-isobutoxyethoxy)amino]-3-oxoprop-1-en-1-yl}benzyl)amino]methyl}cyclohexyl)methyl]amino}acetate (2E)-3-(3-Formylphenyl)-N-(1-isobutoxyethoxy)acrylamide (prepared as described in Example 12-0.3 g, 1 mmol) and stage 5 product (0.40 g, 1 mmol) were dissolved in DCE (10 mL) and stirred for 2 h. NaBH$_3$CN (0.13 g, 2.1 mmol) was charged and the reaction stirred for 15 h. After this time the reaction was quenched with water (10 mL) then separated. The aqueous phase was extracted with DCM (2×10 mL) and the combined organics dried (MgSO$_4$) and concentrated to dryness in vacuo to afford the product as a yellow oil (0.91 g, 143%). m/z=626 [M+H]$^+$.

Stage 7—Preparation of cyclopentyl (2S)-cyclohexyl [({4-[({3-[(1E)-3-(hydroxyamino)-3-oxoprop-1-en-1-yl]benzyl}amino)methyl]cyclohexyl}methyl)amino]acetate (Example 79)

4N HCl in dioxane (0.52 mL, 2 mmol) was charged to a solution of stage 6 product (0.65 g, 1 mmol) in DCM (10 mL) and the reaction stirred for 5 minutes. The reaction was concentrated to dryness in vacuo to afford a yellow oil. Purification by preparative HPLC afforded the desired product as a white solid (20 mg, 4%). LCMS purity >95%, m/z=526

[M+H]+, 1H NMR (300 MHz, CD3OD) δ: 7.80-7.42 (5H, m), 6.56 (1H, d, J=15.6 Hz), 5.36 (1H, m), 4.26 (1H, s), 3.85 (1H, d), 3.12-2.75 (4H, m), 2.12-0.87 (29H, m).
Example 80
Cyclopentyl (2S)-cyclohexyl[(1-{4-[(1E)-3-(hydroxyamino)-3-oxoprop-1-en-1-yl]benzyl}piperidin-4-yl)amino]acetate
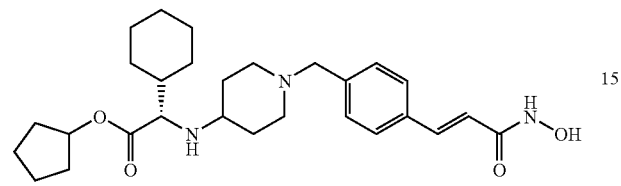
The title compound was prepared by the following methodology:

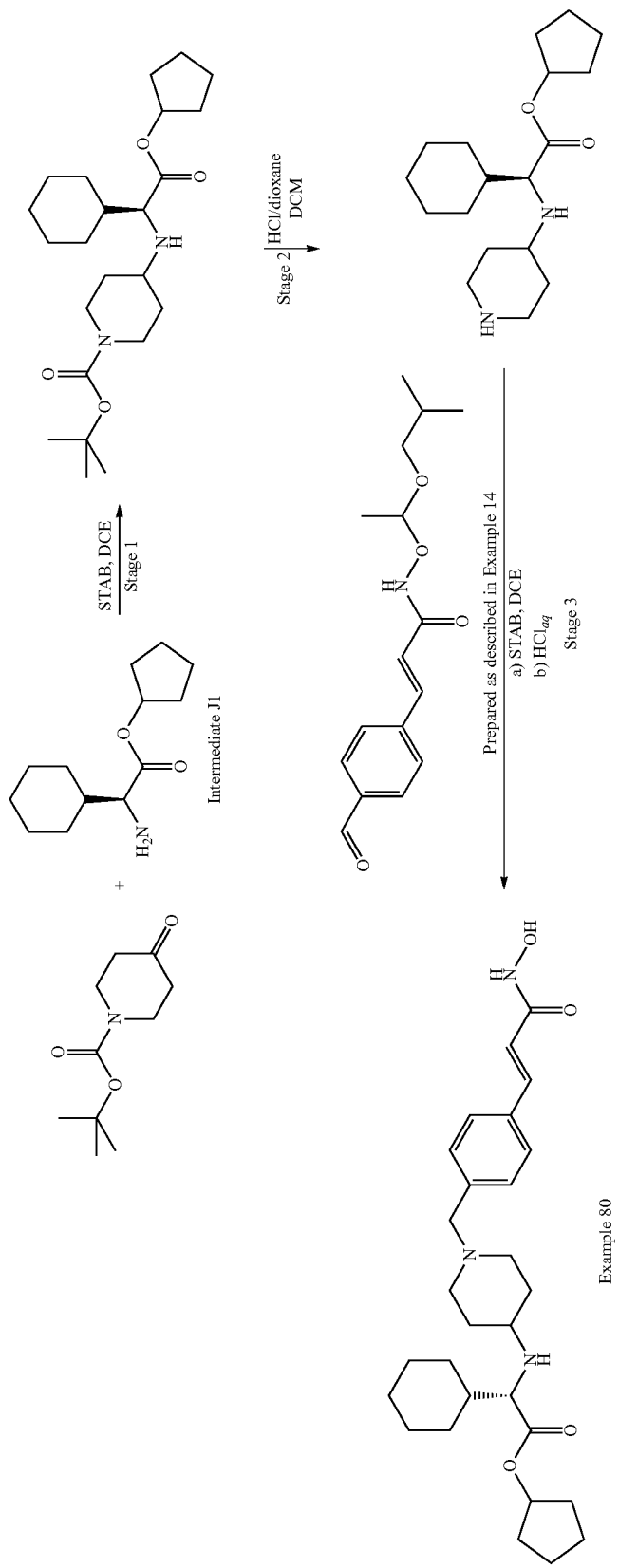

Stage 1—Preparation of tert-butyl 4-{[(1S)-1-cyclohexyl-2-(cyclopentyloxy)-2-oxoethyl]amino}piperidine-1-carboxylate To a solution of Intermediate J1 (1.15 g, 4.4 mmol) in DCE (20 mL) was added tert-butyl 4-oxopiperidine-1-carboxylate (800 mg, 4.01 mmol) and STAB (1.73 g, 8.2 mmol). The mixture was stirred for 4 h and then quenched by addition of sat. NaHCO$_3$ solution (50 mL). The product was extracted with DCM (2×50 mL), and the combined extracts were dried (MgSO$_4$) and concentrated, and then purified by column chromatography (1% MeOH in DCM) to yield the desired product (1.05 g, 61%). m/z=409.25 [M+H]$^+$, $^1$H NMR (300 MHz, CDCl$_3$) δ: 5.32 (1H, s), 5.22-5.25 (1H, m), 3.87-4.00 (2H, m), 3.50 (1H, d, J=4.3 Hz), 3.06 (1H, t, J=5.3 Hz), 2.81-2.94 (2H, m), 2.46-2.57 (1H, m), 0.91-1.95 (23H, m), 1.46 (9H, s).

Stage 2—Preparation of cyclopentyl (2S)-cyclohexyl(piperidin-4-ylamino)acetate di-hydrochloride To stage 1 product (1.058 g, 2.4 mmol) in DCM (2 mL) was added 4M HCl in dioxane (5 mL). The mixture was stirred for 2 h, and then Et$_2$O (50 mL) was added to induce precipitation. The product was collected by filtration to give an off white solid (952 mg, quant.). m/z=309.25 [M+H]$^+$.

Stage 3—Preparation of cyclopentyl (2S)-cyclohexyl[(1-{4-[(1E)-3-(hydroxyamino)-3-oxoprop-1-en-1-yl]benzyl}piperidin-4-yl)amino]acetate (Example 80)

To a solution of stage 2 product (0.396 g, 1.03 mmol) in DCE (5 mL) was added (2E)-3-(4-formylphenyl)-N-(1-isobutoxyethoxy)acrylamide (prepared as described in Example 14-0.324 g, 1.11 mmol) in DCE (5 mL). STAB (0.325 g, 1.53 mmol) was then added, and the mixture was stirred for 3 h. The reaction was quenched by addition of 2M HCl (10 mL), and stirred for 30 minutes. The mixture was then poured into sat. NaHCO$_3$ solution (100 mL), and the product extracted with DCM (3×75 mL). The mixture was then dried (MgSO$_4$), concentrated and purified by preparative HPLC to yield the desired product (35 mg, 7%). LCMS purity >98%, m/z=488 [M+H]$^+$, $^1$H NMR (300 MHz, CD$_3$OD) δ: 7.48-7.65 (3H, m), 7.36 (2H, d, J=7.8 Hz), 6.48 (1H, d, J=15.7 Hz), 5.20 (1H, m), 3.45-3.65 (6H, m), 3.30-3.35 (2H, m), 2.87 (2H, d, J=11.5 Hz), 2.50 (1H, m), 1.30-2.15 (12H, m), 1.16 (9H, s).

Example 81

Cyclopentyl O-tert-butyl-N-(1-{4-[(1E)-3-(hydroxyamino)-3-oxoprop-1-en-1-yl]benzyl}piperidin-4-yl)-L-serinate

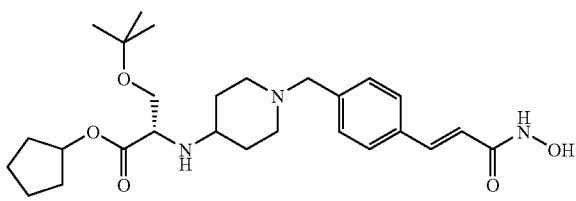 [SMILES: CC(C)(C)OC[C@H](NC1CCN(Cc2ccc(/C=C/C(=O)NO)cc2)CC1)C(=O)OC1CCCC1]

The title compound was prepared from Intermediate O by the same methodology used to make Example 80.
LCMS purity >98%, m/z=488.25 [M+H]$^+$, $^1$H NMR (300 MHz, d$_6$-DMSO) δ: 7.48-7.65 (3H, m), 7.36 (2H, d, J=7.8 Hz), 6.48 (1H, d, J=15.7 Hz), 5.20 (1H, m), 3.45-3.65 (6H, m), 3.30-3.35 (2H, m), 2.87 (2H, d, J=11.5 Hz), 2.50 (1H, m), 1.30-2.15 (12H, m), 1.16 (9H, s).

Example 82

Cyclopentyl (2S)-{[(1-{4-[(1E)-3-(hydroxyamino)-3-oxoprop-1-en-1-yl]benzyl}piperidin-4-yl)methyl]amino}(phenyl)acetate

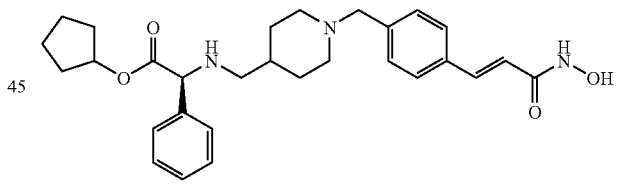

The title compound was prepared by the following methodology:

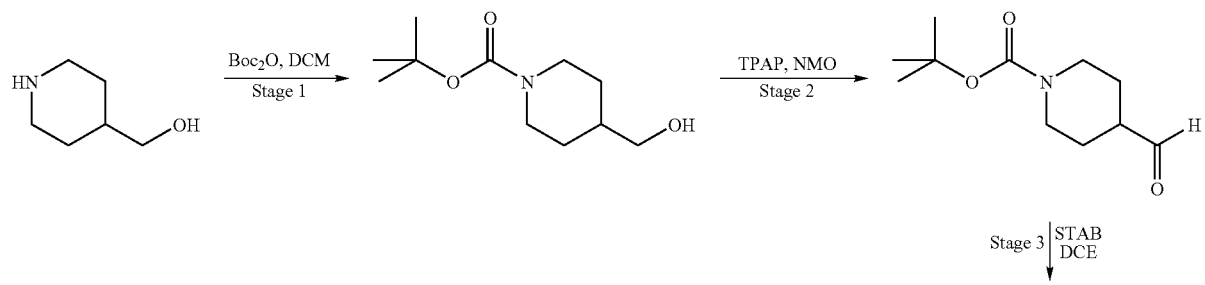

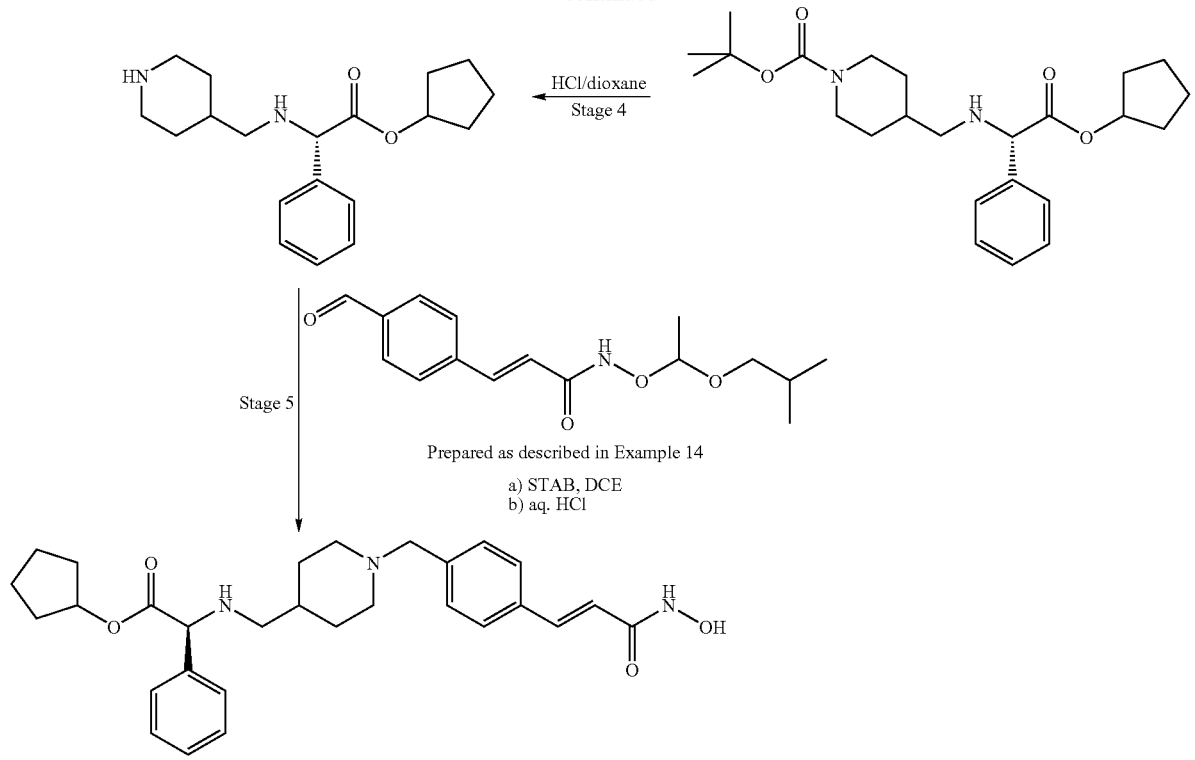

Example 82

Stage 1—Preparation of tert-butyl 4-(hydroxymethyl)piperidine-1-carboxylate

To a solution of piperidin-4-ylmethanol (5.122 g, 44.5 mmol) in DCM (70 mL) was added di-tert-butyl dicarbonate (8.91 g, 40.8 mmol). The solution was stirred at RT for 3 h and then poured into Et$_2$O (250 mL). The solution was then washed with 0.5M HCl$_{aq}$ (3×75 mL), brine (50 mL) and then dried (MgSO$_4$) and concentrated in vacuo to give the desired product (9.78 g, quant.). $^1$H NMR (300 MHz, CDCl$_3$) δ: 4.14 (2H, d, J=13.2 Hz), 3.52 (2H, d, J=6.1 Hz), 2.72 (2H, dt, J=2.2, 14.6 Hz), 1.65-1.77 (2H, m), 1.47 (9H, s), 1.13-1.26 (3H, m).

Stage 2—Preparation of tert-butyl 4-formylpiperidine-1-carboxylate

To stage 1 product (9.78 g, 44.5 mmol) in DCM (250 mL) was added N-methylmorpholine-N-oxide (6.60 g, 55.3 mmol) and TPAP (260 mg, 0.74 mmol). The mixture was stirred for 24 h, then further NMO (3.37 g, 28.3 mmol) and TPAP (30 mg, 0.08 mmol) were added. The mixture was stirred for a further 48 h, and then further NMO (2.60 g, 21.8 mmol) was added. After stirring for a further 5 h, the mixture was poured into Et$_2$O (500 mL) and washed with 0.5M HCl$_{aq}$ (4×100 mL) and brine (100 mL). The organic fraction was then dried (MgSO$_4$) concentrated and purified by column chromatography to yield the desired product (3.14 g, 35%). $^1$H NMR (300 MHz, CDCl$_3$) δ: 9.68 (1H, s), 3.97 (2H, d, J=17.1 Hz), 2.95 (2H, dt, J=3.1, 11.0 Hz), 2.41-2.46 (2H, m), 1.85-1.90 (2H, m), 1.53-1.59 (1H, m), 1.47 (9H, s).

Stage 3—Preparation of tert-butyl 4-({[(1S)-2-(cyclopentyloxy)-2-oxo-1-phenylethyl]amino}methyl)piperidine-1-carboxylate To a solution of stage 2 product (0.748 g, 3.5 mmol) in DCE (20 mL) was added Intermediate L1 (1.63 g, 4.2 mmol) and STAB (1.76 g, 8.3 mmol). The mixture was stirred for 4 h and was then quenched by addition of sat. NaHCO$_3$ solution (50 mL). The product was then extracted with DCM (2×50 mL), the combined extracts were dried (MgSO$_4$) concentrated in vacuo and purified by column chromatography (1% MeOH in DCM) to yield the desired product. m/z=417.25 [M+H]$^+$, $^1$H NMR (300 MHz, CDCl$_3$) δ: 7.28-7.39 (5H, m), 5.20 (1H, m), 4.08 (2H, d, J=9.6 Hz), 2.70 (2H, t, J=12.5 Hz), 2.50 (1H, dd, J=6.6, 11.3 Hz), 2.38 (1H, dd, J=6.8, 11.5 Hz), 1.47-1.88 (14H, m), 1.47 (9H, s).

Stage 4—Preparation of cyclopentyl (2S)-phenyl[(piperidin-4-ylmethyl)amino]acetate di-hydrochloride To stage 3 product was added 4M HCl in dioxane (5 mL). The mixture was stirred for 3 h and then concentrated under vacuum to yield the desired product (891 mg, 80% over 2 steps). $^1$H NMR (300 MHz, d$_6$-DMSO) δ: 7.24-7.40 (5H, m), 5.06 (1H, m), 4.28 (1H, s), 3.14 (2H, d, J=11.7 Hz), 2.70 (2H, t, J=12.5 Hz), 2.20-2.40 (2H, m), 1.08-1.86 (14H, m).

Stage 5—Preparation of cyclopentyl (2S)-{[(1-{4-[(1E)-3-(hydroxyamino)-3-oxoprop-1-en-1-yl]benzyl}piperidin-4-yl)methyl]amino}(phenyl)acetate (Example 82)

To a solution of stage 4 product (236 mg, 0.74 mmol) in DCE (5 mL) was added (2E)-3-(4-formylphenyl)-N-(1- isobutoxyethoxy)acrylamide (prepared as described in Example 14-218 mg, 0.75 mmol) and STAB (157 mg, 0.74 mmol). The mixture was stirred for 3 h then quenched with 0.5M HCl$_{aq}$ (20 mL) for 30 minutes. The solution was neutralized with sat. NaHCO$_3$ solution, and then extracted with DCM (3×100 mL). The combined extracts were dried (MgSO$_4$) concentrated in vacuo and purified by preparative HPLC to yield the desired product (18 mg, 5%). LCMS purity >95%, m/z=492.25 [M+H]$^+$, $^1$H NMR (300 MHz, CD$_3$OD) δ: 7.45-7.65 (3H, m), 7.25-7.45 (7H, m), 6.47 (1H, d, J=13.8 Hz), 5.15 (1H, m), 4.30 (1H, s), 3.45-3.57 (2H, m), 2.89 (2H, d, J=9.5 Hz), 2.30-2.50 (2H, m), 1.13-2.11 (15H, m).

Example 83

Cyclopentyl (2S)-cyclohexyl{[(1-{4-[(1E)-3-(hydroxyamino)-3-oxoprop-1-en-1-yl]benzyl}piperidin-4-yl)methyl]amino}acetate

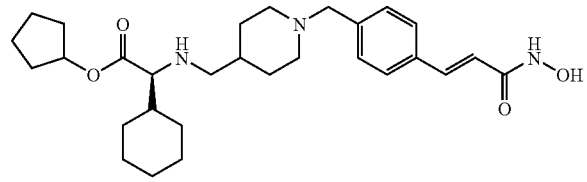 [SMILES: O=C(/C=C/c1ccc(CN2CCC(CN[C@H](C(=O)OC3CCCC3)C3CCCCC3)CC2)cc1)NO]

The title compound was prepared from Intermediate J1 by the same methodology used to make Example 82.

LCMS purity >98%, m/z=498.25 [M+H]$^+$, $^1$H NMR (300 MHz, d$_6$-DMSO) δ: 7.48 (2H, d, J=7.9 Hz), 7.33 (1H, d, J=10.8 Hz), 7.30 (2H, d, J=8.0 Hz), 6.42 (1H, d, J=13.5 Hz), 5.10 (1H, m), 4.07 (2H, q, J=5.1 Hz), 3.43 (2H, br s), 3.17 (6H, m), 2.70-2.85 (3H, m), 2.10-2.42 (2H, m), 0.96-1.94 (18H, m).

Example 84

Cyclopentyl (2S)-cyclohexyl[(1-{4-[(1E)-3-(hydroxyamino)-3-oxoprop-1-en-1-yl]phenyl}ethyl)amino]acetate

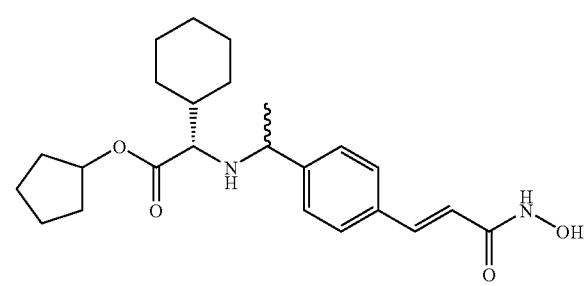 [SMILES: CC(N[C@H](C(=O)OC1CCCC1)C1CCCCC1)c1ccc(/C=C/C(=O)NO)cc1]

The title compound was prepared by the following methodology:

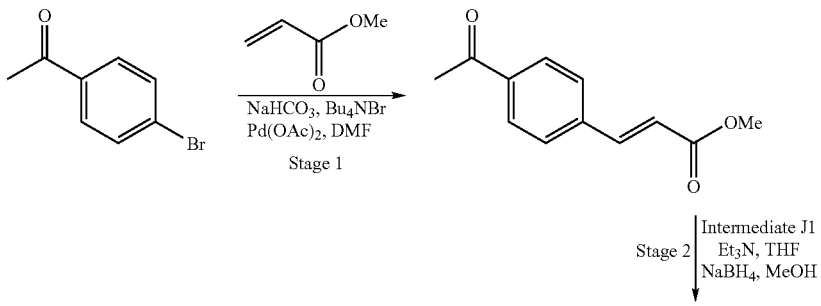

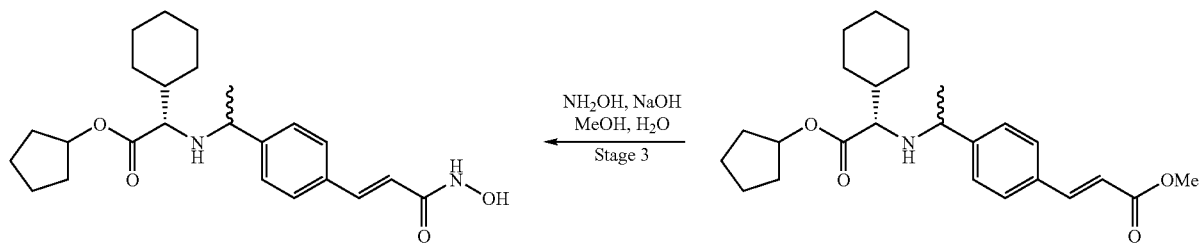

Example 84

Stage 1—Preparation of methyl (2E)-3-(4-acetylphenyl)acrylate

To 4-bromoacetophenone (1 g, 5 mmol) in anhydrous DMF (30 mL) were added methyl acrylate (450 μL, 5 mmol), sodium bicarbonate (420 mg, 5 mmol) tetrabutylammonium bromide (1.61 g, 5 mmol) and palladium acetate (56 mg, 0.25 mmol) and the reaction mixture was heated at 130° C. for 2 h. The DMF was removed by concentration under reduced pressure, the crude was dissolved in EtOAc (100 mL) and washed with water (100 mL) then brine (100 mL). The organic layer was dried (MgSO$_4$), filtered and concentrated under vacuum to afford the crude product. This was purified by flash chromatography (1:1 heptane/EtOAc) to yield the desired product (784 mg, 77%). m/z=205 [M+H]$^+$; $^1$H NMR (300 MHz, CDCl$_3$) δ: 7.99 (2H, d, J=8.3 Hz), 7.73 (1H, d, J=16.2 Hz), 7.63 (2H, d, J=8.3 Hz), 6.55 (1H, d, J=16.0 Hz), 3.85 (3H, s), 2.64 (3H, s).

Stage 2—Preparation of methyl (2E)-3-[4-(1-{[(1S)-1-cyclohexyl-2-(cyclopentyloxy)-2-oxoethyl]amino}ethyl)phenyl]acrylate To stage 1 product (500 mg, 2.45 mmol) in anhydrous THF (10 mL) were added Intermediate J1 (946 mg, 2.45 mmol), Et$_3$N (341 μL, 2.45 mmol), AcOH (4 drops) and 4 Å molecular sieves and the reaction mixture was heated at 50° C. N$_2$ atmosphere for 18 h. The reaction was cooled to RT and anhyrdous MeOH (5 mL) was added, followed by NaBH$_4$ (93 mg, 2.45 mmol). The reaction was left stirring at RT until completion, after which the solvents were removed in vacuo. The crude was poured into EtOAc (25 mL), washed with water (25 mL), 1M HCl (25 mL) then brine (25 mL). The organic layer was dried (MgSO$_4$), filtered and concentrated under vacuum to afford the desired product (1 g, 97%) m/z=414 [M+H]$^+$.

Stage 3—Preparation of cyclopentyl (2S)-cyclohexyl[(1-{4-[(1E)-3-(hydroxyamino)-3-oxoprop-1-en-1-yl]phenyl}ethyl)amino]acetate (Example 84)

To stage 2 product (60 mg, 0.14 mmol) in MeOH (1 mL) were added hydroxylamine in water (100 μL) and NaOH (60 mg) and the reaction mixture was left stirring at RT for 2 h. The reaction was quenched by addition of a sat NH$_4$Cl (2 mL), and the product was purified by preparative HPLC after concentration of solvents and filtration of the undesired salts (21 mg, 36%). LCMS purity >99%, m/z=415 [M+H]$^+$, $^1$H NMR (300 MHz, CD$_3$OD) δ: 7.67 (2H, dd, J=11.4, 8.6 Hz), 7.55 (2H, t, J=8.3 Hz), 7.48 (2H, d, J=8.1 Hz), 6.61-6.46 (1H, m), 5.30 (1H, t, J=5.9 Hz), 4.58-4.45 (1H, m), 3.41-3.38 (1H, m), 1.99-1.78 (6H, m), 1.75 (3H, d, J=6.8 Hz), 1.72-1.44 (4H, m), 1.38-0.92 (8H, m).

The following examples were prepared using the same methodology:

| Example | Chemical name | Intermediates used | Analytical data |
|---|---|---|---|
| 85 | tert-Butyl N-(1-{4-[(1E)-3-(hydroxyamino)-3-oxoprop-1-en-1-yl]phenyl}ethyl)-L-leucinate | A, K2 | LCMS purity 93%, m/z = 377 [M + H]$^+$, $^1$H NMR (300 MHz, CD$_3$OD) δ: 7.74-7.69 (2H, m), 7.68-7.56 (1H, m), 7.49 (2H, d, J = 8.3 Hz), 6.58 (1H, d, J = 16.0 Hz), 4.51 (1H, q, J = 6.7 Hz), 1.73 (3H, d, J = 6.8 Hz), 1.69-1.61 (1H, m), 1.55 (9H, s), 1.06-0.98 (2H, m), 0.95-0.91 (1H, m), 0.88 (3H, d, J = 2.8 Hz), 0.86 (3H, d, J = 2.6 Hz). |
| 86 | tert-Butyl N-(1-{4-[3-(hydroxyamino)-3-oxopropyl]phenyl}ethyl)-L-leucinate | B, K2 | LCMS purity 100%, m/z = 379 [M + H]$^+$, $^1$H NMR (300 MHz, CD$_3$OD) δ: 7.41-7.33 (4H, m), 4.43 (1H, t, J = 7.0 Hz), 2.99 (2H, t, J = 7.5 Hz), 2.42 (2H, t, J = 7.5 Hz), 1.82-1.75 (2H, m), 1.71 (3H, d, J = 7.0 Hz), 1.64-1.56 (2H, m), 1.55 (9H, s), 0.86 (6H, d, J = 6.2 Hz). |

Example 87 tert-Butyl N-(2-{4-[(1E)-3-(hydroxyamino)-3-oxoprop-1-en-1-yl]phenyl}ethyl)-L-leucinate

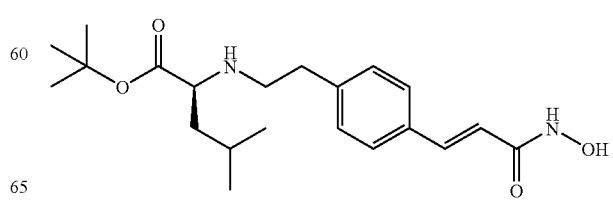

The title compound was prepared by the following methodology:

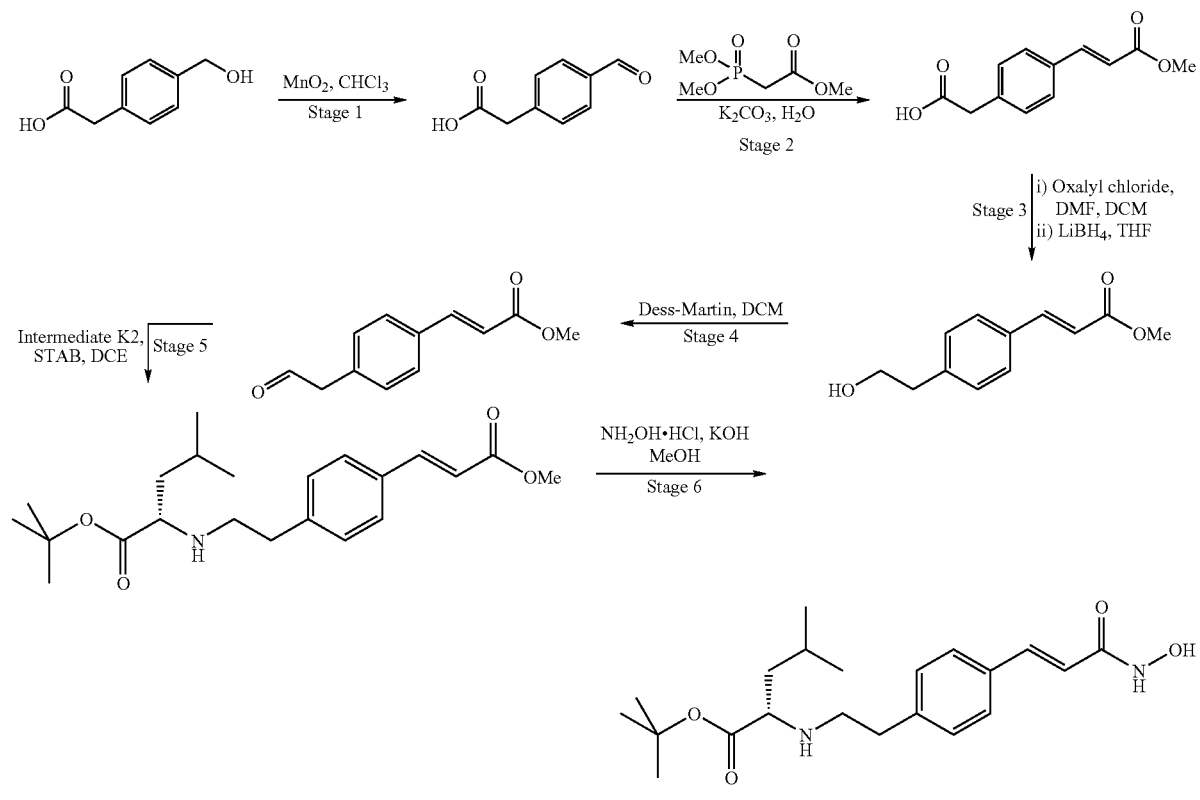

Example 87

Stage 1—Preparation of (4-formylphenyl)acetic acid

To [4-(hydroxymethyl)phenyl]acetic acid (3 g, 18 mmol) in CHCl$_3$ (50 mL) under N$_2$ was added manganese dioxide (7.7 g, 90 mmol) and the reaction mixture was stirred at 50° C. for 18 h. The crude was filtered through a pad of celite, washed with DCM (50 mL) and concentrated under reduced pressure to give the desired product (1.76 g, 59%). $^1$H NMR (300 MHz, d$_6$-DMSO) δ: 12.49 (1H, br s), 9.99 (1H, s), 7.89-7.84 (2H, m), 7.50 (2H, d, J=7.9 Hz), 3.72 (2H, s).

Stage 2—Preparation of {4-[(1E)-3-methoxy-3-oxoprop-1-en-1-yl]phenyl}acetic acid To stage 1 product (1.03 g, 6.3 mmol) in water (100 mL) were added K$_2$CO$_3$ (2.61 g, 18.9 mmol) then trimethylphosphonoacetate (1.23 mL, 7.6 mmol) at 0° C. Addition was carried out over 10 minutes to avoid the reaction temperature rising above 15° C. The reaction mixture was then stirred at RT for 72 h. A solution of 1M HCl was added until pH~1. The white precipitate was isolated by filtration, washed with water (100 mL), concentrated and dried on the freeze drier to afford the desired product as a white solid (784 mg, 57%). $^1$H NMR (300 MHz, d$_6$-DMSO) δ: 12.46 (1H, br s), 7.69-7.63 (2H, m), 7.31 (2H, d, J=8.1 Hz), 6.74 (1H, d, J=16.0 Hz), 6.63 (1H, d, J=16.0 Hz), 3.72 (3H, s), 3.62 (2H, s).

Stage 3—Preparation of methyl (2E)-3-[4-(2-hydroxyethyl)phenyl]acrylate

To stage 2 product (784 mg) in DCM (20 mL) under N$_2$ atmosphere, were added oxalyl chloride (2 mL) and DMF (3 drops). The reaction was left stirring for 1 h at RT. The crude was concentrated under reduced pressure. Anhydrous THF (10 mL) was then added, followed by a solution of lithium borohydride in THF (3 mL, 2M in THF) at 0° C. This was left stirring for 1 h, then quenched with sat NH$_4$Cl (15 mL) and extracted with EtOAc (50 mL). The organic layer was washed with brine (50 mL), dried (MgSO$_4$), filtered and concentrated under reduced pressure. The crude was purified on a Biotage automated purification system to afford the pure product (250 mg, 34%). $^1$H NMR (300 MHz, CDCl$_3$) δ: 7.70 (1H, d, J=16.0 Hz), 7.50 (2H, d, J=8.3 Hz), 7.28 (2H, d, J=8.1 Hz), 6.44 (1H, d, J=16.0 Hz), 3.90 (2H, t, J=6.5 Hz), 3.82 (3H, s), 2.91 (2H, t).

Stage 4—Preparation of methyl (2E)-3-[4-(2-oxoethyl)phenyl]acrylate

To stage 3 product (200 mg, 0.97 mmol) in DCM (10 mL) at 0° C. was added Dess-Martin periodinane (492 mg, 1.16 mmol) and the reaction mixture was stirred at RT for 2 h. The reaction was quenched by addition of a 1/1 mixture of sat NaHCO$_3$ and sodium dithionite solutions (5 mL) and left stirring vigorously for 30 minutes. The mixture was extracted with DCM (2×10 mL) and washed with brine (10 mL). The organic was dried (MgSO$_4$), and concentrated under reduced pressure to afford the desired product (198 mg, quant.). m/z=205 [M+H]$^+$.

Stage 5—Preparation of tert-butyl N-(2-{4-[(1E)-3-methoxy-3-oxoprop-1-en-1-yl]phenyl}ethyl)-L-leucinate To stage 4 product (88 mg, 0.43 mmol) in DCE (3 mL) was added Intermediate K$_2$ (81 mg, 0.43 mmol) followed by sodium triacetoxyborohydride (109 mg, 0.51 mmol) and the reaction mixture was stirred at RT under N$_2$ atmosphere for 72 h. DCM (10 mL) and water (10 mL) were added. The organic layer was separated, washed with sat NaHCO$_3$ (15 mL) and brine (15 mL), dried (MgSO$_4$), filtered and concentrated under reduced pressure to afford the desired product (162 mg, quant.). This was used directly in the final step without further purification. m/z=376 [M+H]$^+$.

Stage 6—Preparation of tert-butyl N-(2-{4-[(1E)-3-(hydroxyamino)-3-oxoprop-1-en-1-yl]phenyl}ethyl)-L-leucinate (Example 87)

To a solution of crude stage 5 product (162 mg, 0.43 mmol) in MeOH (2 mL) was added hydroxylamine hydrochloride (120 mg, 1.72 mmol) and the reaction mixture was cooled to −5° C. A solution of KOH (193 mg, 3.44 mmol) in water (0.5 mL) was prepared, cooled and added slowly to the reaction mixture. After 30 minutes stirring at −5° C., the reaction was complete. A solution of 1M HCl was added to neutralise the pH. The crude was purified by preparative HPLC to yield the desired product (16 mg, 9%). LCMS purity 96%, m/z=377 [M+H]$^+$.

Example 88

(2S)-Cyclohexyl({4-[(1E)-3-(hydroxyamino)-3-oxo-prop-1-en-1-yl]benzyl}amino)acetic acid

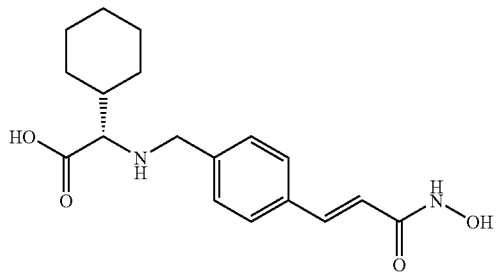 [SMILES: O=C(/C=C/c1ccc(CN[C@H](C(=O)O)C2CCCCC2)cc1)NO]

The title compound was prepared by the following methodology:

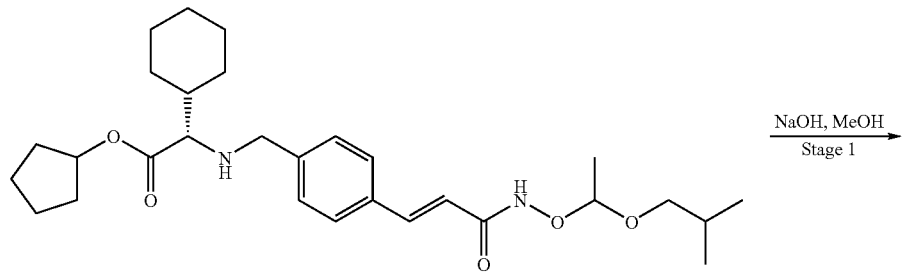

Intermediate in the preparation of Example 14

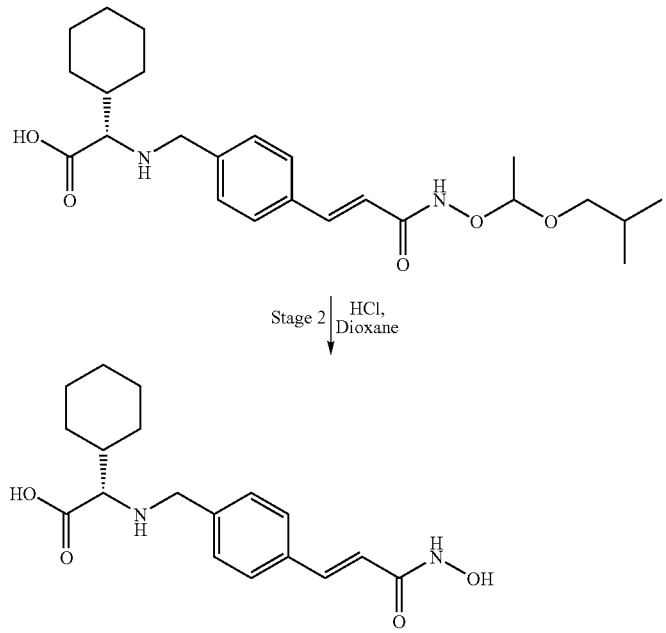

Example 88

Stage 1—Preparation of (2S)-cyclohexyl[(4-{(1E)-3-[(1-isobutoxyethoxy)amino]-3-oxoprop-1-en-1-yl}benzyl)amino]acetic acid 1N NaOH$_{aq}$ (3 mL) was charged to a solution of cyclopentyl (2S)-cyclohexyl[(4-{(1E)-3-[(1-isobutoxyethoxy)amino]-3-oxoprop-1-en-1-yl}benzyl)amino]acetate (prepared as described in Example 14-0.3 g, 0.6 mmol) in MeOH (5 mL) and stirred at 45° C. for 4 days. The MeOH was removed in vacuo and the residue washed with EtOAc (10 mL). The aqueous phase was acidified to pH~2 with saturated citric acid solution, extracted with EtOAc (2×10 mL) and the organic phase dried (MgSO$_4$) and concentrated in vacuo to afford the product as a yellow oil (0.14 g, 53%). m/z=433 [M+H]$^+$.

Stage 2—Preparation of (2S)-Cyclohexyl({4-[(1E)-3-(hydroxyamino)-3-oxoprop-1-en-1-yl]benzyl}amino)acetic acid (Example 88)

4N HCl in dioxane (0.18 mL, 0.72 mmol) was added to a solution of stage 1 product (0.14 g, 0.32 mmol) in DCM and the reaction stirred for 5 minutes. The reaction was then concentrated to dryness in vacuo to afford a yellow solid. Purification by preparative HPLC afforded the desired product as an off-white solid (4 mg, 2%). $^1$H NMR (300 MHz, d$_6$-DMSO) δ: 10.80 (1H, s), 9.08 (1H, m), 7.73 (2H, d, J=7.8 Hz), 7.52-7.45 (3H, m), 6.50 (1H, d, J=16.2 Hz), 4.16 (2H, m), 3.70 (1H, m), 1.91 (1H, m), 1.81-1.50 (5H, m), 1.32-0.86 (5H, m).

The following examples were prepared using the same methodology:

| Example | Chemical name | Intermediate from Example number | Analytical data |
|---|---|---|---|
| 89 | N-{4-[(1E)-3-(Hydroxyamino)-3-oxoprop-1-en-1-yl]benzyl}-L-leucine | 15 | LCMS purity 97%, m/z = 307 [M + H]$^+$, $^1$H NMR (300 MHz, CD$_3$OD) δ: 7.79-7.44 (5H, m), 6.55 (1H, d, J = 15.9 Hz), 4.28 (2H, s), 4.00 (1H, m), 1.96-1.65 (3H, m), 1.00 (6H, m). |
| 90 | O-tert-Butyl-N-{4-[(1E)-3-(hydroxyamino)-3-oxoprop-1-en-1-yl]benzyl}-L-serine | 16 | LCMS purity 100%, m/z = 337 [M + H]$^+$, $^1$H NMR (300 MHz, CD$_3$OD) δ: 7.77-7.50 (5H, m), 6.55 (1H, d, J = 15.9 Hz), 4.32 (1H, s), 3.88 (2H, s), 1.31 (2H, s), 1.25 (9H, s). |
| 91 | (2S)-({4-[(1E)-3-(Hydroxyamino)-3-oxoprop-1-en-1-yl]benzyl}amino)(phenyl)acetic acid | 17 | LCMS purity >95%, m/z = 327 [M + H]$^+$, $^1$H NMR (300 MHz, CD$_3$OD) δ: 7.75-7.41 (10H, m), 6.55 (1H, d, J = 15.6 Hz), 5.10 (1H, s), 4.21 (2H, q). |
| 92 | N-{4-[(1E)-3-(Hydroxyamino)-3-oxoprop-1-en-1-yl]benzyl}-D-leucine | 18 | LCMS purity 100%, m/z = 307 [M + H]$^+$, $^1$H NMR (300 MHz, CD$_3$OD) δ: 7.76-7.48 (5H, m), 6.54 (1H, d, J = 15.9 Hz), 4.16 (2H, m), 3.62 (1H, m), 1.91-0.74 (9H, m). |
| 93 | (2R)-Cyclohexyl({4-[(1E)-3-(hydroxyamino)-3-oxoprop-1-en-1-yl]benzyl}amino)acetic acid | 19 | LCMS purity 100%, m/z = 333 [M + H]$^+$, $^1$H NMR (300 MHz, CD$_3$OD) δ: 7.78-7.43 (5H, m), 6.54 (1H, d, J = 15.9 Hz), 4.24 (2H, m), 3.57 (1H, m), 2.03-1.01 (11H, m). |
| 94 | O-tert-Butyl-N-{4-[(1E)-3-(hydroxyamino)-3-oxoprop-1-en-1-yl]benzyl}-D-serine | 20 | LCMS purity 100%, m/z = 337 [M + H]$^+$, $^1$H NMR (300 MHz, CD$_3$OD) δ: 7.72-7.51 (5H, m), 6.55 (1H, d, J = 15.6 Hz), 4.33 (2H, s), 4.12 (1H, m), 3.93 (2H, m), 1.25 (9H, s). |
| 95 | (2R)-({4-[(1E)-3-(Hydroxyamino)-3-oxoprop-1-en-1-yl]benzyl}amino)(phenyl)acetic acid | 22 | LCMS purity 100%, m/z = 327 [M + H]$^+$, $^1$H NMR (300 MHz, CD$_3$OD) δ: 7.75-7.34 (10H, m), 6.54 (1H, d, J = 15.9 Hz), 4.53 (1H, s), 4.18 (2H, q). |
| 96 | (2S)-Cyclohexyl({4-[3-(hydroxyamino)-3-oxopropyl]benzyl}amino)acetic acid | 33 | LCMS purity 100%, m/z = 335 [M + H]$^+$, $^1$H NMR (300 MHz, CD$_3$OD) δ: 7.45-7.22 (4H, m), 4.12 (2H, q), 2.95 (2H, t), 2.39 (2H, t), 1.91-1.04 (11H, m). |
| 97 | N-{4-[3-(Hydroxyamino)-3-oxopropyl]benzyl}-L-leucine | 34 | LCMS purity 100%, m/z = 309 [M + H]$^+$, $^1$H NMR (300 MHz, CD$_3$OD) δ: 7.50-7.15 (4H, m), 4.57 (1H, s), 4.12 (2H, q), 2.94 (2H, t), 2.39 (2H, t), 1.80 (2H, m), 1.59 (1H, m), 0.93 (6H, dd). |
| 98 | (2S)-({4-[3-(Hydroxyamino)-3-oxopropyl]benzyl}amino)(phenyl)acetic acid | 39 | LCMS purity 90%, m/z = 329 [M + H]$^+$, $^1$H NMR (300 MHz, d$_6$-DMSO) δ: 10.38 (1H, s), 9.83 (1H, br s), 8.72 (1H, br s), 7.6-7.4 (5H, m), 7.29 (4H, dd), 5.09 (1H, s), 4.00 (2H, dd), 2.84 (2H, t), 2.27 (2H, t).□ |
| 99 | N-{4-[3-(Hydroxyamino)-3-oxopropyl]benzyl}-L-valine | 42 | LCMS purity 90%, m/z = 295 [M + H]$^+$, $^1$H NMR (300 MHz, CD$_3$OD) δ: 7.46-7.39 (2H, m), 7.38-7.30 (2H, m), 4.23 (2H, d, J = 9.6 Hz), 3.81 (1H, d, J = 3.6 Hz), 2.97 (2H, t, J = 7.4 Hz), 2.41 (2H, t, J = 7.5 Hz), 2.36-2.27 (1H, m), 1.18-1.10 (3H, m), 1.08-1.00 (3H, m). |

-continued

| Example | Chemical name | Intermediate from Example number | Analytical data |
|---|---|---|---|
| 100 | N-{4-[3-(Hydroxyamino)-3-oxopropyl]benzyl}-3-methyl-L-valine | 43 | LCMS purity 90%, m/z = 309 [M + H]+, 1H NMR (300 MHz, CD3OD) δ: 7.49-7.28 (4H, m), 4.32 (1H, d, J = 13.6 Hz), 4.13 (1H, d, J = 13.6 Hz), 3.40 (1H, s), 2.98 (2H, t, J = 7.5 Hz), 2.41 (2H, t, J = 7.5 Hz), 1.08 (9H, s). |
| 101 | (2S)-Cyclohexyl[({6-[(1E)-3-(hydroxyamino)-3-oxoprop-1-en-1-yl]pyridin-3-yl}methyl)amino]acetic acid | 53 | LCMS purity 100%, m/z = 334 [M + H]+, 1H NMR (300 MHz, CD3OD) δ: 8.65 (1H, s), 7.93 (1H, m), 7.60 (2H, m), 6.92 (1H, d, J = 15.6 Hz), 4.02 (2H, q), 1.90-1.09 (11H, m). |
| 102 | N-({6-[(1E)-3-(Hydroxyamino)-3-oxoprop-1-en-1-yl]pyridin-3-yl}methyl)-L-leucine | 54 | LCMS purity >95%, m/z = 308 [M + H]+, 1H NMR (300 MHz, CD3OD) δ: 8.65 (1H, s), 7.93 (1H, dd), 7.59 (2H, dd), 6.91 (1H, d, J = 15.6 Hz), 4.54 (1H, s), 4.02 (2H, q), 1.97-1.19 (3H, m), 0.95 (6H, dd). |
| 103 | (2S)-Cyclohexyl[({6-[3-(hydroxyamino)-3-oxopropyl]pyridin-3-yl}methyl)amino]acetic acid | 62 | LCMS purity 95%, m/z = 336 [M + H]+, 1H NMR (300 MHz, CD3OD) δ: 8.72 (1H, d, J = 2.1 Hz), 8.19 (1H, dd, J = 8.2, 2.2 Hz), 7.70 (1H, d, J = 8.1 Hz), 4.37 (2H, s), 3.94 (1H, d), 3.22 (2H, t, J = 7.2 Hz), 2.85 (2H, t, J = 7.2 Hz), 2.07-1.96 (1H, m), 1.88-1.80 (4H, m), 1.75-1.69 (1H, m), 1.47-1.17 (5H, m). |
| 104 | (2S)-Cyclohexyl[({5-[3-(hydroxyamino)-3-oxopropyl]pyridin-2-yl}methyl)amino]acetic acid | 70 | LCMS purity 98%, m/z = 336 [M + H]+, 1H NMR (300 MHz, d6-DMSO) δ: 10.39 (1H, br s), 8.49 (1H, s), 7.72 (1H, dd, J = 2.2, 8.0 Hz), 7.44 (1H, d, J = 8.0 Hz), 4.30 (2H, s), 3.82 (1H, d, J = 3.3 Hz), 2.87 (2H, t, J = 7.3 Hz), 2.31 (2H, t, J = 7.3 Hz), 1.57-2.04 (6H, m), 0.92-1.38 (5H, m). |
| 105 | (2S)-Cyclohexyl[({4-[({3-[(1E)-3-(hydroxyamino)-3-oxoprop-1-en-1-yl]benzyl}amino)methyl]cyclohexyl}methyl)amino]acetic acid | 79 | LCMS purity 97%, m/z = 458 [M + H]+, 1H NMR (300 MHz, CD3OD) δ: 7.78-7.47 (5H, m), 6.57 (1H, m), 4.26 (2H, s), 3.59 (1H, s), 3.04-2.75 (4H, m), 2.06-0.78 (19H, m). |
| 106 | (2S)-Cyclohexyl[(1-{4-[(1E)-3-(hydroxyamino)-3-oxoprop-1-en-1-yl]benzyl}piperidin-4-yl)amino]acetic acid | 80 | LCMS purity 98%, m/z = 416 [M + H]+, 1H NMR (300 MHz, CD3OD) δ: 7.67 (2H, d, J = 7.5 Hz), 7.60 (1H, obs d), 7.57 (2H, d, J = 7.0 Hz), 6.56 (1H, d, J = 15.6 Hz), 4.35 (2H, s), 3.94 (1H, d, J = 3.1 Hz), 3.40-3.65 (3H, m), 3.12 (2H, br m), 2.39 (2H, t, J = 15.4 Hz), 1.90-2.22 (3H, m), 1.60-1.80 (5H, m), 1.05-1.50 (5H, m). |
| 107 | (2S)-{[(1-{4-[(1E)-3-(Hydroxyamino)-3-oxoprop-1-en-1-yl]benzyl}piperidin-4-yl)methyl]amino}(phenyl)acetic acid | 82 | LCMS purity 98%, m/z = 424 [M + H]+, 1H NMR (300 MHz, CD3OD) δ: 7.68 (2H, d, J = 7.8 Hz), 7.46-7.64 (8H, m), 6.58 (1H, d, J = 16.0 Hz), 5.02 (1H, s), 4.35 (2H, s), 3.44-3.55 (2H, m), 2.80-3.15 (3H, m), 2.00-2.25 (3H, m), 1.47-1.65 (2H, m). |
| 108 | (2S)-Cyclohexyl[(1-{4-[(1E)-3-(hydroxyamino)-3-oxoprop-1-en-1-yl]phenyl}ethyl)amino]acetic acid | 84 | LCMS purity 92%, m/z = 347 [M + H]+, 1H NMR (300 MHz, CD3OD) δ: 7.69 (2H, d, J = 7.8 Hz), 7.61 (1H, d, J = 15.9 Hz), 7.52-7.37 (2H, m), 6.55 (1H, d, J = 15.6 Hz), 4.52-4.50 (1H, m), 3.26-3.23 (1H, m), 1.76 (3H, d, J = 6.6 Hz), 1.60-1.43 (4H, m), 1.38-0.92 (6H, m). |

Example 109

N-{4-[3-(Hydroxyamino)-3-oxopropyl]benzyl}-L-isoleucine

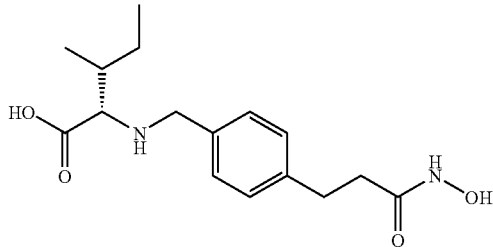 [SMILES: CCC(C)[C@H](NCc1ccc(CCC(=O)NO)cc1)C(=O)O]

The title compound was prepared by the following methodology:

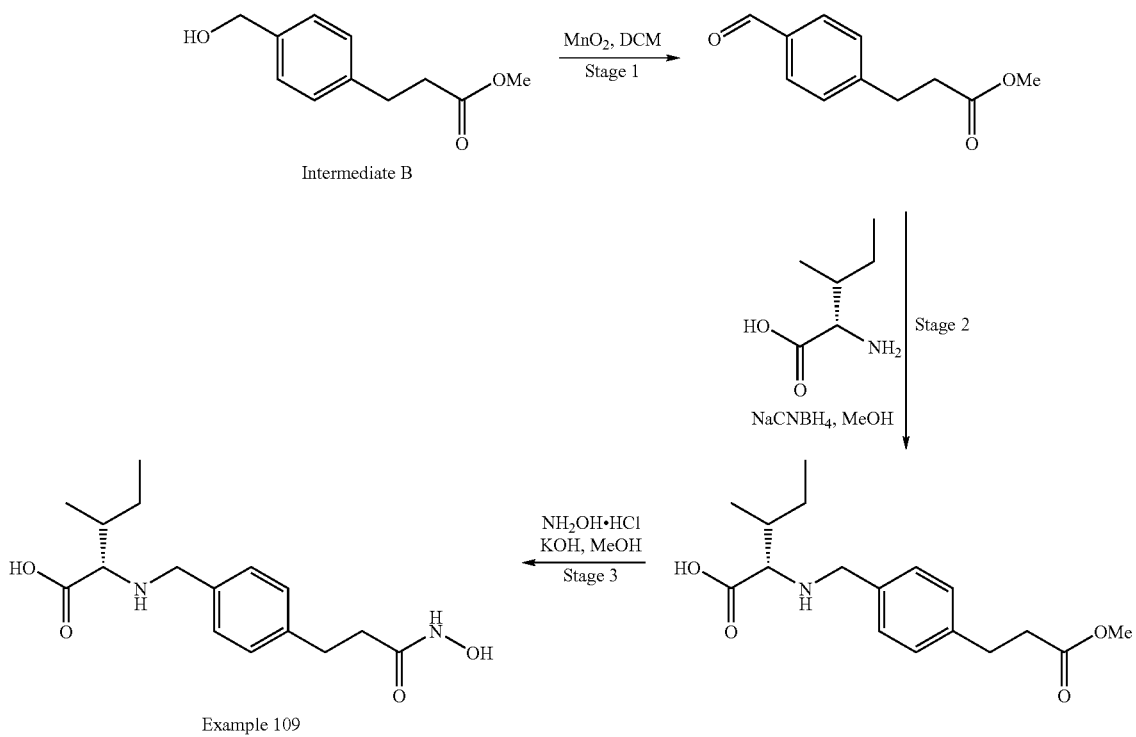

Stage 1—Preparation of methyl 3-(4-formylphenyl)propanoate

To a solution of Intermediate B (300 mg, 1.54 mmol) in DCM (25 mL) was added manganese dioxide (2.98 g, 34 mmol). The mixture was stirred for 15 minutes, and then filtered through Celite and washed with additional DCM (100 mL). The filtrate was concentrated to yield the desired product. This was used directly in the next stage without further purification or characterisation.

Stage 2—Preparation of N-{4-[(1E)-3-methoxy-3-oxopropyl]benzyl}-L-isoleucine To stage 1 product (150 mg, 0.78 mmol) in anhydrous MeOH (5 mL) were added L-isoleucine (103 mg, 0.78 mmol) and sodium cyanoborohydride (49 mg, 0.78 mmol). The resulting mixture was stirred overnight at RT. The solvent was removed by concentration and the residue partitioned between DCM (20 mL) and water (20 mL). The organic layer was washed with water (20 mL) and brine (20 mL), dried (MgSO$_4$) and concentrated under reduced pressure to afford the desired product as a colourless oil (140 mg, 58%). m/z=308 [M+H]$^+$; $^1$H NMR (300 MHz, CD$_3$OD) δ: 7.42-7.35 (1H, m), 7.28 (2H, d, J=7.7 Hz), 7.22-7.16 (1H, m), 4.57 (1H, s), 3.64 (3H, s), 3.33 (1H, dt, J=3.3, 1.6 Hz), 2.92 (2H, t, J=7.5 Hz), 2.64 (2H, t, J=3.8 Hz), 2.17 (2H, s), 1.41-1.27 (2H, m), 0.97 (3H, d, J=6.6 Hz), 0.91 (3H, t, J=7.3 Hz).

Stage 3—Preparation of N-{4-[3-(Hydroxyamino)-3-oxopropyl]benzyl}-L-isoleucine (Example 109)

To stage 2 product (110 mg, 0.36 mmol) in MeOH (1 mL) was added hydroxylamine hydrochloride at −5° C. KOH was dissolved in the minimum amount of water, cooled and added to the solution. The resulting mixture was stirred at −5° C. for 70 minutes. The pH was adjusted to 7 by addition of 1M HCl solution. The solution was then concentrated to dryness, MeOH was added and the suspension was filtered to remove excess salts. The filtrate was purified by preparative HPLC to afford the title compound as a white solid (31 mg, 28%).

LCMS purity 93%, m/z=309 [M+H]$^+$, $^1$H NMR (300 MHz, CD$_3$OD) δ: 7.46-7.32 (4H, m), 4.22 (2H, s), 3.86 (1H, d, J=3.2 Hz), 2.97 (2H, t, J=7.5 Hz), 2.41 (2H, t, J=7.5 Hz), 2.04-1.97 (1H, m), 1.52 (9H, s), 1.65-1.38 (2H, m), 1.03-0.98 (6H, m).

Example 110

N-({6-[3-(hydroxyamino)-3-oxopropyl]pyridin-3-yl}methyl)-L-leucine

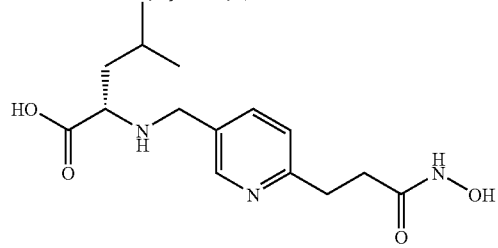 [SMILES: CC(C)C[C@H](NCc1ccc(CCC(=O)NO)nc1)C(=O)O]

The title compound was prepared by the following methodology:

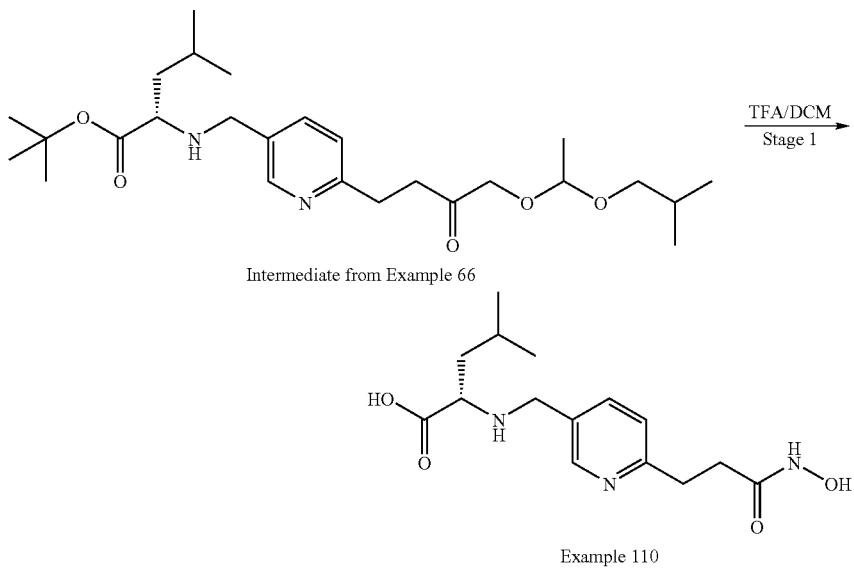

Intermediate from Example 66

Example 110

Stage 1—Preparation of N-({6-[3-(hydroxyamino)-3-oxopropyl]pyridin-3-yl}methyl)-L-leucine (Example 110)

The intermediate to Example 66 (50 mg, 0.1 mmol) was treated with 25% TFA in DCM (3 mL) and stirred at RT for 3 h. The solvents were removed in vacuo and the TFA azeotroped with toluene (3×25 mL) to afford the title compound as a white solid (30 mg, quant.). LCMS purity 80%, m/z=310 [M+H]$^+$, $^1$H NMR (300 MHz, CD$_3$OD) δ: 8.64 (1H, d, J=0.8 Hz), 7.98 (1H, dd, J=8.1, 2.4 Hz), 7.51 (1H, d, J=7.9 Hz), 4.32 (2H, s), 4.04 (1H, dd, J=8.6, 5.2 Hz), 3.17 (2H, t, J=7.3 Hz), 2.57 (2H, t, J=7.4 Hz), 1.95-1.82 (2H, m), 1.81-1.69 (1H, m), 1.04 (3H, d, J=6.2 Hz), 1.02 (3H, d, J=6.2 Hz).

The following examples were prepared using the same methodology:

| Example | Chemical name | Intermediate from Example number | Analytical data |
|---|---|---|---|
| 111 | N-({5-[3-(Hydroxyamino)-3-oxopropyl]pyridin-2-yl}methyl)-L-leucine | 71 | LCMS purity 98%, m/z = 311 [M + H]$^+$, $^1$H NMR (300 MHz, CD$_3$OD) δ: 8.53 (1H, s), 7.76 (1H, d, J = 7.9 Hz), 7.41 (1H, d, J = 7.9 Hz), 4.41 (2H, s), 4.07 (1H, t, J = 5.8 Hz), 3.00 (2H, t, J = 7.3 Hz), 2.44 (2H, t, J = 7.4 Hz), 1.74-1.99 (3H, m), 1.02 (3H, d, J = 6.0 Hz), 1.01 Hz (3H, d, J = 6.0 Hz). |
| 112 | N-(1-{4-[(1E)-3-(Hydroxyamino)-3-oxoprop-1-en-1-yl]phenyl}ethyl)-L-leucine | 85 | LCMS purity 100%, m/z = 321 [M + H]$^+$, $^1$H NMR (300 MHz, CD$_3$OD) δ: 7.71 (2H, d, J = 8.1 Hz), 7.61 (1H, d, J = 15.8 Hz), 7.53 (2H, d, J = 8.3 Hz), 6.57 (1H, d, J = 15.8 Hz), 4.55 (1H, q, J = 6.7 Hz), 3.44 (1H, d), 2.02 (1H, d, J = 8.7 Hz), 2.03-2.00 (1H, m), 1.75 (3H, d, J = 7.0 Hz), 1.71-1.60 (2H, m), 1.26 (1H, t, J = 7.2 Hz), 0.87 (3H, d, J = 6.2 Hz), 0.84 (3H, d, J = 6.2 Hz). |

Example 113
Cyclopentyl 4-{4-[3-(hydroxyamino)-3-oxopropyl]benzyl}piperazine-2-carboxylate
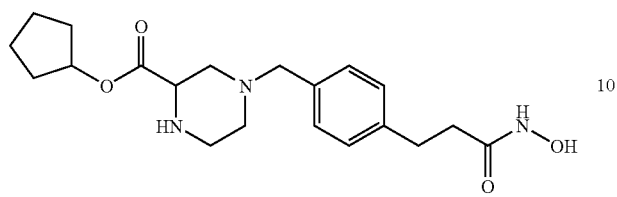
The title compound was prepared by the following methodology:
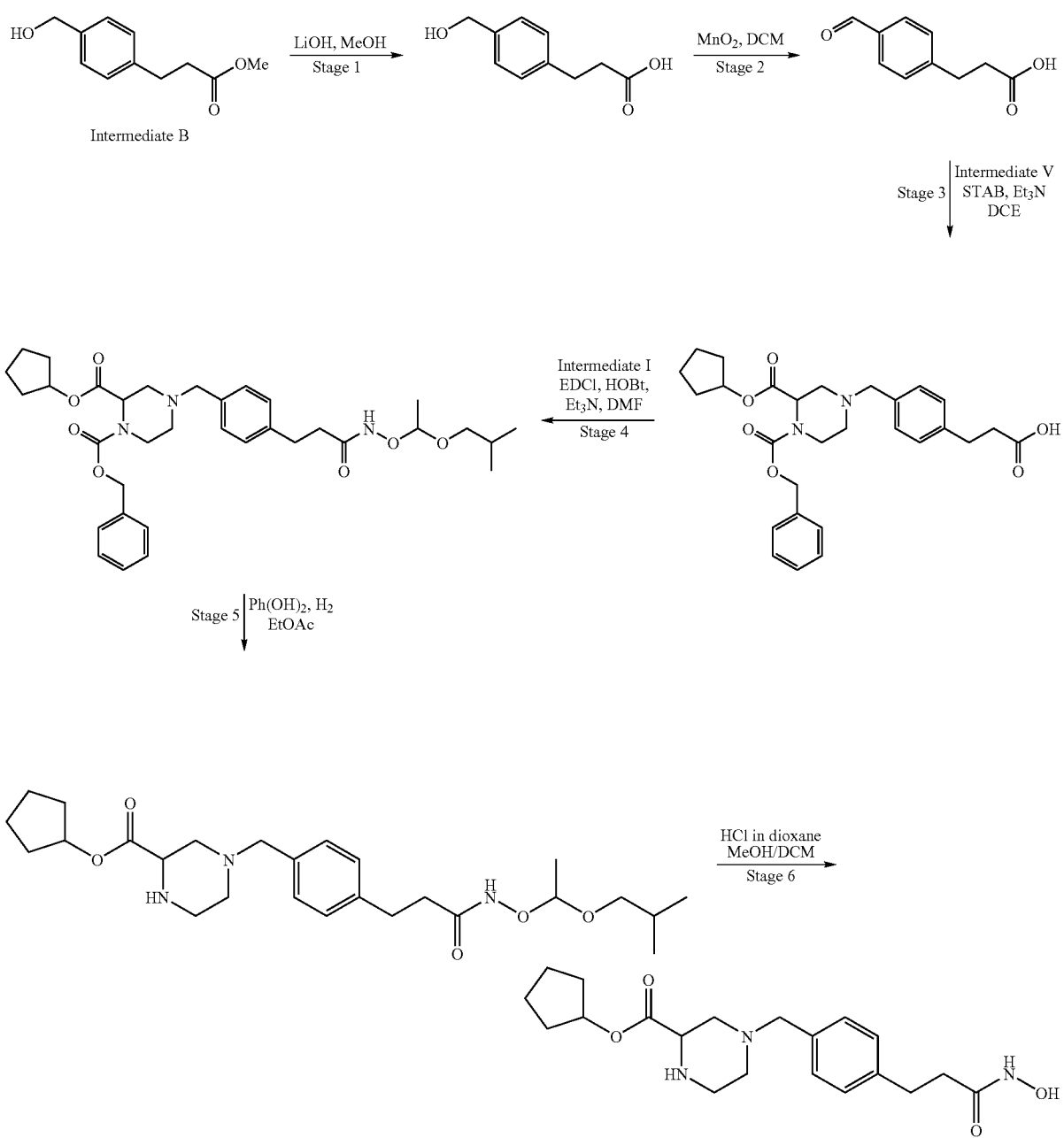

Stage 1—Preparation of 3-[4-(hydroxymethyl)phenyl]propanoic acid

Intermediate B (5 g, 25.7 mmol) was dissolved in MeOH (50 mL) and water (10 mL). LiOH (1.85 g, 77.2 mmol) was added and the reaction stirred at RT for 18 h. The reaction mixture was acidified to pH~3 with 1M HCl, the resulting precipitate was isolated by filtration to afford the desired product (4.57 g, quant.). $^1$H NMR (300 MHz, d$_6$-DMSO) δ: 7.18 (4H, q), 4.45 (2H, d), 2.81 (2H, t), 2.62 (2H, t).

Stage 2—Preparation of 3-(4-formylphenyl)propanoic acid

Stage 1 product (2 g, 11 mmol) was dissolved in anhydrous DCM (100 mL) and treated with MnO$_2$ (10 g, 115 mmol). The reaction was stirred at 35° C. for 18 h. The resulting suspension was filtered through celite and the filtrate concentrated under reduced pressure to afford the title compound as a white solid (1.64 g, 84%). $^1$H NMR (300 MHz, CDCl$_3$) δ: 10.00 (1H, s), 7.84 (2H, d, J=8.7 Hz), 7.41 (2H, d, J=8.7 Hz), 3.08 (2H, t, J=7.6 Hz), 2.25 (2H, t, J=7.6 Hz).

Stage 3—Preparation of 3-[4-({4-[(benzyloxy)carbonyl]-3-[(cyclopentyloxy)carbonyl]piperazin-1-yl}methyl)phenyl]propanoic acid Stage 2 product (137 mg, 0.77 mmol), Intermediate V (256 mg, 0.69 mmol), STAB (196 mg, 0.92 mmol) and Et$_3$N (104 µL, 0.77 mmol) were added to anhydrous DCE (4 mL) and stirred at RT for 18 h. The reaction mixture was partitioned between DCM (50 mL) and water (50 mL). The organic layer was washed with brine (50 mL), dried (MgSO$_4$) and concentrated under reduced pressure to afford the desired product (341 mg, 90%). m/z=495 [M+H]$^+$.

Stage 4—Preparation of 1-benzyl 2-cyclopentyl 4-(4-{3-[(1-isobutoxyethoxy)amino]-3-oxopropyl}benzyl)piperazine-1,2-dicarboxylate To a solution of stage 3 product (341 mg, 0.69 mmol) in DMF (5 mL) were added EDCI (159 mg, 0.83 mmol), HOBt (112 mg, 0.83 mmol), Et$_3$N (480 µL, 3.45 mmol) and Intermediate I (477 µL, 3.45 mmol). The reaction was stirred at RT for 18 h and then heated to 50° C. for a further 3 h. The reaction mixture was then diluted with DCM (50 mL) and washed with sat NaHCO$_3$ (50 mL) and brine (50 mL). The organic layer was dried (MgSO$_4$) and concentrated in vacuo. The resulting residue was purified by column chromatography (Heptane/EtOAc 6:1) to afford the title compound as a white solid (300 mg, 72%). m/z=610 [M+H]$^+$.

Stage 5—Preparation of cyclopentyl 4-(4-{3-[(1-isobutoxyethoxy)amino]-3-oxopropyl}benzyl)piperazine-2-carboxylate Stage 4 product (150 mg, 0.24 mmol) was dissolved in EtOAc (25 mL) and the solution degassed. Pd(OH)$_2$ (50 mg, 0.35 mmol) was added and the reaction stirred under H$_2$ atmosphere for 1 h. The catalyst was removed by filtration through celite and the solved removed under reduced pressure to afford the desired product. This was carried on to the next stage without further purification or characterization.

Stage 6—Preparation of cyclopentyl 4-{4-[3-(hydroxyamino)-3-oxopropyl]benzyl}piperazine-2-carboxylate (Example 113)

Stage 5 crude product (~0.24 mmol) was dissolved in DCM (5 mL) and MeOH (1 mL). 4M HCl solution in dioxane (125 µL, 0.25 mmol) was added and the reaction stirred at RT under N$_2$ atmosphere for 1 h. The reaction mixture was then concentrated under reduced pressure and the residue purified by prep HPLC to afford the title compound (11 mg, 12% over two steps).

LCMS purity 99%, m/z=376 [M+H]$^+$, $^1$H NMR (300 MHz, d$_6$-DMSO) δ: 10.39 (1H, br s), 9.22 (1H, br s), 7.26-7.14 (4H, m), 7.20 (2H, d, J=2.6 Hz), 5.23-5.15 (1H, m), 4.34-4.28 (1H, m), 3.68 (1H, d, J=14.0 Hz), 3.52 (1H, d, J=14.0 Hz), 3.35-3.23 (1H, m), 3.12-3.01 (1H, m), 2.96-2.89 (1H, m), 2.80 (2H, t, J=7.7 Hz), 2.75-2.62 (2H, m), 2.60-2.54 (1H, m), 2.48-2.41 (1H, m), 2.25 (2H, t, J=7.6 Hz), 1.89-1.78 (2H, m), 1.68-1.48 (6H, m).

Example 114

4-{4-[3-(Hydroxyamino)-3-oxopropyl]-benzyl}piperazine-2-carboxylic acid

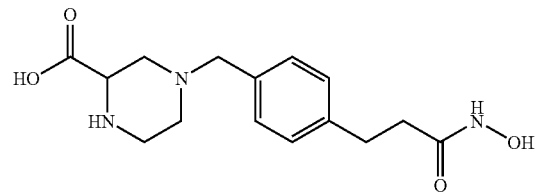 [SMILES: O=C(CCc1ccc(CN2CCNC(C(=O)O)C2)cc1)NO]

The title compound was prepared from Example 113 by the same methodology used to make Example 88.

LCMS purity 95%, m/z=308 [M+H]$^+$, $^1$H NMR (300 MHz, CD$_3$OD) δ: 5.94 (2H, d, J=8.1 Hz), 5.79 (2H, d, J=8.1 Hz), 3.03 (1H, dd, J=11.1, 3.6 Hz), 2.85-2.72 (2H, m), 2.31 (1H, d, J=11.9 Hz), 2.16-2.09 (1H, m), 2.02-1.94 (2H, m), 1.85-1.79 (1H, m), 1.70-1.62 (1H, m), 1.40 (2H, t, J=7.4 Hz), 0.84 (2H, t, J=7.5 Hz).

Measurement of Biological Activities
Histone Deacetylase Activity

The ability of compounds to inhibit histone deacetylase activities was measured using the commercially available HDAC fluorescent activity assay from Biomol. In brief, the Fluor de Lys™ substrate, a lysine with an epsilon-amino acetylation, is incubated with the source of histone deacetylase activity (HeLa nuclear extract) in the presence or absence of inhibitor. Deacetylation of the substrate sensitises the substrate to Fluor de Lys™ developer, which generates a fluorophore. Thus, incubation of the substrate with a source of HDAC activity results in an increase in signal that is diminished in the presence of an HDAC inhibitor.

Data are expressed as a percentage of the control, measured in the absence of inhibitor, with background signal being subtracted from all samples, as follows:

$$\% \text{ activity} = [(S^i - B)/(S^o - B)] \times 100$$

where $S^i$ is the signal in the presence of substrate, enzyme and inhibitor, $S^o$ is the signal in the presence of substrate, enzyme and the vehicle in which the inhibitor is dissolved, and B is the background signal measured in the absence of enzyme.

IC$_{50}$ values were determined by non-linear regression analysis, after fitting the results of eight data points to the equation for sigmoidal dose response with variable slope (% activity against log concentration of Compound), using Graphpad Prism software.

Histone deacetylase activity from crude nuclear extract derived from HeLa cells was used for screening. The preparation, purchased from 4C (Seneffe, Belgium), was prepared from HeLa cells harvested whilst in exponential growth phase. The nuclear extract was prepared according to the methodology described by J. D. Dignam, *Nucl. Acid. Res.*, 1983, 11, 1475-1489, snap frozen in liquid nitrogen and stored at −80° C. The final buffer composition was 20 mM Hepes, 100 mM KCl, 0.2 mM EDTA, 0.5 mM DTT, 0.2 mM PMSF and 20% (v/v) glycerol.

$IC_{50}$ results were allocated to one of 3 ranges as follows:
Range A: $IC_{50}$<100 nM,
Range B: $IC_{50}$ from 101 nM to 1000 nM;
and Range C: $IC_{50}$>1001 Nm;
nt=not tested.

U937 and HUT Cell Inhibition Assay

Cancer cell lines (U937 and HUT) growing in log phase were harvested and seeded at 1000-2000 cells/well (100 μl final volume) into 96-well tissue culture plates. Following 24 h of growth cells were treated with Compound. Plates were then re-incubated for a further 72-96 h before a WST-1 cell viability assay was conducted according to the suppliers (Roche Applied Science) instructions.

Data were expressed as a percentage inhibition of the control, measured in the absence of inhibitor, as follows:

$$\% \text{ inhibition} = 100 - [(S^i/S^o) \times 100]$$

where $S^i$ is the signal in the presence of inhibitor and $S^o$ is the signal in the presence of DMSO.

Dose response curves were generated from 8 concentrations (top final concentration 10 μM, with 3-fold dilutions), using 6 replicates.

$IC_{50}$ values were determined by non-linear regression analysis, after fitting the results to the equation for sigmoidal dose response with variable slope (% activity against log concentration of Compound), using Graphpad Prism software.

$IC_{50}$ results were allocated to one of 3 ranges as follows:
Range A: $IC_{50}$<330 nM,
Range B: $IC_{50}$ from 331 nM to 3300 nM;
and Range C: $IC_{50}$>3301 nM;
nt=not tested.

HeLa Cell Inhibition Assay

HeLa cells growing in log phase were harvested and seeded at 1000 cells/well (200 μl final volume) into 96-well tissue culture plates. Following 24 h of cell growth cells were treated with compounds (final concentration of 20 μM). Plates were then re-incubated for a further 72 h before a sulphorhodamine B (SRB) cell viability assay was conducted according to the methodology described by Skehan et al, *J. Natl. Canc. Inst*, 1990, 82, 1107-1112.

Data were expressed as a percentage inhibition of the control, measured in the absence of inhibitor, as follows: —

$$\% \text{ inhibition} = 100 - [(S^i/S^o) \times 100]$$

where $S^i$ is the signal in the presence of inhibitor and $S^o$ is the signal in the presence of DMSO.

$IC_{50}$ values were determined by non-linear regression analysis, after fitting the results of eight data points to the equation for sigmoidal dose response with variable slope (% activity against log concentration of Compound), using Graphpad Prism software.

$IC_{50}$ results were allocated to one of 3 ranges as follows:
Range A: $IC_{50}$<330 nM,
Range B: $IC_{50}$ from 331 nM to 3300 nM;
and Range C: $IC_{50}$>3301 nM;
nt=not tested.

Results Table:

| Example | HDAC activity | U937 activity | HUT activity | HeLa activity |
|---|---|---|---|---|
| 1 | B | C | C | C |
| 2 | A | B | B | B |
| 3 | A | B | B | B |
| 4 | A | B | B | B |
| 5 | A | B | B | B |
| 6 | B | B | B | C |
| 7 | B | B | B | C |
| 8 | B | B | B | B |
| 9 | C | C | C | C |
| 10 | B | B | B | B |
| 11 | B | B | B | C |
| 12 | B | B | B | C |
| 13 | C | C | B | C |
| 14 | A | A | A | B |
| 15 | A | A | A | B |
| 16 | B | B | B | C |
| 17 | B | A | B | C |
| 18 | B | B | B | C |
| 19 | B | B | C | C |
| 20 | B | A | B | C |
| 21 | A | A | A | B |
| 22 | B | B | B | nt |
| 23 | B | A | B | nt |
| 24 | A | A | A | nt |
| 25 | A | A | B | B |
| 26 | B | A | B | B |
| 27 | B | A | B | B |
| 28 | B | A | B | B |
| 29 | B | B | B | B |
| 30 | B | A | A | nt |
| 31 | A | A | B | nt |
| 32 | A | B | B | nt |
| 33 | B | A | B | nt |
| 34 | B | A | A | nt |
| 35 | C | A | B | C |
| 36 | B | A | A | B |
| 37 | B | A | A | B |
| 38 | B | B | C | C |
| 39 | B | A | B | nt |
| 40 | A | B | B | nt |
| 41 | B | A | B | nt |
| 42 | C | A | B | nt |
| 43 | C | B | B | nt |
| 44 | B | B | B | nt |
| 45 | C | A | B | nt |
| 46 | C | C | C | nt |
| 47 | C | C | B | nt |
| 48 | C | B | B | nt |
| 49 | C | C | C | nt |
| 50 | B | B | B | nt |
| 51 | C | C | C | nt |
| 52 | C | B | C | nt |
| 53 | A | A | A | nt |
| 54 | A | A | B | nt |
| 55 | A | A | A | B |
| 56 | A | A | A | B |
| 57 | A | A | A | C |
| 58 | A | A | A | B |
| 59 | A | A | A | nt |
| 60 | A | A | A | nt |
| 61 | A | A | A | nt |
| 62 | A | A | A | nt |
| 63 | A | A | A | nt |
| 64 | B | B | B | nt |
| 65 | B | A | B | nt |
| 66 | A | A | B | nt |
| 67 | B | A | B | nt |
| 68 | A | A | B | nt |
| 69 | B | B | B | nt |
| 70 | B | A | B | nt |
| 71 | C | B | B | nt |
| 72 | B | B | B | nt |
| 73 | B | B | B | B |
| 74 | B | A | B | C |

| Example | HDAC activity | U937 activity | HUT activity | HeLa activity |
|---|---|---|---|---|
| 75 | B | A | A | B |
| 76 | A | A | A | nt |
| 77 | B | A | B | nt |
| 78 | B | A | B | nt |
| 79 | C | B | B | B |
| 80 | B | A | A | B |
| 81 | B | A | A | B |
| 82 | A | B | B | B |
| 83 | B | B | A | B |
| 84 | C | C | C | nt |
| 85 | A | A | A | nt |
| 86 | B | A | B | nt |
| 87 | B | B | B | nt |
| 88 | A | nt | nt | nt |
| 89 | A | nt | nt | nt |
| 90 | B | nt | nt | nt |
| 91 | B | nt | nt | nt |
| 92 | B | nt | nt | nt |
| 93 | B | nt | nt | nt |
| 94 | B | nt | nt | nt |
| 95 | B | nt | nt | nt |
| 96 | B | nt | nt | nt |
| 97 | A | nt | nt | nt |
| 98 | C | nt | nt | nt |
| 99 | C | nt | nt | nt |
| 100 | C | nt | nt | nt |
| 101 | A | nt | nt | nt |
| 102 | A | nt | nt | nt |
| 103 | A | nt | nt | nt |
| 104 | B | nt | nt | nt |
| 105 | C | nt | nt | nt |
| 106 | B | nt | nt | nt |
| 107 | C | nt | nt | nt |
| 108 | A | nt | nt | nt |
| 109 | C | nt | nt | nt |
| 110 | B | nt | nt | nt |
| 111 | C | nt | nt | nt |
| 112 | A | nt | nt | nt |
| 113 | B | B | B | nt |
| 114 | C | nt | nt | nt |

"nt" means "not tested to date".

Macrophage Selectivity:

Table A illustrates the way in which the addition of an esterase motif can significantly increase macrophage(monocyte) selectivity.

Example 14 is 30 fold more potent as an anti-proloferative agent in the monocytic cell line U937 than the known HDAC inhibitor belinostat which is currently in Phase II clinical trials (Glaser K B, Biochem. Pharmacol., 2007, 74, 659-671). This macrophage(monocyte) selectivity results from selective cleavage of the ester as shown by the accumulation of the resultant acid inside the U937 cell line but not the HUT cell line. Only the the U937 cell line expresses HCE-1. Furthermore, the potency of Example 14 in the non-monocytic cell line HUT is what would be expected based on its enzyme activity i.e. the ratio of enzyme to cell potency is the same for Example 14 and belinostat.

TABLE A

| Compound | Structure | Inhibition of HDAC (IC50-nM) | Inhibition of U937 cell proliferation (IC50-nM) | Ratio U937/enzyme | Acid accumulation at 6 h in U937 (ng/ml) | Inhibition of HUT78 cell proliferation (IC50-nM) | Ratio HUT78/enzyme | Acid accumulation at 6 h in HUT78 (ng/ml) |
|---|---|---|---|---|---|---|---|---|
| Belinostat | 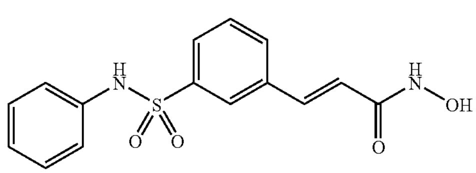 [SMILES: O=C(/C=C/c1cccc(S(=O)(=O)Nc2ccccc2)c1)NO] | 13 | 180 | 14 | — | 31 | 2.4 | — |
| Example 14 | 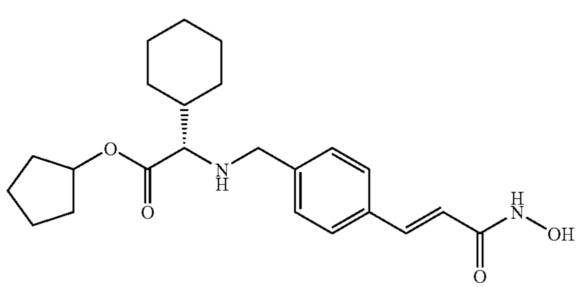 [SMILES: O=C(/C=C/c1ccc(CN[C@H](C(=O)OC2CCCC2)C2CCCCC2)cc1)NO] | 59 | 5 | 0.08 | 27 | 230 | 3.8 | 0 |

Broken Cell Carboxylesterase Assay

Any given compound of the present invention wherein $R_1$ is an ester group may be tested to determine whether it meets the requirement that it be hydrolysed by intracellular esterases, by testing in the following assay.

Preparation of Cell Extract

U937 or Hut78 tumour cells (~109) were washed in 4 volumes of Dulbeccos PBS (~1 litre) and pelleted at 525 g for 10 min at 4° C. This was repeated twice and the final cell pellet was resuspended in 35 mL of cold homogenising buffer (Trizma 10 mM, NaCl 130 mM, $CaCl_2$ 0.5 mM pH 7.0 at 25° C.). Homogenates were prepared by nitrogen cavitation (700 psi for 50 min at 4° C.). The homogenate was kept on ice and supplemented with a cocktail of inhibitors at final concentrations of:
Leupeptin 1 µM
Aprotinin 0.1 µM
E64 8 µM
Pepstatin 1.5 µM
Bestatin 162 µM
Chymostatin 33 µM
After clarification of the cell homogenate by centrifugation at 525 g for 10 min, the resulting supernatant was used as a source of esterase activity and was stored at –80° C. until required.

Measurement of Ester Cleavage

Hydrolysis of esters to the corresponding carboxylic acids can be measured using the cell extract, prepared as above. To this effect cell extract (~30 µg/total assay volume of 0.5 ml) was incubated at 37° C. in a Tris-HCl 25 mM, 125 mM NaCl buffer, pH 7.5 at 25° C. At zero time the ester (substrate) was then added at a final concentration of 2.5 µM and the samples were incubated at 37° C. for the appropriate time (usually 0 or 80 min). Reactions were stopped by the addition of 3× volumes of acetonitrile. For zero time samples the acetonitrile was added prior to the ester compound. After centrifugation at 12000 g for 5 min, samples were analysed for the ester and its corresponding carboxylic acid at room temperature by LCMS (Sciex API 3000, HP1100 binary pump, CTC PAL). Chromatography was based on an AceCN (75×2.1 mm) column and a mobile phase of 5-95% acetonitrile in water/0.1% formic acid.

Rates of Hydrolysis are Expressed in pg/mL/min.

HDACs are intracellular enzymes. The following Table B presents data showing that several amino acid ester motifs, conjugated to various intracellular enzyme inhibitors by several different linker chemistries are all hydrolysed by intracellular carboxyesterases to the corresponding acid.

TABLE B

| Structure of amino acid ester conjugate | R | Linker | Hydrolysis Rate Range U937 Cells (pg/mL/min) | Preparation of amino ester conjugate |
|---|---|---|---|---|
| 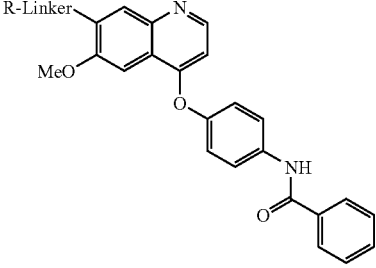 | 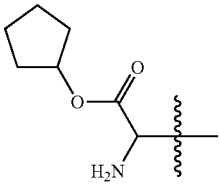 | —CH2CH2O— | 100-1000 | WO2006117552 |
| 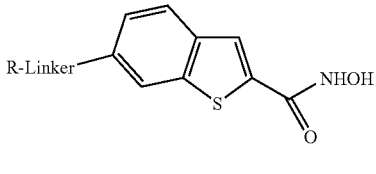 | 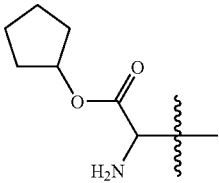 [SMILES: *C(N)C(=O)OC1CCCC1] | —(CH₂)₃O—⟨ ⟩—CH₂NHCH₂— | 1000-50000 | WO2006117548 |
| 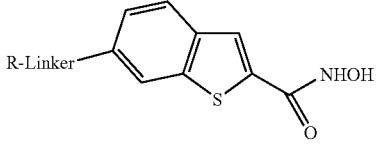 | 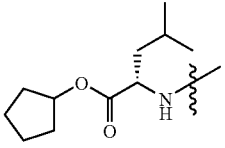 [SMILES: *N[C@@H](CC(C)C)C(=O)OC1CCCC1] | —CH₂—⟨ ⟩—CH₂NHCH₂— | >50000 | WO2006117549 |
| 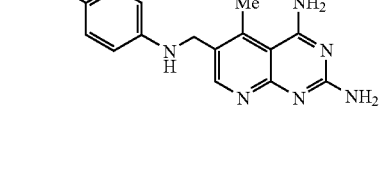 | 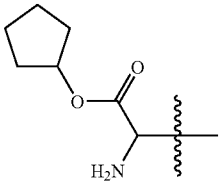 [SMILES: *C(N)C(=O)OC1CCCC1] | —CH2CH2O— | >50000 | WO2006117567 |

TABLE B-continued

| Structure of amino acid ester conjugate | R | Linker | Hydrolysis Rate Range U937 Cells (pg/mL/min) | Preparation of amino ester conjugate |
|---|---|---|---|---|
| | | —CH2CH2O— | 1000-50000 | WO2006117567 |
| | | —CH2— | 1000-50000 | WO2006117567 |
| | | —CO— | >50000 | WO2006117567 |
| | | —CH2—⟨⟩—CH2NHCH2— | >50000 | WO2006117549 |
| | | —CH2—⟨⟩—CH2NHCH2— | >50000 | WO2006117549 |

The invention claimed is:

1. A compound which is cyclopentyl (2S)-cyclohexyl[({6-[3-(hydroxyamino)-3-oxopropyl]pyridin-3-yl}methyl)amino]acetate, of formula:

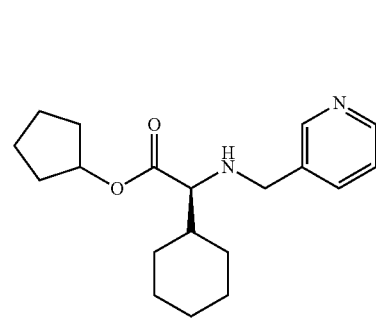

or a pharmaceutically acceptable salt or N-oxide thereof.

2. A pharmaceutical composition comprising a compound according to claim 1, together with a pharmaceutically acceptable carrier.

3. A pharmaceutical composition as claimed in claim 2 which is adapted for topical administration.

4. A The compound cyclopentyl (2S)-cyclohexyl[({6-[3-(hydroxyamino)-3-oxopropyl]pyridin-3-yl}methyl)amino]acetate, of formula;

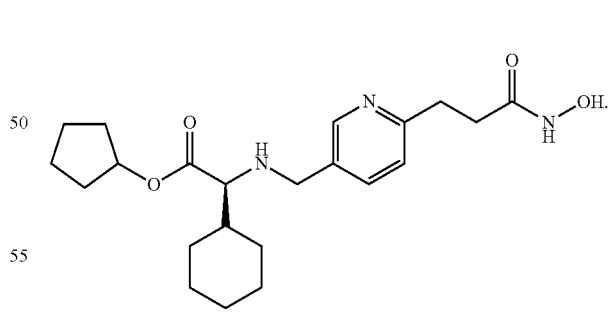

5. A pharmaceutical composition comprising a compound as claimed in claim 4, together with a pharmaceutically acceptable carrier.

6. A pharmaceutical composition as claimed in claim 5 which is adapted for topical administration.

7. The compound (2S)-Cyclohexyl[({6-[3-(hydroxyamino)-3-oxopropyl]pyridin-3-yl}methyl)amino]acetic acid.

8. A pharmaceutical composition comprising a compound according to claim 1, wherein said composition is adapted for oral administration.

9. A pharmaceutical composition according to claim 8, wherein the composition is present in the form of a tablet or capsule.

10. A pharmaceutical composition according to claim 8, wherein said composition is present in the form of an oral liquid preparation.

11. A pharmaceutical composition comprising the compound according to claim 4, wherein said composition is adapted for oral administration.

12. A pharmaceutical composition according to claim 11, wherein the composition is present in the form of a tablet or capsule.

13. A pharmaceutical composition according to claim 11, wherein said composition is present in the form of an oral liquid preparation.

\* \* \* \* \*